US012560604B2

(12) United States Patent
Sarkar et al.

(10) Patent No.: US 12,560,604 B2
(45) Date of Patent: Feb. 24, 2026

(54) BACTERIAL BIOSENSOR SYSTEM

(71) Applicant: REGENTS OF THE UNIVERSITY OF MINNESOTA, Minneapolis, MN (US)

(72) Inventors: Casim A. Sarkar, Minneapolis, MN (US); Samira M. Azarin, Minneapolis, MN (US); Qiuge Zhang, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 787 days.

(21) Appl. No.: 17/818,899

(22) Filed: Aug. 10, 2022

(65) Prior Publication Data

US 2023/0063616 A1     Mar. 2, 2023

Related U.S. Application Data

(60) Provisional application No. 63/261,989, filed on Oct. 1, 2021, provisional application No. 63/260,135, filed on Aug. 10, 2021.

(51) Int. Cl.
| | |
|---|---|
| *C12N 1/20* | (2006.01) |
| *A61K 48/00* | (2006.01) |
| *C07K 14/245* | (2006.01) |
| *G01N 33/569* | (2006.01) |

(52) U.S. Cl.
CPC .... *G01N 33/56911* (2013.01); *A61K 48/0066* (2013.01); *C07K 14/245* (2013.01); *C12N 1/20* (2013.01)

(58) Field of Classification Search
CPC ........ C12N 15/70; C12N 15/635; C12Q 1/02; C07K 2319/32
See application file for complete search history.

(56) References Cited

PUBLICATIONS

Yokobayashi et al., "Directed evolution of a genetic circuit," PNAS, December, vol. 99, No. 26, pp. 16587-16591. (Year: 2002).*
Mireku et al.., "Structural basis of nanobodymediated blocking of BtuF, the cognate substrate-binding protein of the *Escherichia coli* vitamin B12 transporter BtuCD," Scientific Reports, vol. 7, pp. 1-12. (Year: 2017).*
Kim et al., "Transcription factor-based biosensors and inducible systems in non-model bacteria: current progress and future directions," Current Opinions in Biotechnology, vol. 64, pp. 39-46. (Year: 2020).*
Ahuja et al., "Structural Analysis of Bacterial ABC Transporter Inhibition by an Antibody Fragment," Structure, Apr. 7, 2015, vol. 23, pp. 713-723.
Anderson et al., "The BfeR Regulator Mediates Enterobactin-Inducible Expression of Bordetella Enterobactin Utilization Genes,"
Journal of Bacteriology, Nov. 2004, vol. 186, No. 21, pp. 7302-7311.
Biedendieck et al., "A sucrose-inducible promoter system for the intra-and extracellular protein production in Bacillus megaterium," Journal of Biotechnology, 2007, vol. 132, No. 4, pp. 426-430.
Boos et al., "Maltose/Maltodextrin System of *Escherichia coli*: Transport, Metabolism, and Regulation," Microbiology and Molecular Biology Reviews, Mar. 1998, vol. 62, No. 1, pp. 204-229.
Cameron et al., "Tunable protein degradation in bacteria," Author manuscript, Nature Biotechnology, Dec. 2014, vol. 32, No. 12, pp. 1276-1282.
Carter et al., "Phage Display Reveals Multiple Contact Sites between FhuA, an Outer Membrane Receptor of *Escherichia coli*, and TonB," Journal of Molecular Biology, 2006, vol. 357, pp. 236-251.
Cervantes et al., "Role for Vitamin B12 in Light Induction of Gene Expression in the Bacterium Myxococcus xanthus," Journal of Bacteriology, Apr. 2002, vol. 184, No. 8, pp. 2215-2224.
Chang et al., "Microbially derived biosensors for diagnosis, monitoring and epidemiology," Microbial Biotechnology, 2017, vol. 10, No. 5, pp. 1031-1035.
Chen et al., "Characterization of 582 natural and synthetic terminators and quantification of their design constraints," Nature Methods, 2013, vol. 10, No. 7, pp. 659-664.
Chen et al., "Construction of a bacterial surface display system based on outer membrane protein F," Microbial Cell Factories, 2019, vol. 18, No. 70, 13 pages.
Danot, Olivier, "The inducer maltotriose binds in the central cavity of the tetratricopeptide-like sensor domain of MalT, a bacterial STAND transcription factor," Molecular Microbiology, 2010, vol. 77, No. 3, pp. 628-641.
Daringer et al., "Modular Extracellular Sensor Architecture for Engineering Mammalian Cell-based Devices," ACS Synthetic Biology, 2014, vol. 3, pp. 892-902.
Datsenko et al., "One-step inactivation of chromosomal genes in *Escherichia coli* K-12 using PCR products," Proceedings of the National Academy of Sciences, Jun. 6, 2000, vol. 97, No. 12, pp. 6640-6645.
Davidson et al., "Mechanism of maltose transport in *Escherichia coli*: Transmembrane signaling by periplasmic binding proteins," Proceedings of the National Academy of Sciences, Mar. 1992, vol. 89, pp. 2360-2364.
Dippel et al., "The Maltodextrin System of Escherichia coli: Metabolism and Transport," Journal of Bacteriology, Dec. 2005, vol. 187, No. 24, pp. 8322-8331.
Dumas et al., "Sugar Transport through Maltoporin of *Escherichia coli6*; Role of Polar Tracks," The Journal of Biological Chemistry, Jun. 30, 2000, vol. 275, No. 26, pp. 19747-19751.
Dutzler et al., "Crystal structures of various maltooligosaccharides bound to maltoporin reveal a specific sugar translocation pathway," Structure, Feb. 1996, vol. 4, Issue 2, pp. 127-134.

(Continued)

*Primary Examiner* — Young J Kim
(74) *Attorney, Agent, or Firm* — McKee, Voorhees & Sease, PLC

(57) ABSTRACT

The disclosure relates to a biosensor on the bacterial cell surface for sensing and responding to extracellular molecules. Related methods of using the bacterial cells to inducibly express a protein of interest and/or a bioactive RNA molecule in a subject are disclosed. Related methods of using the bacterial cells to inducibly express a protein of interest or to detect a target of interest in a sample are also disclosed.

13 Claims, 33 Drawing Sheets

Specification includes a Sequence Listing.

(56) References Cited

PUBLICATIONS

Etz et al., "Bacterial Phage Receptors, Versatile Tools for Display of Polypeptides on the Cell Surface," Journal of Bacteriology, Dec. 2001, vol. 183, No. 23, pp. 6924-6935.

Fernandez-Rodriguez et al., "Post-translational control of genetic circuits using Potyvirus proteases," Nucleic Acids Research, 2016, vol. 44, No. 13, pp. 6493-6502.

Fiss et al., "Properties and proteolysis of ferric enterobactin outer membrane receptor in Escherichia coli K12," Biochemistry, 1982, vol. 21, No. 18, pp. 4517-4522.

Freudl, Roland, "Insertion of peptides into cell-surface-exposed areas of the Escherichia coli OmpA protein does not interfere with export and membrane assembly," Gene, 1989, vol. 82, No. 2, pp. 229-236.

Friedland et al., "Synthetic Gene Networks that Count," Author manuscript, Science, May 29, 2009, vol. 324, No. 5931, pp. 1199-1202.

Green et al., "Complex cellular logic computation using ribocomputing devices," Author manuscript, Nature, Aug. 3, 2017, vol. 548, No. 7665, pp. 117-121.

Jaffe et al., "Role of Porin Proteins OmpF and OmpC in the Permeation of β-Lactams," Antimicrobial Agents and Chemotherapy, Dec. 1982, vol. 22, No. 6, pp. 942-948.

Janssen et al., "PhoE protein as a carrier for foreign epitopes," International Reviews of Immunology, 1994, vol. 11, No. 2, pp. 113-121.

Jiang et al., "A potential peptide derived from cytokine receptors can bind proinflammatory cytokines as a therapeutic strategy for anti-inflammation," Scientific Reports, 2019, vol. 9, Article 2317, 15 pages.

Korteland et al., "PhoE Protein Pore of the Outer Membrane of Escherichia coli K12 Is a Particularly Efficient Channel for Organic and Inorganic Phosphate," Biochimica et Biophysica Act, 1982, vol. 690, pp. 282-289.

Krajewska et al., "Pyrimidine nucleoside analogues as inducers of pyrimidine nucleoside catabolizing enzymes in Salmonella typhimurium," Molecular Biology Reports, 1975, vol. 2, pp. 295-301.

Kuhlman et al., "Combinatorial transcriptional control of the lactose operon of Escherichia coli," Proceedings of the National Academy of Sciences, Apr. 3, 2007, vol. 104, No. 14, pp. 6043-6048.

Leydon et al., "Engineering synthetic signaling in plants," Annual Review of Plant Biology, 2020, vol. 71, pp. 767-788.

Liu et al., "Stretchable living materials and devices with hydrogel-elastomer hybrids hosting programmed cells," Proceedings of the National Academy of Sciences, Feb. 28, 2017, vol. 114, No. 9, pp. 2200-2205.

Lynch et al., "Emerging strategies for engineering Escherichia coli Nissle 1917-based therapeutics," Trends in Pharmacological Sciences, Sep. 2022, vol. 43, No. 9, pp. 772-786.

Maier et al., "Pore-forming Activity of the Tsx Protein from the Outer Membrane of Escherichia coli," The Journal of Biological Chemistry, Feb. 15, 1988, vol. 263, No. 5, pp. 2493-2499.

Mills et al., "TonB-dependent ligand trapping in the BtuB transporter," Biochimica et Biophysica Acta, 2016, vol. 1858, pp. 3105-3112.

Ming-Ming et al., "Construction and characterization of a novel maltose inducible expression vector in Bacillus subtilis," Biotechnology Letters, 2006, vol. 28, pp. 1713-1718.

Mireku et al., "Structural basis of nanobody-mediated blocking of BtuF, the cognate substrate-binding protein of the Escherichia coli vitamin B12 transporter BtuCD," Scientic Reports, 2017, vol. 7, No. 14296, 12 pages.

Morsut et al., "Engineering Customized Cell Sensing and Response Behaviors Using Synthetic Notch Receptors," Cell, vol. 164, Issue 4, Feb. 2016, pp. 780-791.

Nath et al., "Protein Degradation in Escherichia coli," The Journal of Biological Chemistry, Jun. 10, 1970, vol. 245, No. 11, pp. 2889-2900.

Nguyen et al., "Wearable materials with embedded synthetic biology sensors for biomolecule detection," Nature Biotechnology, 2021, vol. 39, pp. 1366-1374.

Nikaido et al., "Porin Channels in Escherichia coli: Studies with Liposomes Reconstituted from Purified Proteins," Journal of Bacteriology, Jan. 1983, vol. 153, No. 1, pp. 241-252.

Okeke et al., "The importance of molecular diagnostics for infectious diseases in low-resource settings," Nature Reviews Microbiology, Sep. 2021, vol. 19, pp. 547-548.

Palani et al., "Synthetic conversion of a graded receptor signal into a tunable, reversible switch," Molecular Systems Biology, 2011, vol. 7, Article 480, 7 pages.

Pallesen et al., "Chimeric FimH adhesin of Type 1 fimbriae: a bacterial surface display system for heterologous sequences," Microbiology, 1995, vol. 141, pp. 2839-2848.

Pierce et al., "Escherichia coli K-12 Envelope Proteins Specifically Required for Ferrienterobactin Uptake," Journal of Bacteriology, Jun. 1986, vol. 166, No. 3, pp. 930-936.

Proshkin et al., "Cooperation between Translating Ribosomes and RNA Polymerase in Transcriptioin Elongation," Author manuscript, Science, Apr. 23, 2010, vol. 328, No. 5977, pp. 504-508.

Quartararo et al., "Ultra-large chemical libraries for the discovery of high-affinity peptide binders," Nature Communications, 2020, vol. 11, No. 3183, 11 pages.

Razo-Mejia et al., "Tuning transcriptional regulation through signaling: A predictive theory of allosteric induction," Cell Systems, Apr. 25, 2018, vol. 6, Issue 4, pp. 456-469.

Reid et al., "Sucrose utilisation in bacteria: genetic organisation and regulation," Applied Microbiology and Biotechnology, 2005, vol. 67, pp. 312-321.

Rice et al., "Bacterial display using circularly permuted outer membrane protein OmpX yields high affinity peptide ligands," Protein Science, 2006, vol. 15, pp. 825-836.

Riglar et al., "Engineering bacteria for diagnositic and therapeutic applications," Nature Reviews Microbiology, Apr. 2018, vol. 16, pp. 214-225.

Shah et al., "Robust Network Topologies for Generating Switch-Like Cellular Responses, "PLoS Computational Biology, Jun. 2011, vol. 7, Issue 6, e1002085, 12 pages.

Shin et al., "Programming Escherichia coli to function as a digital display," Molecular Systems Biology, 2020, vol. 16, e9401, 12 pages.

Sousa et al., "Metalloadsorption by Escherichia coli Cells Displaying Yeast and Mammalian Metallothioneins Anchored to the Outer Membrane Protein LamB," Journal of Bacteriology, May 1998, vol. 180, No. 9, pp. 2280-2284.

Stanton et al., "Genomic Mining of Prokaryotic Repressors for Orthogonal Logic Gates," Author manuscript, Nature Chemical Biology, Feb. 2014, vol. 10, No. 2, pp. 99-105.

Sun et al., "Characteristics of Sucrose Transport through the Sucrose-Specific Porin ScrY Studied by Molecular Dynamics Simulations," Frontiers in Bioengineering and Biotechnology, Feb. 2016, vol. 4, Article 9, 10 pages.

Tapio et al., "The malZ gene of Escherichia coli, a member of the maltose regulon, encodes a maltodextrin glucosidase," The Journal of Biological Chemistry, Oct. 15, 1991, vol. 266, No. 29, pp. 19450-19458.

Troxell et al., "Transcriptional regulation by Ferric Uptake Regulator (Fur) in pathogenic bacteria," Frontiers in Cellular and Infection Microbiology, Oct. 2013, vol. 3, Article 59, 13 pages.

Vergalli et al., "Porins and small-molecule translocation across the outer membrane of Gram-negative bacteria," Author manuscript, Nature Reviews Microbiology, 2020, vol. 18, No. 3, pp. 164-176.

Wang et al., "A modular cell-based biosensor using engineered genetic logic circuits to detect and integrate multiple environmental signals," Biosensors and Bioelectronics, 2013, vol. 40, pp. 368-376.

Wang et al., "Channel Specificity: Structural Basis for Sugar Discrimination and Differential Flux Rates in Maltoporin," Journal of Molecular Biology, 1997, vol. 272, pp. 56-63.

Wang, Ying, "The function of OmpA in Escherichia coli," Biochemical and Biophysical Research Communications, 2002, vol. 292, No. 2, pp. 396-401.

(56) References Cited

PUBLICATIONS

Waterhouse et al., "Swiss-Model: homology modelling of protein structures and complexes," Nucleic Acids Research, 2018, vol. 46, pp. W296-W303.

Wegner et al., "Characterization and Optimization of Peptide Arrays for the Study of Epitope-Antibody Interactions Using Surface Plasmon Resonance Imaging," Analytical Chemistry, Oct. 15, 2002, vol. 74, No. 20, pp. 5161-5168.

Xu et al., "Display of Polyhistidine Peptides on the *Escherichia coli* Cell Surface by Using Outer Membrane Protein C as an Anchoring Motif," Applied and Environmental Microbiology, Nov. 1999, vol. 65, No. 11, pp. 5142-5147.

Yokobayashi et al., "Directed evolution of a genetic circuit," Proceedings of the National Academy of Sciences, Dec. 24, 2002, vol. 99, No. 26, pp. 16587-16591.

Zargaran et al., "Detecting the Dominant T and B Epitopes of Klebsiella pneumoniae Ferric Enterobactin Protein (FepA) and Introducing a Single Epitopic Peptide as Vaccine Candidate," International Journal of Peptide Research and Therapeutics, 2021, vol. 27, pp. 2209-2221.

* cited by examiner

| Step | 1 | 2 | 3 | 4 | 5 | 6 |
|---|---|---|---|---|---|---|
| | Step1: tranformation | Step2: seed culture | Step3: Pre-induction of MalT and LamB | Step4: Post-induction of MalT and LamB | Step5: Antibody binding | Step6: Maltodextrin induction |
| Medium | LB | LB | M9 | M9 | M9 | M9 |
| Temp (°C ) | 37 | 37 | 37 | 30 | 37 | 37 |
| Duration | 24-48 h | 16 h | 4 h | 8 h | 30 min | 16 h |
| Antibiotics | Carb+Cm | Carb+Cm | Carb+Cm | Carb+Cm | Carb+Cm | Carb+Cm |
| Inducers | / | / | Maltodextrin (40 mM) | Maltodextrin (40 mM) aTc (LamB), IPTG(MalT) | / | Maltodextrin (10-20 mM) |
| Antibody | / | / | / | / | mAb | mAb |

*FIG. 4A*

KCF peptide: KCRKEMFKQKLPYSTVYF (18 AAs)

LamB monomer    blocked by TNF-alpha    blocked by IL-6

Strain A

Strain B

Strain C side view                                    top view

LamB monomer          ScrY monomer          ScrY and LamB alignment

ORF

ctgattccagccgtgaaggaaaagcaactggtttagactcttaatattcaaaaa
atgcattatacgctctctcttttacaaaagggagagcgtataatgcattaaaaa
agataaaaatgagtaggtaaaaagaaggaatattttttctgaaaacatacttt
agacctttattattatcatcctaatctttagaaaggaaaaagaatagaacgttttc
atgtccggctaataaaaaaaaggtactgattttttcaagagataaaaacagaatg
gtcggaaagtataaaaacgaatggtcggaaagtataaaaaacggaatagcgt
tttcaatgctggaaagataaagtgtttaatcatgtagaaagtatcaaacgcaac
gtctggaaatcgtggtttgaaatgtaaaaaagccattttttgttggaaaaacggtt
acataaaaaaggctcttacacgtaaactttggtcctagttacagctcaatgaaa
aagataaaaatgagaaatagctacatttggcatgtttgactttcgtcatttatcca
agtaatctttggttgaacggaaccggttctgtttcggattttttgatagctaattg
aattaataaatttatattctttactaacacaaaaggagaaaacatATG

*FIG. 7D*

Transcription repressor

Decoy RNA sequences

Orthogonal protease

BACTERIAL BIOSENSOR SYSTEM

CROSS-REFERENCE TO RELATED APPLICATIONS

This application claims the benefit of priority to U.S. Provisional Patent Application No. 63/261,989, filed Oct. 1, 2021, and U.S. Provisional Patent Application No. 63/260, 135, filed Aug. 10, 2021, which are incorporated herein by reference in their entirety.

GOVERNMENT SUPPORT

This invention was made with government support under Grant No. DK114453 awarded by the National Institutes of Health. The Government has certain rights in the invention.

SEQUENCE LISTING

The instant application contains Sequence Listings which have been submitted in XML format via Patent Center and are hereby incorporated by reference in their entirety. Said XML copy, created Aug. 4, 2022, is named "P13621US02_SequenceListing" and is 33,869 bytes in size.

BACKGROUND

Bacterial therapeutics have shown significant potential in the treatment of a variety of diseases such as cancer, diabetes, and intestinal inflammation. *Escherichia coli* is widely used in the biotechnology industry and has the potential to be used as a diagnostic or therapeutic agent, but many such applications are limited by the inability of bacteria (particularly Gram-negative bacteria) to sense and respond to cell-impermeable molecules such as certain proteins in the environment.

SUMMARY

Bacterial cells comprising (i) a first outer membrane transport protein comprising a heterologous target-specific binding peptide inserted in an extracellular portion of the membrane transport protein; (ii) an inducible promoter which is operably linked to a polynucleotide encoding a repressor protein, wherein said promoter is induced by a compound, and wherein the compound is internalized within the cell by the outer membrane transport protein; and (iii) a repressible promoter which is operably linked to a polynucleotide encoding a protein and/or a bioactive RNA molecule of interest, wherein said repressible promoter can be repressed by the repressor protein are provided. In certain embodiments, internalization of the compound is inhibited by the presence of a target which binds to the heterologous target-specific binding peptide. In certain embodiments, extracellular presence of the compound and a target which binds to the heterologous target-specific binding peptide results in an increase in expression of the protein and/or bioactive RNA molecule of interest in comparison to expression of the protein and/or a bioactive RNA molecule of interest in the extracellular presence of the compound when the target is present at lower concentrations or absent.

Systems for detection of target in a sample comprising the aforementioned bacterial cells in an extracellular media comprising the target and the compound are provided.

Methods of inducibly expressing a protein and/or a bioactive RNA molecule of interest in a subject comprising administering the aforementioned bacterial cells to the subject, wherein the protein and/or a bioactive RNA molecule of interest is expressed in the extracellular presence of the compound and a target which binds to the heterologous target-specific binding peptide are provided.

Methods of detecting a target of interest in a sample comprising (i) contacting the aforementioned bacterial cells with the sample and the compound, wherein the protein of interest is a reporter protein; and (ii) detecting the reporter protein to determine the presence of the target in the sample, wherein expression of the reporter protein is increased in samples containing the target in comparison to expression of the reporter protein in a control bacterial cell contacted with the compound and a control sample lacking or deficient in the target are provided.

Bacterial cells comprising: (i) a first outer membrane transport protein comprising a heterologous target-specific binding peptide inserted in an extracellular portion of the membrane transport protein; (ii) an inducible promoter which is operably linked to a polynucleotide encoding a protein and/or a bioactive RNA molecule of interest, wherein said promoter is induced by a compound, and wherein the compound is internalized within the cell by the outer membrane transport protein are provided.

Bacterial cells comprising: (i) a first outer membrane transport protein comprising a heterologous target-specific binding peptide inserted in an extracellular portion of the membrane transport protein; (ii) a first promoter which is inducible and operably linked to a polynucleotide encoding a regulator protein and/or a regulator RNA molecule, wherein said promoter is induced by a compound, and wherein the compound is internalized within the cell by the outer membrane transport protein; and (iii) a second promoter which is operably linked to a protein and/or a bioactive RNA molecule of interest, wherein the second promoter is repressed by the regulator protein or wherein expression of the protein of interest is inhibited by the regulator protein and/or wherein the expression of the protein of interest is inhibited by the regulator RNA molecule are provided.

BRIEF DESCRIPTION OF THE DRAWINGS

FIG. 3A shows an SDS-PAGE of the *E. coli* outer membrane fraction after induction of LamB protein expression.

FIG. 3B shows flow cytometry of *E. coli* cells transformed with a plasmid expressing recombinant wild-type (WT) LamB, LamB with FLAG tag peptide insertions, or LamB with myc tag peptide insertions. After induction, the cell culture was co-incubated with AF 488 conjugated FLAG tag antibody or AF 488 conjugated myc tag antibody for 0.5 h or 8.5 h at 37° C., and then washed two times using PBS before measurement.

FIG. 3C shows time curves of mCherry expression controlled by the maltose induction system with different maltodextrin concentrations. Left: overexpressed WT LamB; middle: overexpressed LamB with target-specific binding peptide (FLAG tag) insertions in loop 4 and loop 9; right: overexpressed LamB with myc tag insertions in loop 4 and loop 9.

FIG. 4A-D show biosensor experimental characterization and mathematical simulation.

FIG. 4A shows experimental procedures and conditions for biosensor experimental characterization. First, single colonies transformed with the desired plasmid were grown in LB medium with appropriate antibiotics to get the seed culture. The seed culture was then inoculated in M9 medium and grown at 37° C. until OD600 reached 0.8. Next the culture was cooled to 30° C. and inducers IPTG and aTc were added for induction of MalT and LamB expression. A high concentration of maltodextrin (40 mM) was present in step 3 and step 4 to minimize background expression of YFP. Next, the induced culture was washed once using M9 medium with appropriate antibiotics to eliminate maltodextrin and the inducers IPTG and aTc. Finally, FLAG tag monoclonal antibody (mAb) was added to the M9 cell culture and incubated for 30 min at 37° C., and the output YFP expression was monitored in a plate reader at 37° C. after adding maltodextrin at appropriate concentrations.

FIG. 4B shows the engineered signaling pathway of the designed biosensor for the compound maltodextrin. mAb can block the LamB transporter through specific binding to the fused target-specific binding peptide tags on LamB. The MD transported through LamB is hydrolyzed in the periplasm to maltose, which then enters the cytoplasm to activate MalT for SrpR expression, which, in turn, represses YFP expression. (MD: maltodextrin (n=4-7), LamB: maltodextrin transporter on the outer membrane, mAb: FLAG tag monoclonal antibody, MD(peri): maltodextrin in the periplasm, M(peri): maltose (n=2) in the periplasm, MalT: inactivated maltose transcription activator; MalT*: activated maltose transcription activator, SrpR: Srp promoter repressor.)

FIG. 4C shows experimental (left) and computational (right) dose response of YFP output vs. FLAG tag antibody input for various LamB expression levels, controlled by aTc concentration (error bars: three technical replicates).

FIG. 4D shows experimental (left) and computational (right) dose response of YFP output vs. FLAG tag antibody input for various MalT expression levels, controlled by IPTG concentration (error bars: three technical replicates).

FIG. 5A illustrates that human cytokines TNF-α and IL-6 can both in principle block LamB channels for maltodextrin transport through specific binding to the engineered peptide KCF18 inserted in LamB outer loops.

FIG. 5B shows time curves of YFP expression, repressed by increasing concentrations of maltodextrin, in a host strain with overexpressed recombinant LamB with KCF18 insertions at loop 4 and loop 9.

FIG. 5C shows time curves of YFP expression with TNF-α (20 μg/ml) or IL-6 (20 μg/ml) in a culture with 10 mM maltodextrin (left), and statistical significance of the YFP output after 12 h incubation at 37° C. (right).

FIG. 6A shows engineering of the downstream signaling pathway for ultrasensitive performance. Strain A: YFP expression controlled by Srp promoter is repressed by SrpR; Strain B: a negative feedback loop is introduced by adding the gene for an orthogonal mf-lon protease after the YFP gene, within the same transcript controlled by the Srp promoter $P_{srp}$, to specifically degrade tagged SrpR; Strain C: a positive feedback loop is introduced into strain B by putting a second copy of the MalT gene, which encodes the maltose transcriptional activator, after the SrpR gene within the same transcript controlled by the maltose promotor $P_{Mal}$.

FIG. 6B shows dose-response curves of YFP output as a function of maltodextrin in strain A, strain B, and strain C.

FIG. 6C shows dose-response curves of YFP output as a function of FLAG tag antibody in strain A, strain B, and strain C, with 15 mM maltodextrin added in the *E. coli* culture as the compound.

FIG. 7A-D show a new biosensor based on sucrose-specific porin ScrY and sucrose-inducible promoter $P_{sacB}$.

FIG. 7A is a schematic of a biosensor design using the porin ScrY and sucrose-inducible promoter $P_{sacB}$. This design can also be modified in ways analogous to those shown for the LamB system in FIG. 6.

FIG. 7B shows an alignment of maltose-specific porin LamB of *E. coli* (SEQ ID NO: 1) and sucrose-specific porin ScrY of *Salmonella typhimurium* (SEQ ID NO: 4).

US 12,560,604 B2

5

Figure 7A:
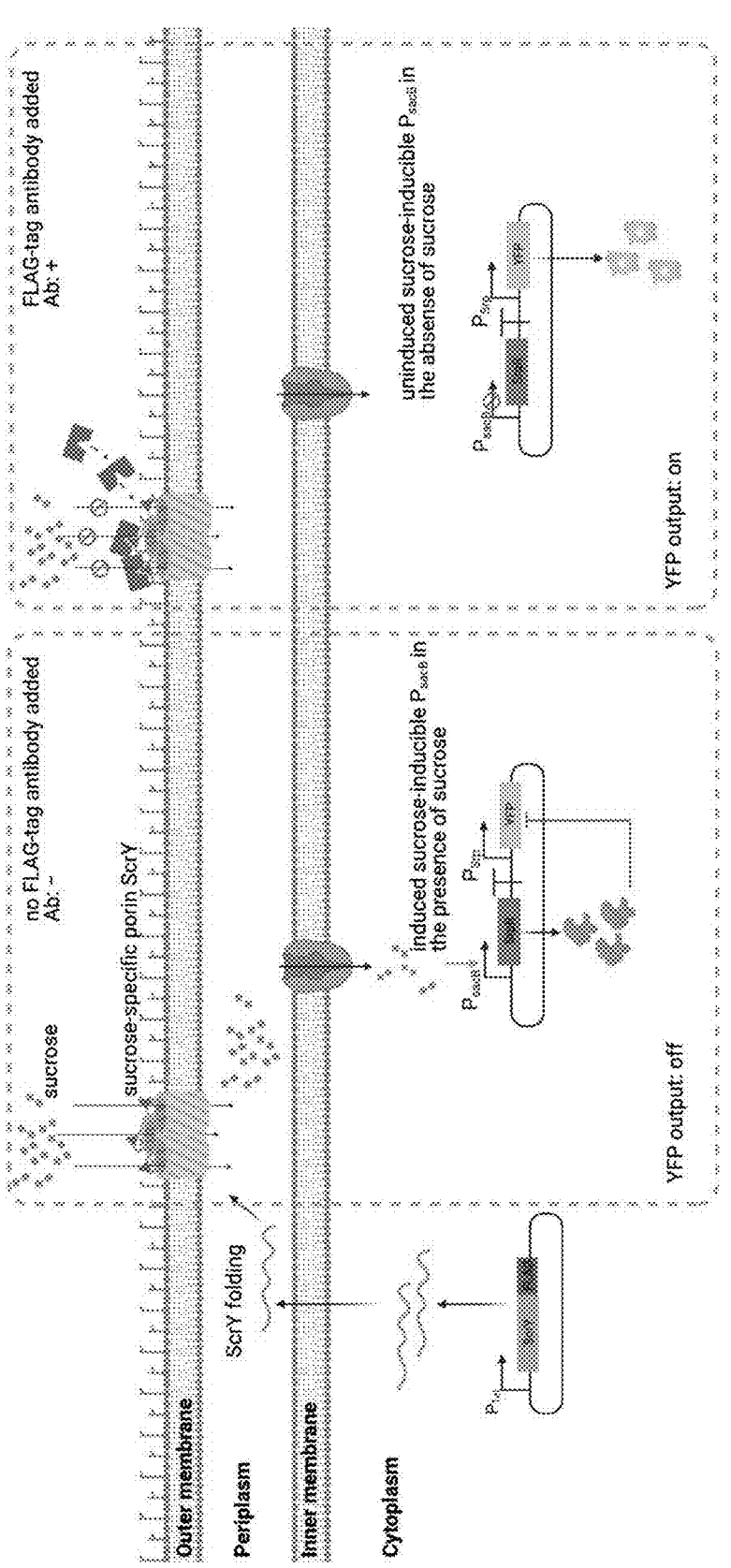
Figure 7B:
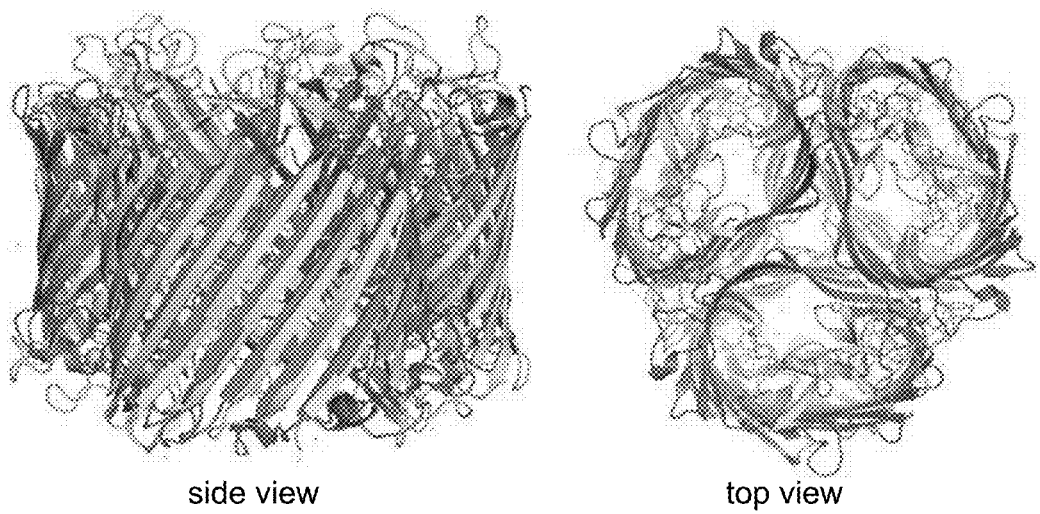
Figure 7C:
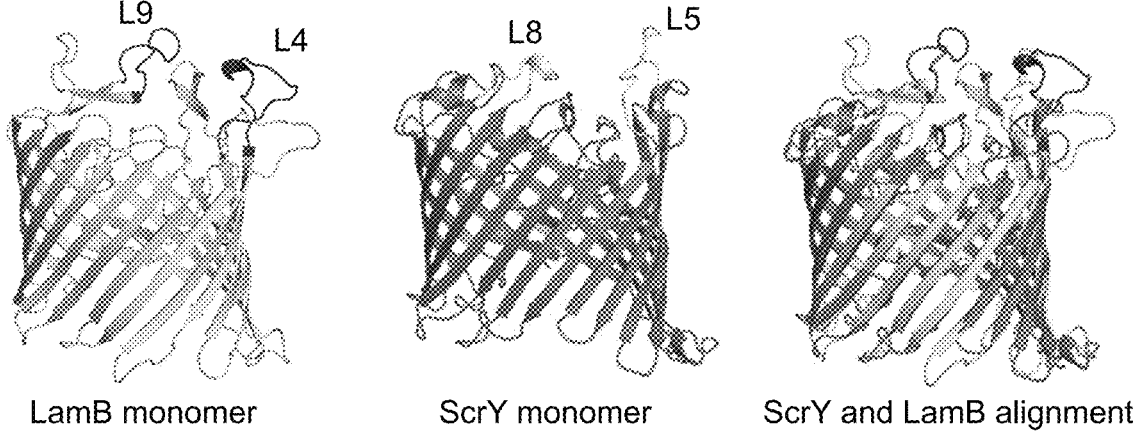

FIG. 7C shows determination of peptide insertion positions based on the structural alignment of LamB and ScrY monomers.

FIG. 7D shows the DNA sequence (SEQ ID NO: 15) of sucrose-inducible promoter P$_{sacB}$.

Figure 8A:
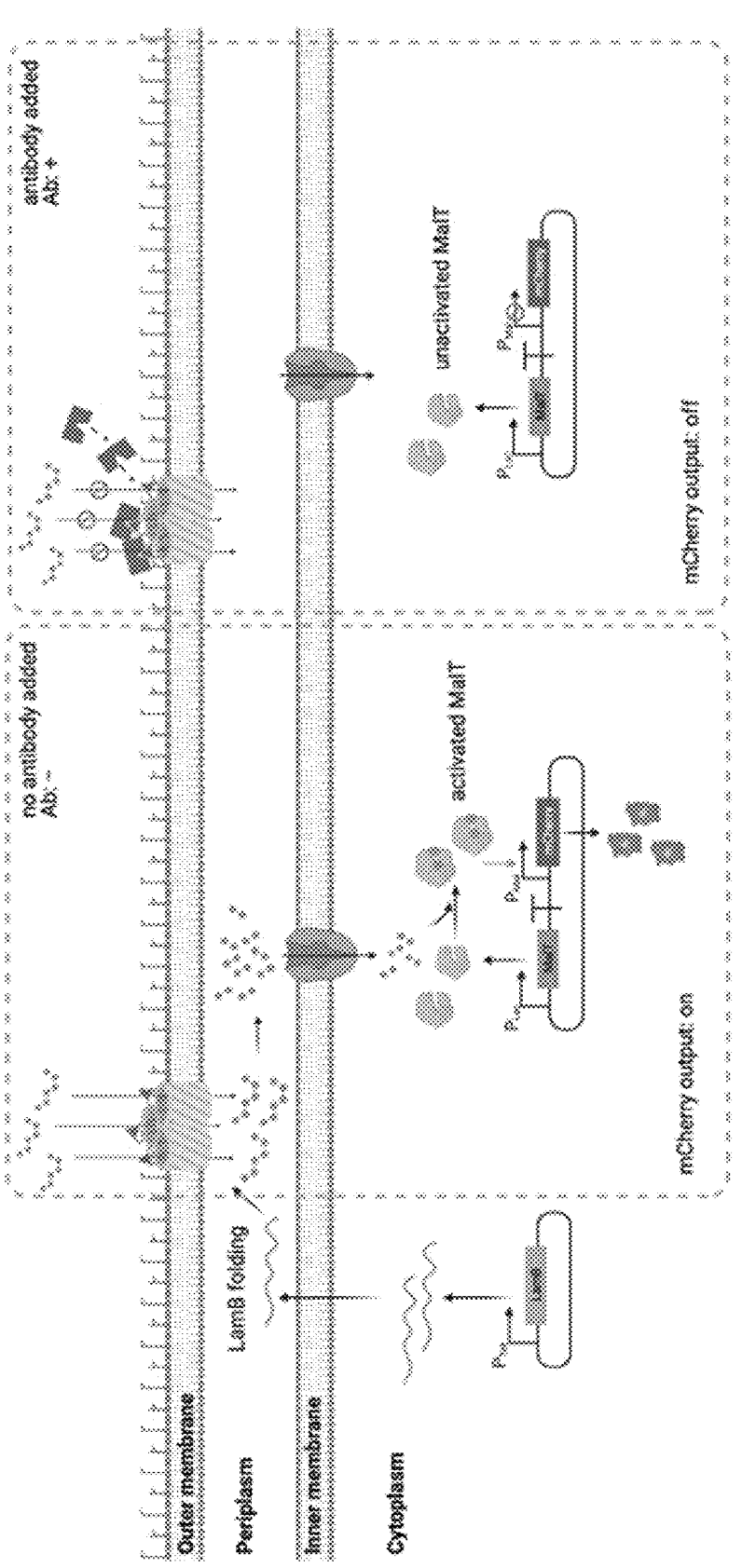
Figure 8B:
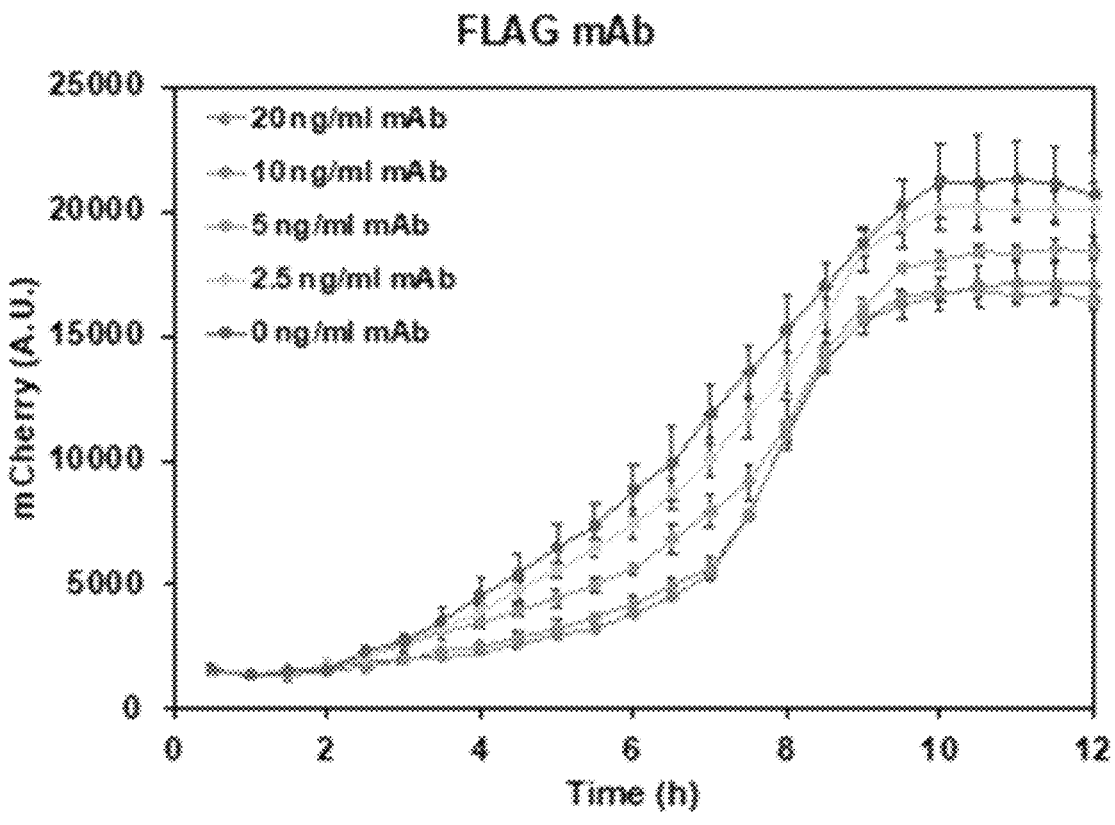
Figure 8C:
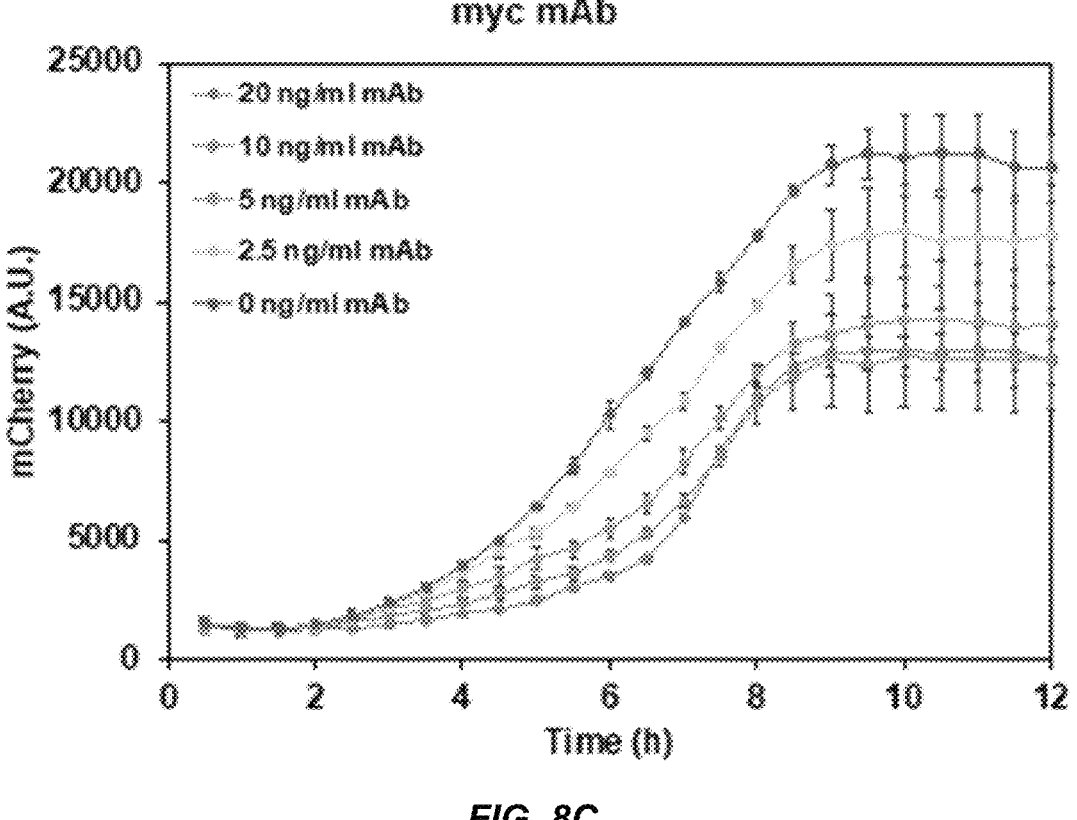
Figure 8D:
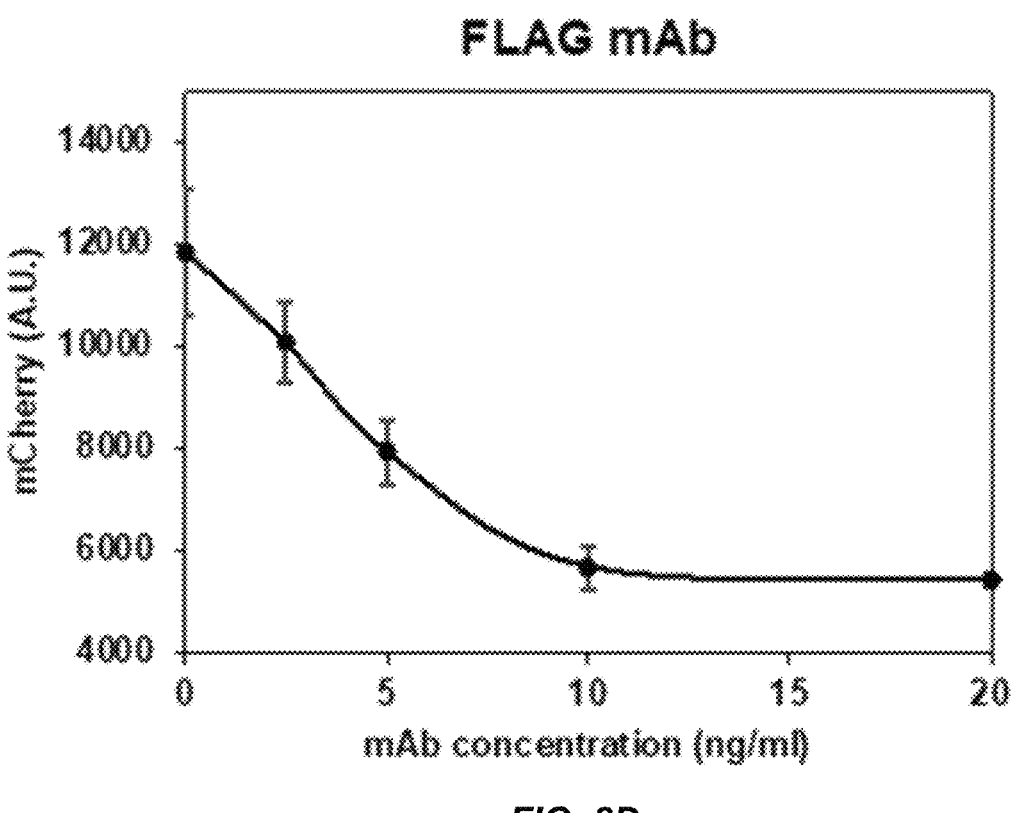
Figure 8E:
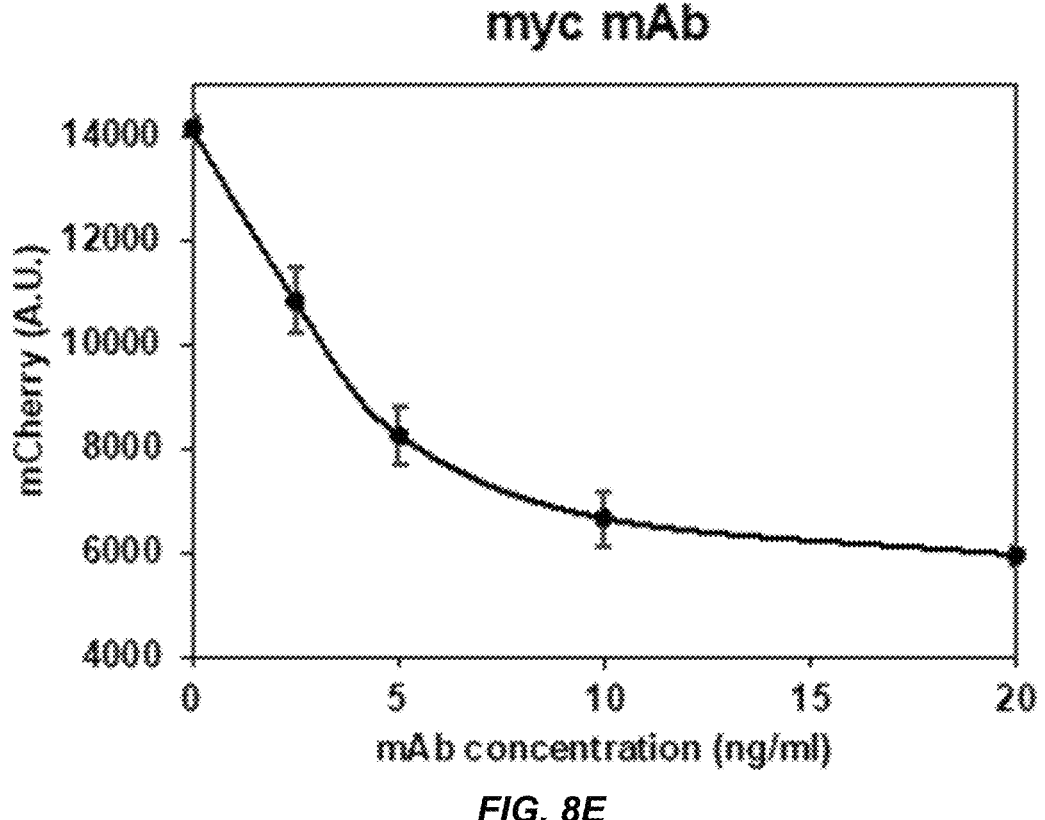

FIG. 8A, B, C, D, E show a system where extracellular presence of the compound and a target which binds to the heterologous target-specific binding peptide in the porin result in reduced expression of a protein of interest (e.g., an mCherry reporter protein). FIG. 8B shows time curves of mCherry expression with different concentrations of anti-FLAG tag antibody added in the medium. FIG. 8C shows time curves of mCherry expression with different concentrations of anti-myc tag antibody added in the medium. FIG. 8D shows a dose-response curve of mCherry expression vs. FLAG-tag antibody concentration at 7 h. FIG. 8E shows a dose-response curve of mCherry expression vs. myc-tag antibody concentration at 7 h.

Figure 9A:
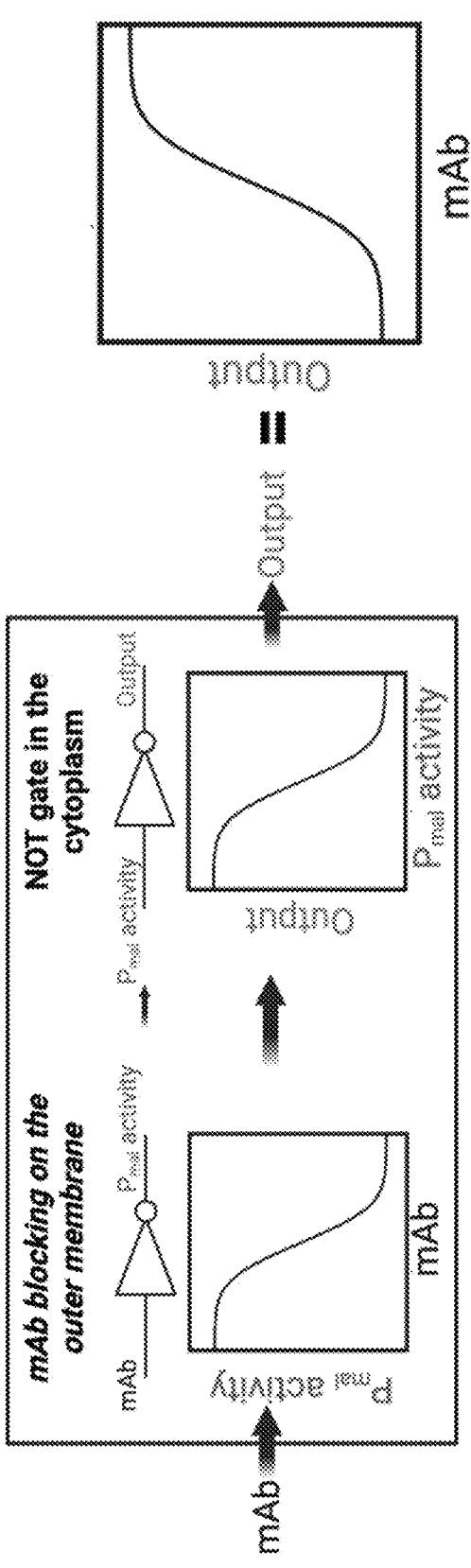
Figure 9B:
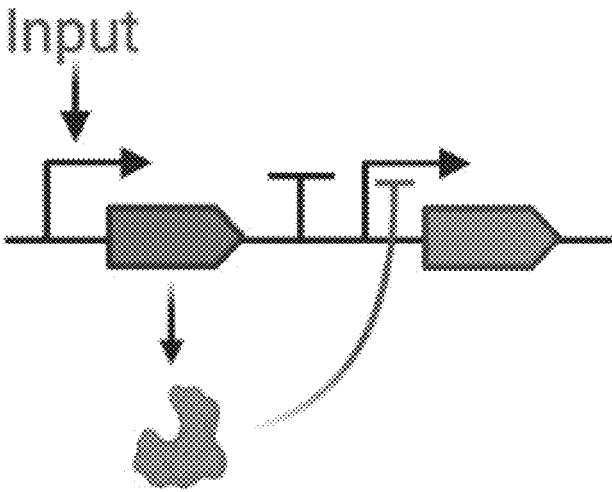
Figure 9C:
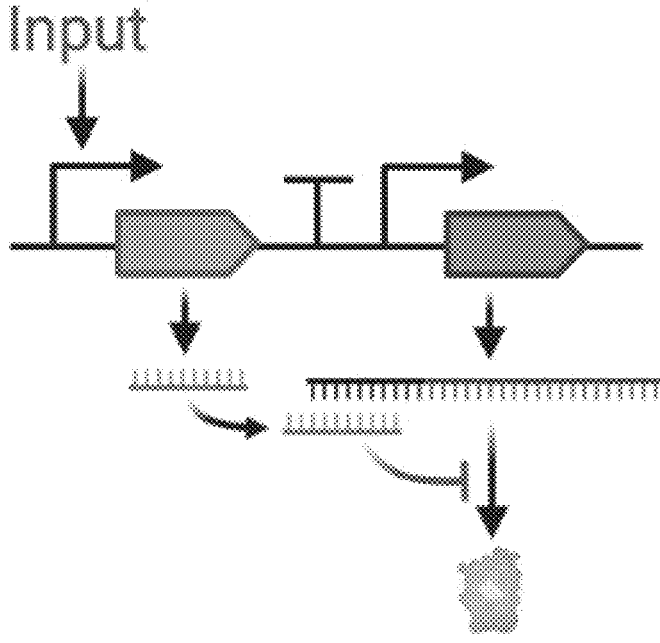
Figure 9D:
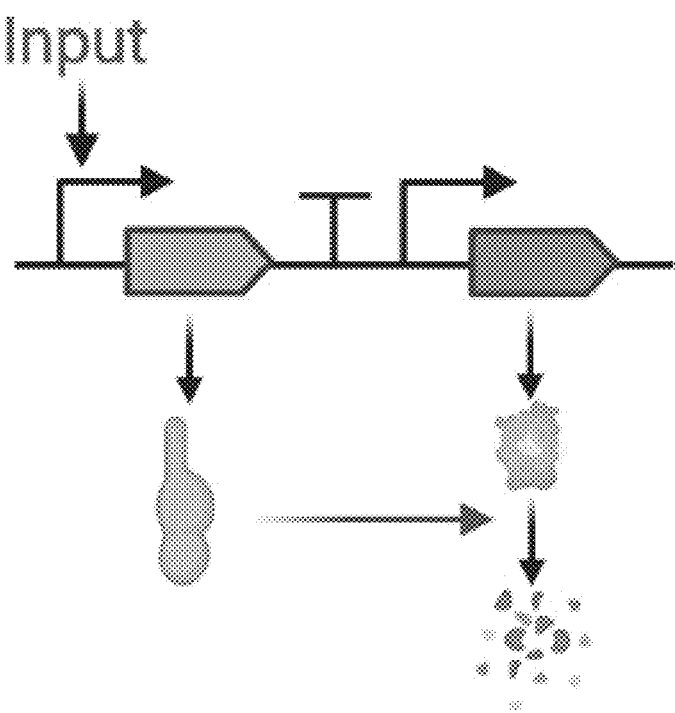

FIG. 9A, B, C, D. FIG. 9A shows how a NOT gate can be used to increase expression of a reporter in the presence of a compound and a target binding molecule that inhibits compound transport. FIG. 9B shows a NOT gate comprising a regulator protein which is a transcription repressor that can invert the signal provided by the target binding molecules and the compound to result in increased reporter expression. FIG. 9C shows a NOT gate comprising translation deactivation by a regulator RNA that is a decoy RNA that can invert the signal provided by the target binding molecules and the compound to result in increased reporter expression. FIG. 9D shows a NOT gate comprising a post-translational protein degradation system based on a regulator protein that is a protease that can invert the signal provided by the target binding molecules and the compound to result in increased reporter expression.

Figure 10:
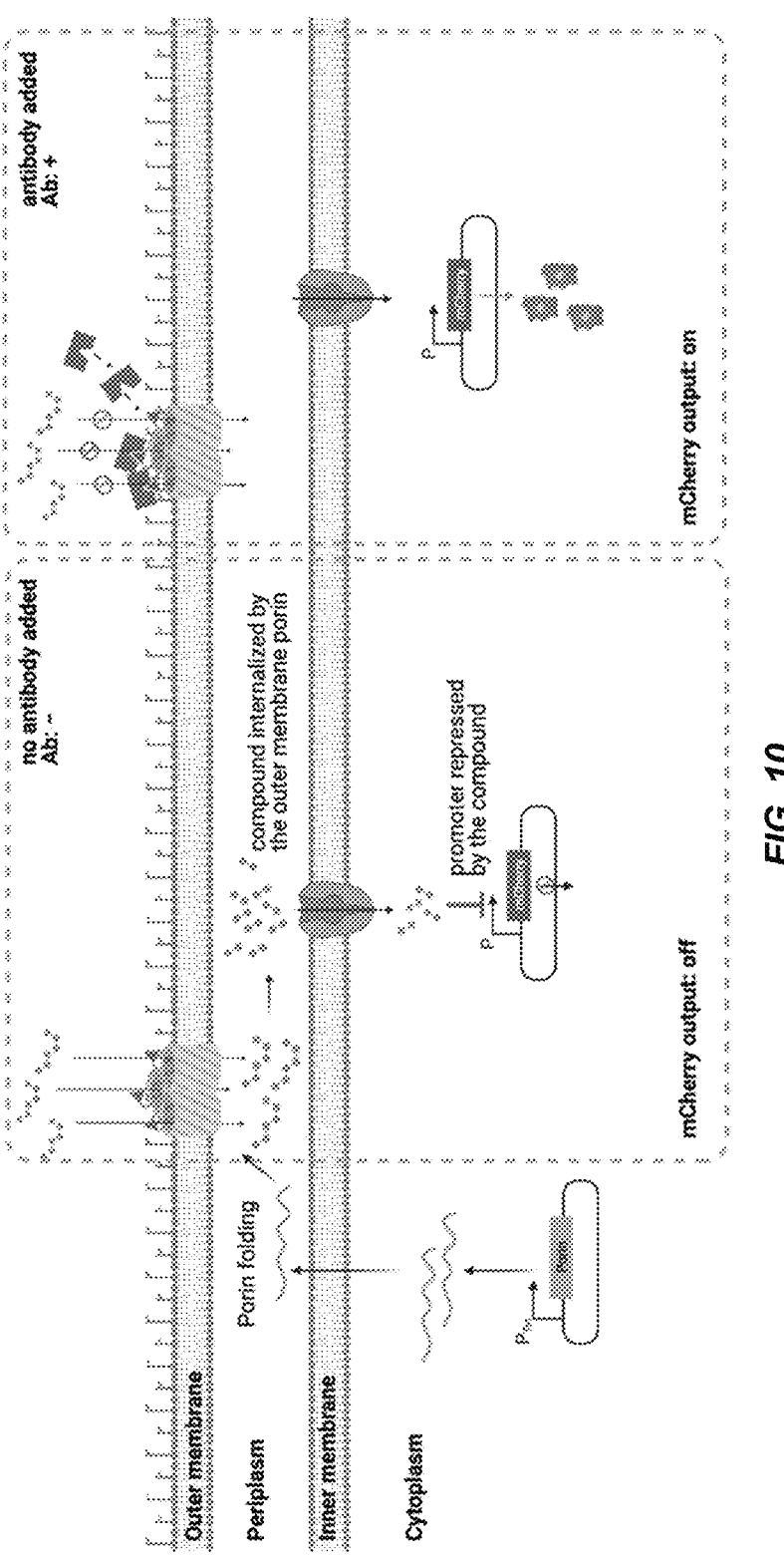

FIG. 10 shows a system where uptake of an extracellular compound represses an inducible promoter and the presence of a target which binds to the heterologous target-specific binding peptide in a porin blocks uptake of the extracellular compound, resulting in increased expression of a protein of interest (e.g., an mCherry reporter protein).

DETAILED DESCRIPTION

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "include," "includes," and "including" are to be construed as at least having the features to which they refer while not excluding any additional unspecified features.

As used herein, the term "internalize" refers to the passage of a molecule across the outer membrane into the periplasm and/or into the cytoplasm of the cell. The term "internalize" is intended to include both active and passive processes.

As used herein, the phrase "operably linked" refers to a juxtaposition wherein the components so described are in a relationship permitting them to function in their intended manner. For instance, a promoter is operably linked to a coding sequence if the promoter affects its transcription or expression.

As used herein, the terms "orthologous" or "orthologue" are used to describe genes or proteins encoded by those genes that are from different species but which have the same function (e.g., transport the same compound). Orthologous genes will typically encode proteins with some degree of sequence identity (e.g., at least 40%, 50%, 60%, 70%, 80%, 90%, or 95% sequence identity, conservation of sequence motifs, and/or conservation of structural features).

Bacterial cells comprising a first outer membrane transport protein comprising a heterologous target-specific binding peptide inserted in an extracellular portion of the membrane transport protein, wherein the membrane transport protein can internalize a compound and wherein internalization of the compound is inhibited by the presence of a target which binds to the heterologous target-specific binding peptide are disclosed. In certain embodiments, the bacterial cells comprise: (i) a first outer membrane transport protein comprising a heterologous target-specific binding peptide inserted in an extracellular portion of the membrane transport protein; (ii) a regulated promoter which is operably linked to a polynucleotide encoding a protein and/or a bioactive RNA molecule of interest, wherein said promoter is regulated by a compound, wherein the compound is internalized within the cell by the outer membrane transport protein, and wherein internalization of the compound is inhibited by the presence of a target which binds to the heterologous target-specific binding peptide. In certain embodiments, the regulated promoter is repressed when the compound is internalized within the cell (e.g., as shown in FIG. 10). In certain embodiments wherein the regulated promoter is repressed when the compound is internalized within the cell, the promoter is an XylA promoter or an AraB promoter, the compound is lactose, and the outer membrane transport protein is an OmpF porin modified by insertion of a heterologous target-specific binding peptide in an extracellular portion of OmpF. In certain embodiments, the regulated promoter is induced when the compound is internalized in the cell. In certain embodiments, the bacterial cells comprise (i) a first outer membrane transport protein comprising a heterologous target-specific binding peptide inserted in an extracellular portion of the membrane transport protein; (ii) an inducible promoter which is operably linked to a polynucleotide encoding a repressor protein, wherein said promoter is induced by a compound, and wherein the compound is internalized within the cell by the outer membrane transport protein; and (iii) a repressible promoter which is operably linked to a polynucleotide encoding a protein and/or a bioactive RNA molecule of interest, wherein said repressible promoter can be repressed by the repressor protein is disclosed. Also disclosed are systems for detection of target in a sample comprising the bacterial cells in an extracellular media comprising the target and the compound. Related methods of using the bacterial cells to inducibly express a protein and/or a bioactive RNA molecule of interest in a subject and to detect a target of interest in a sample are also disclosed.

The bacterial biosensor cells provided herein can include four components: a transport protein on the outer membrane of a gram-negative bacterial cell, an induction system in the cytoplasm, a target-specific binding peptide displayed on the outer loops of the outer membrane transport protein, and an orthogonal promoter-repressor for signal inversion in the cytoplasm. Target molecules can bind to the target-specific binding peptide inserted on the outer loops of the transport protein, thus sterically blocking transport of compounds by the transport protein. In the absence of the target, the compound is internalized by the transport protein. Once in the cytoplasm, the compound activates an inducible promoter that drives expression of a repressor protein which, in turn, inhibits the expression of the protein of interest. In the presence of the target, the internalization of the compound is inhibited so that activation of the inducible promoter is inhibited, repressor expression is reduced, and expression of the protein and/or a bioactive RNA molecule of interest is increased. Extracellular presence of the compound and a target which binds to the heterologous target-specific binding peptide results in an increase in expression of a protein and/or a bioactive RNA molecule of interest.

In certain embodiments, the bacterial biosensor cell lacks a second outer membrane transport protein which does not contain the target-specific binding peptide inserted in an extracellular portion of the membrane transport protein and which can internalize the compound within the cell. The bacterial cell may otherwise lack a functional outer membrane transport protein which can internalize the compound within the cell (e.g., a gene knockout strain). Cells lacking the second outer-membrane transport protein can be obtained by gene knockout. For example, gene knockout or replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct.

In certain embodiments, the bacterial cell is a gram-negative bacterial cell. Any gram-negative bacterial cell may be utilized including, but not limited to, a bacterial cell from the genus *Escherichia*, *Shigella*, *Salmonella*, *Campylo-* ferritins, six different iron uptake systems, adhesins, and proteases) which support its survival and successful colonization of a subject. In certain embodiments, the gram-negative bacterial cell is a member of the family Enterobacteriaceae. The gram-negative bacterial cell may be an *Escherichia coli* cell. In certain embodiments, the gram-negative bacterial cell can be an *Escherichia coli* Nissle 1917 cell. *Escherichia coli* Nissle 1917 is one of the best characterized probiotics and has GRAS (generally recognized as safe) status. *E. coli* strain Nissle 1917 lacks defined virulence factors such as alpha-hemolysin, other toxins, and mannose-resistant hemagglutinating adhesins, P-fimbrial adhesins, and the semirough lipopolysaccharide phenotype and expresses fitness factors such as microcins, ferritins, six different iron uptake systems, adhesins, and proteases, which support its survival and successful colonization of the human gut (Grozdanov et al. *J. Bacteriol.* 186(16): 5432-5441 (2004)).

The bacterial cells comprise an outer membrane transport protein. In certain embodiments, the outer membrane transport protein is a porin. The outer membrane transport protein may be substrate-specific or substrate-nonspecific. Exemplary substrate-specific porins are set forth in Table 1 and exemplary non-specific porins are set forth in Table 2. In certain embodiments, the outer membrane transport protein is a substrate specific transporter. Non-specific porins are generally responsible for the transport of essential nutrients such as carbohydrates and amino acids, so blocking the channel may interfere with cell growth. Non-specific porins are also important to the integrity and structure of the outer membrane, so changing their expression levels and inserting peptides in their extracellular loops are more likely to affect cell viability.

TABLE 1

| Porin protein name | Host | Transported compounds | Peptide insertion | Inductive | Uniprot Protein ID | PDB ID |
|---|---|---|---|---|---|---|
| LamB | *E. coli* | Maltose/maltodextrin | Shown in Examples | Yes | P02943 | 1MAL |
| LamB mutant (R109A, Y118A) | *E. coli* | Sucrose (LamB repurposed to transport sucrose through protein engineering) | Shown in Examples | Yes | P02943 | 1MAL |
| ScrY | *E .coli, Salmonella* | Sucrose | Very similar structure to LamB | Yes | Q6EVL3 | 1A0S |
| BtuB | *E. coli* | Cobalamin (Vitamin B12) | Yes | Yes | P06129 | 1NQG |
| FhuA | *E. coli* | Ferrochrome | Yes | Yes | P06971 | 2FCP |
| FepA | *E. coli* | Iron(III)-enterobactin complex | Yes | Yes | P05825 | 1FEP |
| TsX | *E. coli* | Nucleosides and deoxynucleosides | Feasible based on the structure | Yes | P0A927 | 1TLY |
| YddB | *E. coli* | Novobiocin | Feasible based on the structure | Yes for mammalian cells | P31827 | 6OFR | bacter, *Neisseria*, *Haemophilus*, *Aeromonas*, *Francisella*, *Yersinia*, *Klebsiella*, *Bordetella*, *Legionella*, *Corynebacteria*, *Citrobacter*, *Chlamydia*, *Brucella*, *Pseudomonas*, *Helicobacter*, or *Vibrio*. In certain embodiments, the bacterial cell is an attenuated bacterial cell that is deficient in in one of more virulence factors (e.g., alpha-hemolysin, other toxins, and mannose-resistant hemagglutinating adhesins, P-fimbrial adhesins, and the semirough lipopolysaccharide phenotype) and/or expresses fitness factors (e.g., microcins,

TABLE 2

| Porin protein name | Host | Transported compounds | Peptide insertion | Inductive | Uniprot Protein ID | PDB ID |
|---|---|---|---|---|---|---|
| OmpA | *E. coli* | Non-specific porin, passively | Yes, most well studied | NA | P0A910 | 1G90 |

TABLE 2-continued

| Porin protein name | Host | Transported compounds | Peptide insertion | Inductive | Uniprot Protein ID | PDB ID |
|---|---|---|---|---|---|---|
| | | transports many small molecules, some of which could be inducers | for peptide bacterial display | | | |
| OmpC | E. coli | Non-specific porin for many compounds | Yes | NA | P06996 | 2XG6 |
| OmpF | E. coli | Non-specific porin for many compounds | Yes | NA | P02931 | 2ZFG |
| PhoE | E. coli | Non-specific porin for ions | Yes | NA | P02932 | 1PHO |
| OmpX | E. coli | None | Yes, most well studied | NA | P0A917 | 1Q9G |

The outer membrane transport protein may be, for example, LamB (Maltoporin), ScrY (Sucrose porin), BtuB (Vitamin B12 transporter), FhuA (Ferrichrome outer membrane transporter), FepA (Ferrienterobactin receptor), TsX (Nucleoside-specific channel-forming protein Tsx), YddB, OmpA (Outer membrane protein A), OmpC (Outer membrane porin C), OmpF (Outer membrane porin F), PhoE (Outer membrane porin PhoE), or OmpX (Outer membrane protein X). In certain embodiments, the outer membrane transport protein can comprise the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or the portion thereof encoding the mature protein. The amino acid sequences are numbered herein from the N-terminus to the C-terminus with the signal peptide present. The signal peptide is not present in the mature protein after processing. In certain embodiments, a heterologous signal peptide encoding sequence can be operably linked to a sequence encoding the mature outer membrane transport protein.

In certain embodiments, the outer membrane transport protein is a LamB porin. The amino acid sequence of E. coli LamB is provided as SEQ ID NO: 1, wherein residues 1-25 is a signal peptide not present in the mature protein. The LamB porin may comprise the amino acid sequence of SEQ ID NO: 1 or SEQ ID NO: 2, or an amino acid sequence having at least 70%, at least 75%, at least 80%, at least 90%, at least 95%, at least 98%, or at least 99% sequence identity thereto.

Also provided herein are orthologue sequences of any of the outer membrane transport proteins provided herein. Such orthologue sequences include sequences having at least 70%, at least 75%, at least 80%, at least 90%, at least 95%, at least 98%, or at least 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14.

The compound will depend upon the specific outer membrane transport protein employed in the biosensor system. In certain embodiments, the compound is membrane-impermeable (e.g., require an outer membrane transport protein to cross the cell membrane). In certain embodiments, the compound is a hydrophilic compound. The compound may be a sugar (e.g., maltose, maltodextrin, sucrose), an amino acid, a nucleoside (e.g., adenosine, guanosine, 5-methyluridine, uridine, cytidine), a deoxynucleoside (e.g., deoxyadenosine, deoxyguanosine, thymidine, deoxyuridine, deoxycytidine), a siderophore (e.g., ferrochrome, iron(III)-enterobactin complex), a cobalamin (e.g., vitamin B12), or an antibiotic (e.g., novobiocin). In certain embodiments, the compound is maltose or maltodextrin.

The outer membrane transport protein can comprise a heterologous target-specific binding peptide inserted in an extracellular portion of the outer membrane transport protein. In certain embodiments, the first outer membrane transport protein comprises two or more heterologous target-specific binding peptides inserted in an extracellular portion of the membrane transport protein. The two or more target-specific binding peptides may bind the same target or the two or more target-specific binding peptides may bind distinct targets.

The heterologous target-specific binding peptide will depend upon the specific target selected. The target can, in principle, be anything if there is a peptide that binds specifically to it. In certain embodiments, the target comprises a protein, a carbohydrate, a nucleic acid, or combination thereof. Some examples of target-specific binding peptide and target pairs include antigen-antibody, receptor-hormone, receptor-ligand, lectin-carbohydrate, avidin-biotin, and virus-receptor interactions. In certain embodiments, the biosensor is used as a diagnostic tool to detect biological target molecules or inorganic target molecules.

Non-limiting examples of heterologous target-specific binding peptides are set forth in Table 3.

TABLE 3

| Name | Heterologous target-specific binding peptide amino acid sequence | Target |
|---|---|---|
| FLAG-tag | DYKDDDDK (SEQ ID NO: 16) | FLAG-tag antibody |
| myc-tag | EQKLISEED (SEQ ID NO: 17) | myc-tag antibody |
| KCF18 | KCRKEMFKQKLPYSTVYF (SEQ ID NO: 18) | human TNF-α, human IL-6 |

In certain embodiments, the heterologous target-specific binding peptide can have a length from about 5 amino acids to about 100 amino acids, e.g., from about 5 amino acids to about 75 amino acids, from about 5 amino acids to about 50 amino acids, from about 5 amino acids to about 20 amino acids, from about 5 amino acids to about 10 amino acids, from about 10 amino acids to about 75 amino acids, from about 10 amino acids to about 50 amino acids, or from about 10 amino acids to about 20 amino acids.

The bacterial biosensor cell can express a protein of interest and/or bioactive RNA molecule of interest in the presence of the target and the compound. The protein of interest may be any type of protein, including, for example, enzymes (e.g., oxidoreductases, transferases, hydrolases, lyases, isomerases, or ligases); transcriptional activators, transcriptional repressors, genome editing proteins, Cas proteins, TALENs, nucleases, binding proteins (e.g., ligands, receptors, antibodies, antibody fragments; nucleic acid binding proteins, etc.); structural proteins; therapeutic proteins (e.g., tumor suppressor proteins, therapeutic enzymes, growth factors, growth factor receptors, transcription factors, proteases, etc.); and fluorescent or luminescent proteins. Bioactive RNA molecules of interest include guide RNA molecules (e.g., for use with a Cas nuclease), artificial miRNAs, and ribozymes.

In certain embodiments, the protein of interest is a reporter protein. The term "reporter gene" refers to a nucleic acid having a sequence encoding a gene product that is easily and quantifiably assayed. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene. Any suitable reporter protein can be used.

In certain embodiments, the protein of interest is an effector protein. The term "effector protein" refers to a protein that modulates a biological function (e.g., a biologically active protein).

In certain embodiments, the bacterial cell comprising a membrane transport protein containing the target-specific binding peptide (e.g., a LamB protein with the target-specific binding peptide) will further comprise a protein or bioactive RNA of interest which is activated by the presence of the compound (e.g., as shown in FIG. 8A). Expression of the protein or bioactive RNA of interest can be inhibited by the presence of the target (e.g., as shown in FIG. 8A).

In certain embodiments, the bacterial cell comprising a membrane transport protein containing the target-specific binding peptide (e.g., a LamB protein with the target-specific binding peptide) will further comprise a regulator protein or regulator RNA of interest which inhibits expression of the protein or bioactive RNA interest in the presence of the compound and absence of the target (e.g., as shown in FIG. 9A, B, C, or D). Expression of the protein or bioactive RNA of interest can be increased by the presence of the target in these systems (e.g., as shown in FIGS. 9A, B, C, and D). Systems that comprise a regulator protein or regulator RNA that inhibits expression of another gene encoding a protein or RNA molecule of interest are referred to as "NOT gates." NOT gates that can be adapted for use with the bacterial cells and methods provided herein include those based on transcription repression (Stanton et al. 2014, doi: 10.1038/nchembio.1411), on translation deactivation by decoy RNA (Green et al. 2017, doi:10.1038/nature23271), or on post-translational protein degradation (Fernandez-Rodriguez and Voigt, 2016, doi:10.1093/nar/gkw537).

The bacterial cell may include further modifications to increase sensitivity of detection. In certain embodiments, the repressible promoter or another repressible promoter under control of the repressor is also operably linked to a polynucleotide encoding a protein that can inactivate the repressor. The protein that can inactivate the repressor may be, for example, a protease or may bind the repressor.

Methods provided herein can be used to inducibly express a protein and/or a bioactive RNA molecule of interest in a subject. The methods comprise administering a bacterial cell disclosed herein to the subject. The protein and/or a bioactive RNA molecule of interest is expressed in the extracellular presence of the compound and a target which binds to the heterologous target-specific binding peptide. In certain embodiments, the methods further comprise administering the inductive compound to the subject.

The bacterial cells may be administered in the form of a pharmaceutical composition. As used herein a "pharmaceutical composition" refers to a preparation of the bacterial cells of the disclosure with other components such as a pharmaceutically acceptable carrier. In certain embodiments, the pharmaceutical composition can include the bacterial cells and the compound (e.g., maltodextrin).

As used herein, the term "pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition. Pharmaceutically acceptable carriers may be chosen to permit oral administration or administration by any other known route.

Pharmaceutical compositions comprising the bacterial cells can be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the disclosed bacterial cells, and may be prepared by methods of pharmacy well known to those skilled in the art. See generally, Remington: The Science and Practice of Pharmacy, 21st Ed., Lippincott, Williams, and Wilkins, Philadelphia, Pa. (2005).

In addition to the oral dosing, noted above, the compositions of the present invention may be administered by any suitable route, in the form of a pharmaceutical composition adapted to such a route, and in a dose effective for the purpose intended.

As used herein, a "subject" refers to any organism upon which embodiments of the disclosure may be used or administered, e.g., for experimental, diagnostic, prophylactic, and/or therapeutic purposes. The subject may include an animal, a mammal, a human, a non-human animal, a livestock animal, or a companion animal. The term "subject" is intended to include human and non-human animals, for example, vertebrates, large animals, and primates. In certain embodiments, the subject is a mammalian subject, and in particular embodiments, the subject is a human subject. The term "non-human animals" of the disclosure includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

Methods provided herein can be used to detect a target of interest in a sample. The methods comprise (i) contacting a bacterial cell disclosed herein with the sample and the compound, wherein the protein of interest is a reporter protein; and (ii) detecting the reporter protein to determine the presence of the target in the sample, wherein expression of the reporter protein is increased in samples containing the target in comparison to expression of the reporter protein in a control bacterial cell contacted with the compound and a control sample lacking or deficient in the target.

"Sample" is to be used in the broad sense and is intended to include a wide range of environmental sources and biological materials. Non-limiting examples of environmental samples include food, water, soil, or waste. Exemplary biological samples include, among others, whole blood; red blood cells; white blood cells; hair; swabs (e.g., buccal swabs, throat swabs, vaginal swabs, urethral swabs, cervical swabs, throat swabs, rectal swabs, lesion swabs, abscess swabs, nasopharyngeal swabs, and the like); urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, biopsy material, and the like. Tissue culture cells, including explanted material, primary cells, secondary cell lines, and the like, as well as lysates, extracts, or materials obtained from any cells, are also within the meaning of the term biological sample as used herein. The sample can be obtained from an in vitro source (e.g., a suspension of cells from laboratory cells grown in culture) or from an in vivo source (e.g., a mammalian subject, a human subject, etc.).

In some embodiments, the sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the sample is obtained from an in vivo source and can include samples obtained from tissues (e.g., cell suspension from a tissue biopsy, cell suspension from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to evaluation. In vivo sources include living multi-cellular organisms and can yield non-diagnostic or diagnostic samples.

The samples can be used without further processing or processed according to various methods typically used to prepare samples. For instance, samples containing cells or bacteria may be subjected to physical conditions to disrupt the cells and liberate their contents. Non-limiting examples of such techniques include, among others, sonication, pressure, heat, irradiation, and mechanical shearing. Samples may also be treated with detergents, denaturing agents, chaotropic salts, and enzymes such as lysozymes, nucleases, glycosidases, etc. Samples may be subjected to further manipulation, such as filtration, chromatography, precipitation, solvent extraction, and derivatization.

Samples can be obtained from a variety of different types of subjects.

EMBODIMENTS

The following numbered embodiments also form part of the present disclosure:

1. A bacterial cell comprising: (i) a first outer membrane transport protein comprising a heterologous target-specific binding peptide inserted in an extracellular portion of the membrane transport protein; (ii) an inducible promoter which is operably linked to a polynucleotide encoding a repressor protein, wherein said promoter is induced by a compound, and wherein the compound is internalized within the cell by the outer membrane transport protein; and (iii) a repressible promoter which is operably linked to a polynucleotide encoding a protein of interest and/or a bioactive RNA molecule, wherein said repressible promoter can be repressed by the repressor protein.

2. The bacterial cell of embodiment 1 or 2, wherein the bacterial cell lacks a second outer membrane transport protein which does not contain the target-specific binding peptide inserted in an extracellular portion of the membrane transport protein and which can internalize the compound within the cell.

3. The bacterial cell of any one of embodiments 1-2, wherein the first outer membrane transport protein comprises two or more heterologous target-specific binding peptides inserted in an extracellular portion of the membrane transport protein, optionally wherein the target-specific binding peptides bind the same target or optionally wherein the target-specific binding peptides bind distinct targets.

4. The bacterial cell of any one of embodiments 1-3, wherein the compound is a hydrophilic compound.

5. The bacterial cell of any one of embodiments 1-4, wherein the compound is a sugar, an amino acid, a nucleoside, a deoxynucleoside, a siderophore, a cobalamin, or an antibiotic.

6. The bacterial cell of any one of embodiments 1-5, wherein the compound is maltose or maltodextrin.

7. The bacterial cell of any one of embodiments 1-6, wherein the protein of interest comprises a reporter or an effector protein or wherein the bioactive RNA molecule comprises a guide RNA molecule, an artificial miRNA, or ribozyme.

8. The bacterial cell of any one of embodiments 1-7, wherein the cell is a gram-negative bacterial cell and optionally wherein the gram-negative bacterial cell is a member of the family Enterobacteriaceae.

9. The bacterial cell of any one of embodiments 1-8, wherein the cell is an *Escherichia coli* cell, or optionally an *Escherichia coli* Nissle 1917 cell.

10. The bacterial cell of any one of embodiments 1-8, wherein the target comprises a protein, a carbohydrate, or a nucleic acid.

11. The bacterial cell of any one of embodiments 1-10, wherein the outer membrane transport protein is a porin.

12. The bacterial cell of any one of embodiments 1-11, wherein the outer membrane transport protein is a LamB porin.

13. The bacterial cell of any one of embodiments 1-12, wherein the LamB porin comprises the amino acid sequence of SEQ ID NO: 1 or 2, or an amino acid sequence having at least 70%, at least 80%, least 90%, or at least 95% sequence identity thereto.

14. The bacterial cell of any one of embodiments 1-13, wherein the repressible promoter or another repressible promoter under control of the repressor is also operably linked to a polynucleotide encoding a protein which can inactivate the repressor.

15. The bacterial cell of any one of embodiments 1-14, wherein the protein which can inactivate the repressor comprises a protease.

16. The bacterial cell of any one of embodiments 1-14, wherein the protein which can inactivate the repressor binds the repressor.

17. The bacterial cell of any one of embodiments 1-16, wherein internalization of the compound is inhibited by the presence of a target which binds to the heterologous target-specific binding peptide.

18. The bacterial cell of any one of embodiments 1-17, wherein extracellular presence of the compound and a target which binds to the heterologous target-specific binding peptide results in an increase in expression of the protein of interest or the bioactive RNA molecule in comparison to expression of the protein of interest or the bioactive RNA molecule in the extracellular presence of the compound when the target is present at lower concentrations or absent.

19. A system for detection of target in a sample comprising the bacterial cell of any one of embodiments 1-18 in an extracellular media comprising the target and the compound.

20. A method of inducibly expressing a protein of interest and/or a bioactive RNA molecule in a subject, the method comprising: administering the bacterial cell of any one of embodiments 1-18 to the subject, wherein the protein of interest and/or the bioactive RNA molecule is expressed in the extracellular presence of the compound and a target which binds to the heterologous target-specific binding peptide.

21. The method of embodiment 20 further comprising administering the compound to the subject, optionally wherein the bacterial cell and the compound are co-administered.

22. The method of embodiment 20 or 21, wherein the subject is a human, a livestock animal, or companion animal.

23. A method of detecting a target of interest in a sample, the method comprising: (i) contacting the bacterial cell of any one of embodiments 1-18 with the sample and the compound, wherein the protein of interest comprises a reporter protein; and (ii) detecting the reporter protein to determine the presence of the target in the sample, wherein expression of the reporter protein is increased in samples containing the target in comparison to expression of the reporter protein in a control bacterial cell contacted with the compound and a control sample lacking or deficient in the target.

24. A bacterial cell comprising: (i) a first outer membrane transport protein comprising a heterologous target-specific binding peptide inserted in an extracellular portion of the membrane transport protein; (ii) an inducible promoter which is operably linked to a polynucleotide encoding a protein and/or a bioactive RNA molecule of interest, wherein said promoter is induced by a compound, and wherein the compound is internalized within the cell by the outer membrane transport protein.

25. The bacterial cell of embodiment 24, wherein the bacterial cell lacks a second outer membrane transport protein which does not contain the target-specific binding peptide inserted in an extracellular portion of the membrane transport protein and which can internalize the compound within the cell.

26. The bacterial cell of embodiment 24 or 25, wherein the first outer membrane transport protein comprises two or more heterologous target-specific binding peptides inserted in an extracellular portion of the membrane transport protein, optionally wherein the target-specific binding peptides bind the same target or optionally wherein the target-specific binding peptides bind distinct targets.

27. The bacterial cell of embodiment 24, 25, or 26, wherein the compound is a hydrophilic compound.

28. The bacterial cell of any one of embodiments 24-27, wherein the compound is a sugar, an amino acid, a nucleoside, a deoxynucleoside, a siderophore, a cobalamin, or an antibiotic.

29. The bacterial cell of any one of embodiments 24-28, wherein the compound is maltose or maltodextrin.

30. The bacterial cell of any one of embodiments 24-29, wherein the protein of interest comprises a reporter or an effector protein.

31. The bacterial cell of embodiment 24 or 30, wherein the cell is a gram-negative bacterial cell and optionally wherein the gram-negative bacterial cell is a member of the family Enterobacteriaceae.

32. The bacterial cell of embodiment 31, wherein the cell is an *Escherichia coli* cell, or optionally an *Escherichia coli* Nissle 1917 cell.

33. The bacterial cell of any one of embodiments 24-32, wherein the target comprises a protein, a carbohydrate, or a nucleic acid.

34. The bacterial cell of any one of embodiments 24-33, wherein the outer membrane transport protein is a porin.

35. The bacterial cell of embodiment 34, wherein the outer membrane transport protein is a LamB porin.

36. The bacterial cell of embodiment 35, wherein the LamB porin comprises or includes the amino acid sequence of SEQ ID NO: 1 or 2, or an amino acid sequence having at least 70%, at least 80%, at least 90%, or at least 95% sequence identity thereto.

37. The bacterial cell of any one of embodiments 24-36, wherein internalization of the compound is inhibited by the presence of a target which binds to the heterologous target-specific binding peptide.

38. The bacterial cell of any one of embodiments 24-37, wherein extracellular presence of the compound and a target which binds to the heterologous target-specific binding peptide results in a decrease in expression of the protein of interest or the bioactive RNA molecule in comparison to expression of the protein of interest or the bioactive RNA molecule in the extracellular presence of the compound when the target is present at lower concentrations or absent.

39. A system for decreasing expression of a protein of interest and/or a bioactive RNA molecule comprising the bacterial cell of any one of embodiments 24-28, the target, and the compound, wherein the bacterial cell, the target, and the compound are in an extracellular media or are in a subject.

40. A method of controlling expression of a protein of interest and/or a bioactive RNA molecule in a subject, the method comprising: (i) administering the bacterial cell of any one of embodiments 24-38 to the subject, wherein the protein of interest and/or the bioactive RNA molecule is expressed in the extracellular presence of the compound; and (ii) administering a target which binds to the heterologous target-specific binding peptide, thereby reducing expression of the protein of interest and/or the bioactive RNA molecule in comparison to a control subject lacking the bacterial cell or in comparison to the subject before administration of the bacterial cell.

41. The method of embodiment 40, wherein the compound is present in the subject at the time of administering the bacterial cell and wherein the target which binds to the heterologous target-specific binding peptide is administered after accumulation of the protein of interest and/or the bioactive RNA molecule in the subject in comparison to a control subject lacking the bacterial cell or in comparison to the subject before administration of the bacterial cell.

42. The method of embodiment 40 or 41, further comprising administering the compound to the subject.

43. The method of embodiment 42, wherein said administering of the compound is performed either before administering the bacterial cell, concurrent with administration of the bacterial cell, or after administration of the bacterial cell.

44. The method of embodiment 40, wherein the subject is a human, a livestock animal, or companion animal.

45. A method of detecting a target of interest in a sample, the method comprising: (i) contacting the bacterial cell of any one of embodiments 24-37 with the sample and the compound, wherein the protein of interest comprises a reporter protein; and (ii) detecting the reporter protein to determine the presence of the target in the sample, wherein expression of the reporter protein is decreased in samples containing the target in comparison to expression of the reporter protein in a control bacterial cell contacted with the compound and a control sample lacking or deficient in the target.

46. A bacterial cell comprising: (i) a first outer membrane transport protein comprising a heterologous target-specific binding peptide inserted in an extracellular portion of the membrane transport protein; (ii) a first promoter which is inducible and operably linked to a polynucleotide encoding a regulator protein and/or a regulator RNA molecule, wherein said promoter is induced by a compound, and wherein the compound is internalized within the cell by the outer membrane transport protein; and (iii) a second promoter which is operably linked to a protein and/or a bioactive RNA molecule of interest, wherein the second promoter is repressed by the regulator protein or wherein expression of the protein of interest is inhibited by the regulator protein and/or wherein the expression of the protein of interest is inhibited by the regulator RNA molecule.

47. The bacterial cell of embodiment 46, wherein the regulator protein is a transcriptional repressor which represses transcription of the second promoter, optionally wherein the repressor is an *E. coli* Lad repressor or TrpR repressor.

48 The bacterial cell of embodiment 46 or 47, wherein the regulator RNA molecule decreases translation of the protein of interest or decreases accumulation of mRNA encoding the protein and/or a bioactive RNA molecule of interest, optionally wherein the regulator RNA is a decoy RNA molecule, optionally wherein the decoy RNA is an siRNA which hybridizes to the mRNA encoding the protein and/or a bioactive RNA molecule of interest.

49. The bacterial cell of embodiment 46 or 47, wherein the regulator protein is a protease that degrades the protein of interest, optionally wherein the protease is a potyvirus protease.

50. The bacterial cell of any one of embodiments 46-49, wherein the bacterial cell lacks a second outer membrane transport protein which does not contain the target-specific binding peptide inserted in an extracellular portion of the membrane transport protein and which can internalize the compound within the cell.

51. The bacterial cell of any one of embodiments 46-50, wherein the first outer membrane transport protein comprises two or more heterologous target-specific binding peptides inserted in an extracellular portion of the membrane transport protein, optionally wherein the target-specific binding peptides bind the same target or optionally wherein the target-specific binding peptides bind distinct targets.

52. The bacterial cell of any one of embodiments 46-51, wherein the compound is a hydrophilic compound.

53. The bacterial cell of embodiment 52, wherein the compound is a sugar, an amino acid, a nucleoside, a deoxynucleoside, a siderophore, a cobalamin, or an antibiotic.

54. The bacterial cell of embodiment 53, wherein the compound is maltose or maltodextrin.

55. The bacterial cell of any one of embodiments 46-54, wherein the protein of interest comprises a reporter or an effector protein.

56. The bacterial cell of any one of embodiments 46-55, wherein the cell is a gram-negative bacterial cell and optionally wherein the gram-negative bacterial cell is a member of the family Enterobacteriaceae.

57. The bacterial cell of embodiment 56, wherein the cell is an *Escherichia coli* cell, or optionally an *Escherichia coli* Nissle 1917 cell.

58. The bacterial cell of any one of embodiments 46-57, wherein the target comprises a protein, a carbohydrate, or a nucleic acid.

59. The bacterial cell of any one of embodiments 46-58, wherein the outer membrane transport protein is a porin.

60. The bacterial cell of embodiment 59, wherein the outer membrane transport protein is a LamB porin.

61. The bacterial cell of embodiment 60, wherein the LamB porin comprises or includes the amino acid sequence of SEQ ID NO: 1 or 2, or an amino acid sequence having at least 70%, at least 80%, least 90%, or at least 95% sequence identity thereto.

62. The bacterial cell of any one of embodiments 46-61, wherein internalization of the compound is inhibited by the presence of a target which binds to the heterologous target-specific binding peptide.

63. A system for increasing expression of a protein of interest and/or a bioactive RNA molecule comprising the bacterial cell of any one of embodiments 46-62, the target, and the compound, wherein the bacterial cell, the target, and the compound are in an extracellular media or are in a subject.

64. A method of controlling expression of a protein of interest and/or a bioactive RNA molecule in a subject, the method comprising: (i) administering the bacterial cell of any one of embodiments 46-62 to the subject, wherein the expression of the protein of interest and/or the bioactive RNA molecule is increased in the extracellular presence of the compound; and (ii) administering a target which binds to the heterologous target-specific binding peptide, thereby increasing expression of the protein of interest in comparison to a control subject lacking the bacterial cell or in comparison to the subject before administration of the bacterial cell.

65. The method of embodiment 64, wherein the compound is present in the subject at the time of administering the bacterial cell and wherein the target which binds to the heterologous target-specific binding peptide is administered to provide for increased accumulation of the protein of interest and/or the bioactive RNA molecule in the subject in comparison to a control subject lacking the bacterial cell or in comparison to the subject before administration of the bacterial cell.

66. The method of embodiment 64 or 65, further comprising administering the compound to the subject.

67. The method of embodiment 66, wherein said administering of the compound is performed either before administering the bacterial cell, concurrent with administration of the bacterial cell, or after administration of the bacterial cell.

68. The method of embodiment 64 or 65, wherein the subject is a human, a livestock animal, or companion animal.

69. A method of detecting a target of interest in a sample, the method comprising: (i) contacting the bacterial cell of any one of embodiments 46-62 with the sample and the compound, wherein the protein of interest comprises a reporter protein; and (ii) detecting the reporter protein to determine the presence of the target in the sample, wherein expression of the reporter protein is increased in samples containing the target in comparison to expression of the reporter protein in a control bacterial cell contacted with the compound and a control sample lacking or deficient in the target.

EXAMPLES

Example 1

Protein Biosensor Design in *E. coli* Cells

Figure 1A:
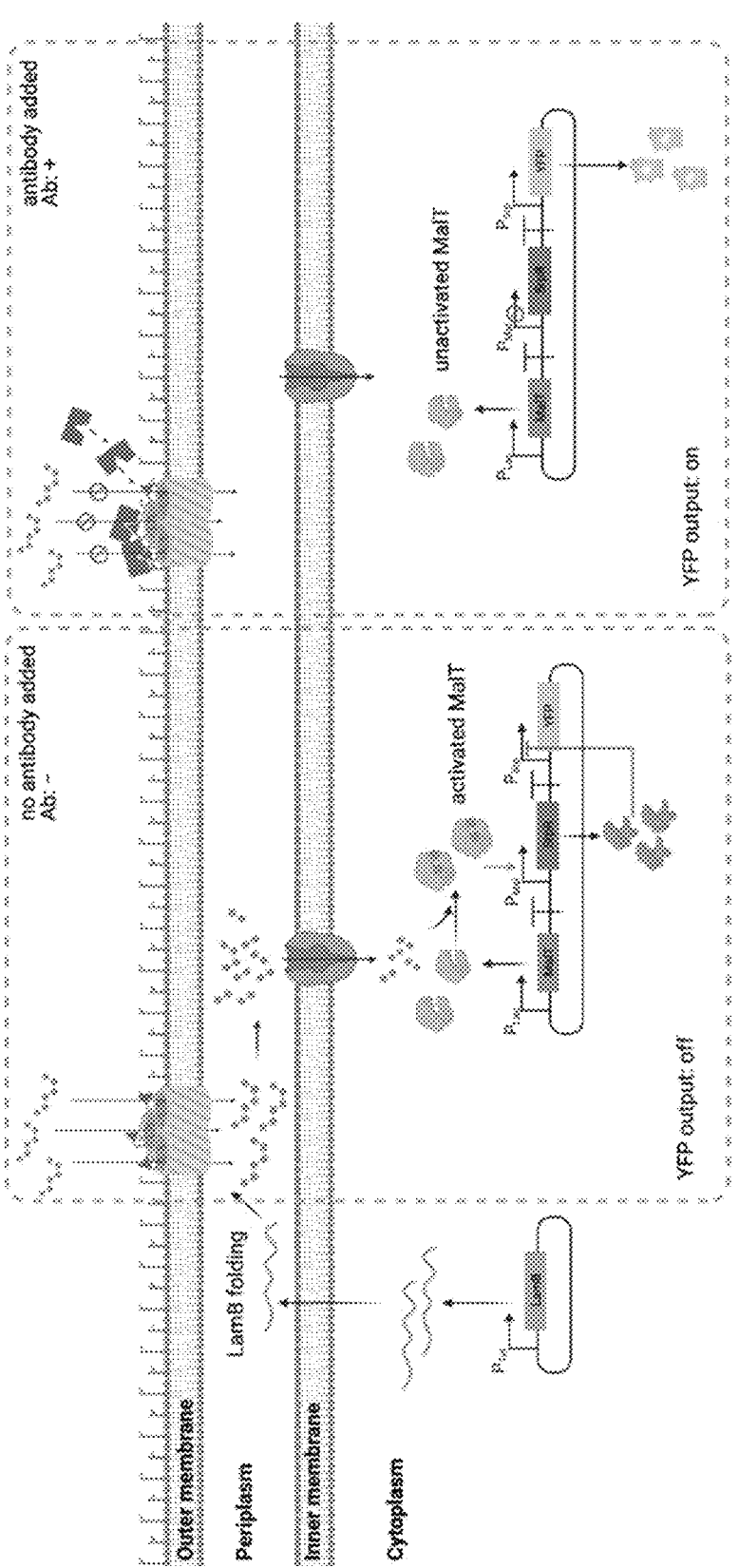
FIG. 1A illustrates the biosensor design. The biosensor is developed on gram-negative *E. coli* cells with four key components: maltose/maltodextrin transporter LamB on the outer membrane, target-specific binding peptides displayed on LamB outer loops, maltose induction system in the cytoplasm, and orthogonal promoter-repressor for signal inversion in the cytoplasm. LamB, as an outer membrane porin, is responsible for the uptake of maltose and maltodextrins into the periplasm, which is the first step of the *E. coli* maltose/maltodextrin transport system. MalT, as a transcriptional activator, can bind maltose as inducer to induce gene transcription controlled by a MalT-dependent promoter. Target-specific binding peptides were genetically inserted into the LamB DNA sequence and were expressed as fusions to LamB protein at the outer membrane extracellular side. Protein molecules in the medium can bind to the target-specific binding peptides inserted on LamB, thus sterically blocking the channels for maltodextrin transport. As a result, the gene expression induced by maltodextrin would be repressed by extracellular protein molecules which bind the target-specific binding peptides. Last, in order to invert the signal output so that the reporter, yellow fluorescent protein (YFP), can be expressed in the presence of extracellular proteins, a NOT gate was added by introducing an orthogonal Srp promoter and SrpR repressor. In summary, due to blocking of the LamB transporter through specific binding of the extracellular target protein to the fused peptides on LamB, the YFP expression was relieved from tight repression due to reduced expression of SrpR repressor, which was controlled by maltose induction system.

The technology entails the construction of a new signaling pathway in *E. coli* that converts a sugar transporter into a signaling pathway. This is achieved by blocking the transporter through specific binding of a target molecule of interest, which in turn activates a downstream signal due to the lack of the naturally transported sugar in the cytoplasm. To implement this design in *E. coli* cells, as shown in FIG. 1A, we assembled four key components, including maltose/maltodextrin transporter LamB on the outer membrane, target-specific binding peptides displayed on LamB outer loops, maltose induction system in the cytoplasm, and orthogonal promoter-repressor for signal inversion in the cytoplasm. To be specific, LamB, also called maltoporin, is an outer membrane porin responsible for the uptake of maltose and maltodextrins into the periplasm, which is the first step of the *E. coli* maltose/maltodextrin transport system MalEFGK2. Second, MalT, as a transcriptional activator, is essential for the transcription of most genes related to maltose metabolism. MalT can bind maltose as an inducer to induce gene transcription controlled by a MalT-dependent promoter. For inducing a MalT-dependent promoter using maltodextrin, maltodextrin transport via LamB is the rate-limiting step within the transport and induction systems. A variety of target-specific binding peptides were genetically inserted into extracellular-loop regions of the LamB DNA and were successfully expressed in the outer membrane. Protein receptors in the medium can bind to the specific target-specific binding peptide ligands inserted on LamB, thus sterically blocking the channels for maltodextrin transport. Last, in order to invert the signal output so that the fluorescent reporter protein can be expressed in the presence of extracellular proteins, a NOT gate was added by introducing an orthogonal Srp promoter and SrpR repressor. In this signaling pathway, when the extracellular protein was present in the cell medium, it hindered LamB-mediated transport through specific binding to the ligand peptides in LamB; as a consequence, the SrpR repressor, which was controlled by the maltose induction system, was no longer strongly expressed, so the expression of YFP increased.

Figure 1B:
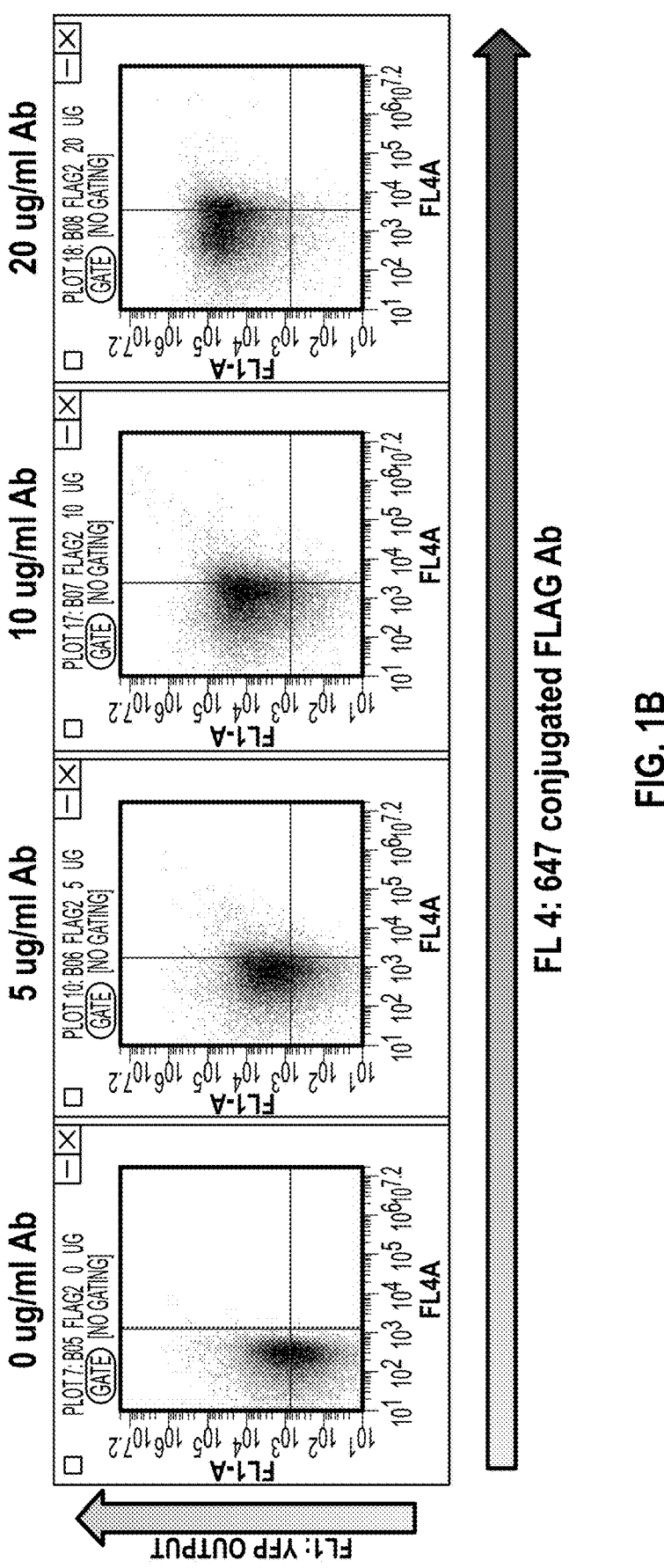
FIG. 1B shows flow cytometry of *E. coli* cells after 8 h co-incubation with Alexa Fluor (AF) 647 conjugated FLAG tag antibody at 37° C.
Figure 1C:
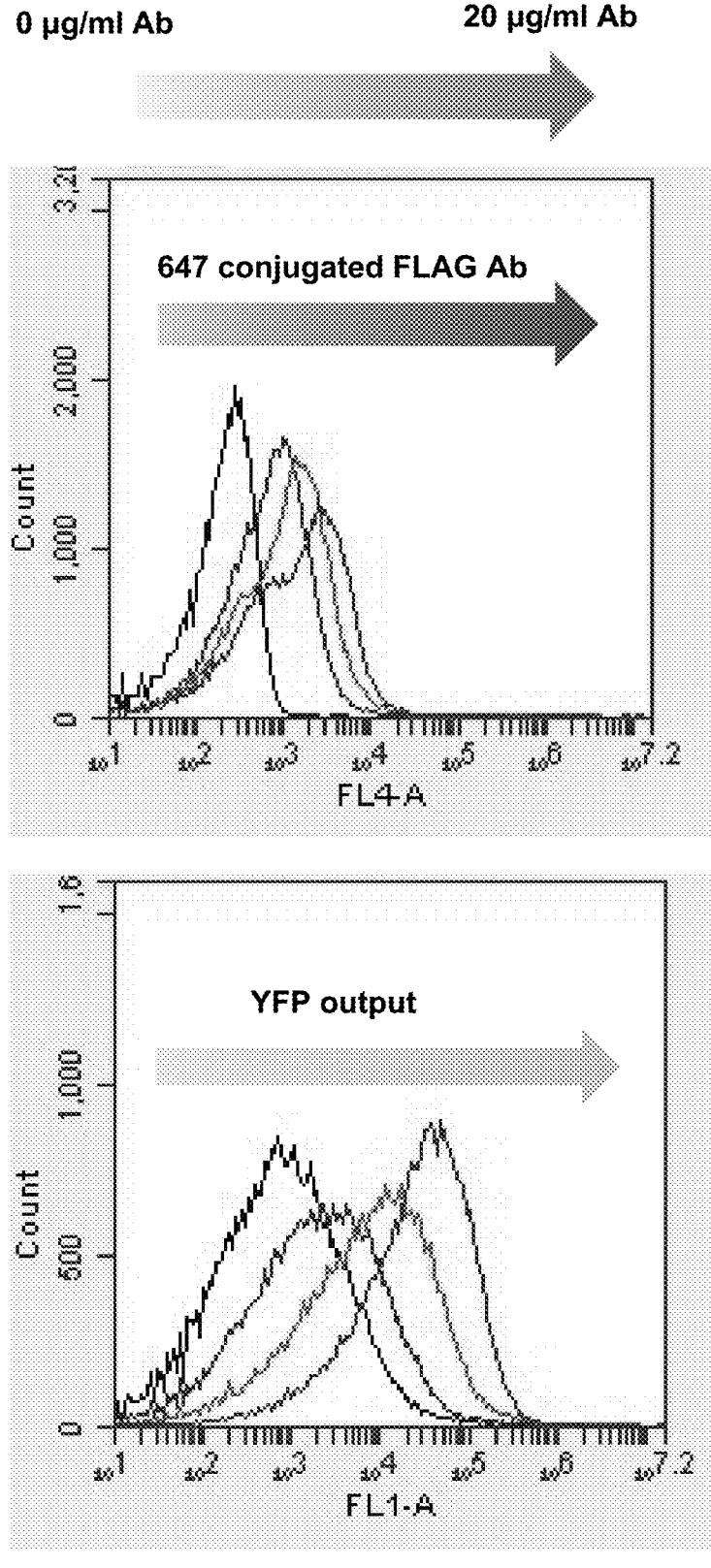
FIG. 1C is a histogram plot of the flow cytometry results in FIG. 1B; the more AF 647 conjugated FLAG tag antibody (target) was added to the cell culture, the more peptide ligands on LamB were bound by antibody, and the more YFP was expressed as the signal output.

For a proof-of-concept experiment, FLAG tag was inserted into the LamB outer loop 4 and loop 9 and the FLAG tag antibody was used as the target protein for detection. As shown in the flow cytometry scatter plots in FIG. 1B, when more AF 647 conjugated FLAG tag antibody input was added to the cell medium, more FLAG tag peptides inserted into the LamB outer membrane protein loops were bound to the FLAG tag antibody (FL4+population), and higher output YFP expression was observed (FL1+population) due to the lack of SrpR repressor, as the result of the bound FLAG tag antibody on the cell outer membrane blocking the transport of inducer maltodextrin. The histogram in FIG. 1C also illustrates the correlation between the higher YFP output and the higher extracellular FLAG tag antibody concentration added in the cell medium.

Example 2

LamB-Dependent Maltose Induction System

Figure 2A:
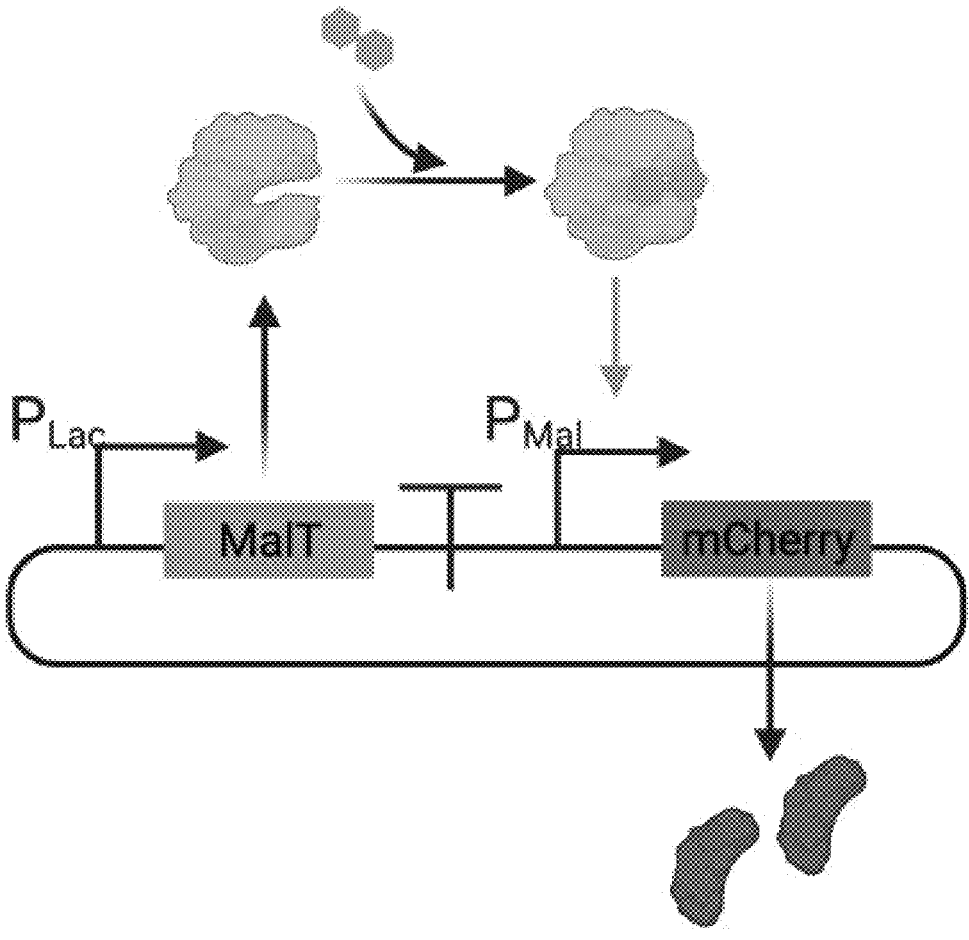
FIG. 2A illustrates the LamB-dependent maltose induction system. MalT, activated by maltose or maltodextrin, can induce gene transcription controlled by a MalT-dependent promoter.
Figure 2B:
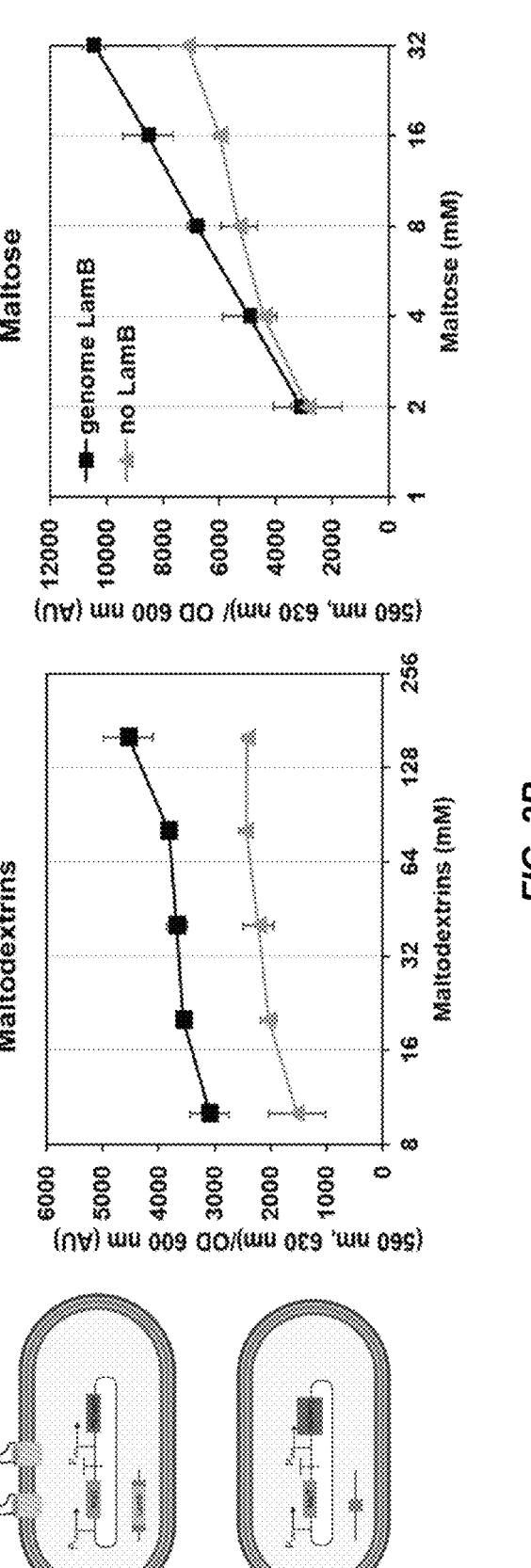
FIG. 2B shows *E. coli* cells transformed with the maltose induction system plasmid (top left: TOP10 pro as the host strain; bottom left: TOP10 pro ΔLamB as the host strain). Dose response curves of inducer maltodextrin (chain of n=4-7 D-glucose units) and maltose (n=2 D-glucose units) and normalized mCherry expression in two different host strains after 14 h incubations at 37° C.
Figure 2C:
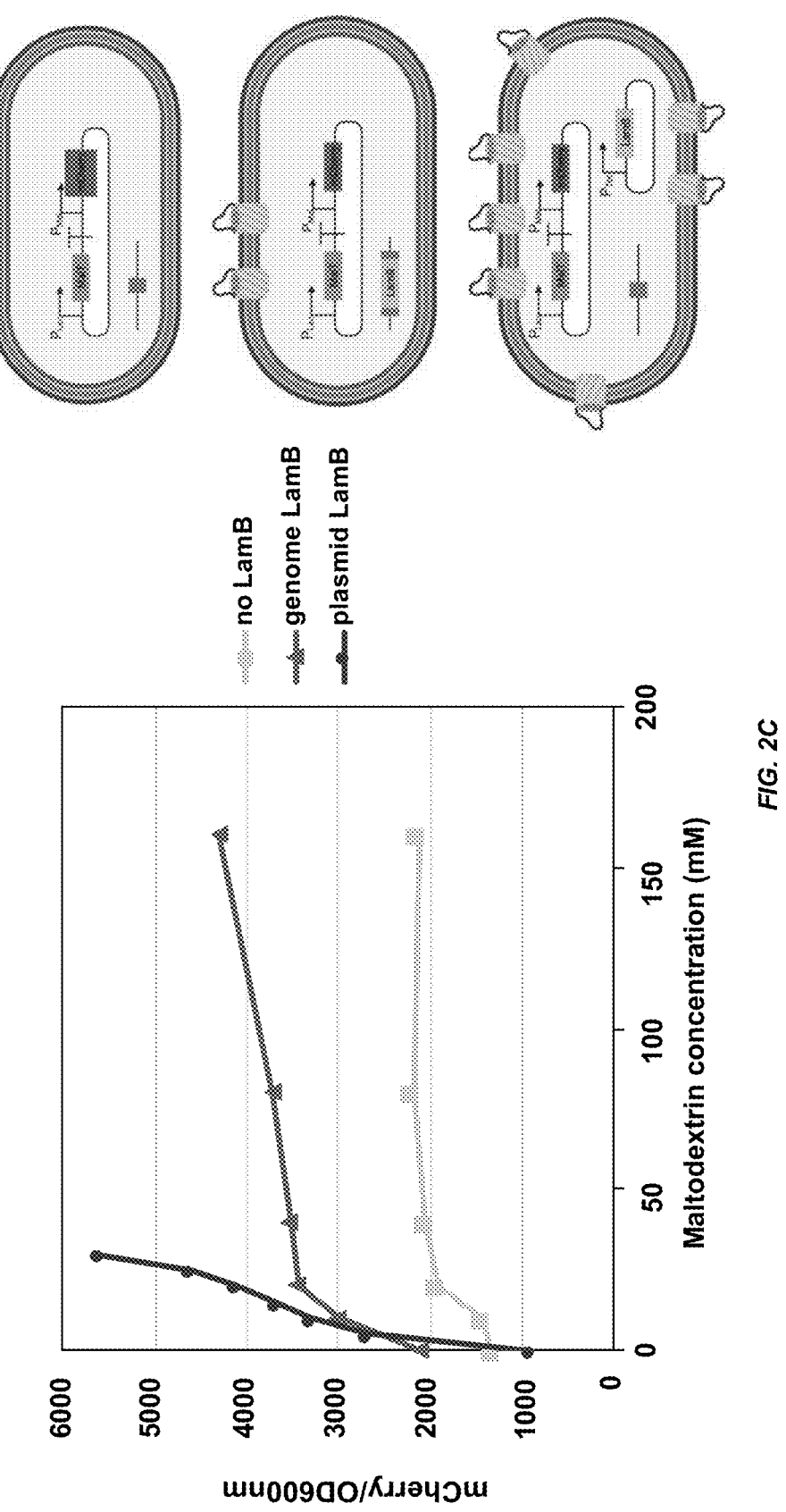
FIG. 2C shows the maltose induction system plasmid transformed into three different host strains (TOP10 pro ΔLamB, TOP10 pro, and TOP10 pro ΔLamB with overexpressed recombinant LamB). Dose response curve of inducer maltodextrin (n=4-7) in three different host strains after 14 h incubation at 37° C.

Maltose, as a sugar, can also serve an inducer for gene expression regulation related to maltose metabolism. The regulation was implemented by a maltose induction system, which includes the MalT transcriptional activator, and the promoter DNA sequences that can be induced by the activated MalT. In this transcriptional induction process, maltose is the inducer to activate MalT (FIG. 2A). To uptake maltose/maltodextrin into the *E. coli* cytoplasm, a specific maltoporin LamB on the outer membrane is the first step to transport maltose/maltodextrin to the periplasm. As LamB transport being the rate-limiting step is the prerequisite for the whole biosensor design, we constructed a LamB knockout *E. coli* strain and tested the maltose induction system using maltose (n=2 D-glucose units)/maltodextrin (n=4-7 D-glucose units) as the inputs and mCherry expression level as the output. From the dose-response curve shown in FIG. 2B, larger differences between the wild-type host strain and the LamB knockout strain were observed when maltodextrin was added as the inducer. This observation was because the physically larger maltodextrins relied more on LamB than the smaller maltose, which can cross the outer membrane to some degree through passive diffusion. As a result, we opt to use maltodextrin as the inducer, instead of maltose, for future experiments to test biosensor performance. Next, we tested the maltose induction system with different LamB concentrations. In FIG. 2C, three strains were constructed—one with no LamB expression, one with native genomic LamB expression, and one with high plasmid recombinant LamB expression—and the dose-response curve of mCherry output vs. maltodextrin was plotted. This result illustrated that maltodextrin transport via LamB can be rate-limiting through the maltose transport and the induction system under appropriate experimental conditions.

Example 3

Target-Specific Binding Peptide Insertions on LamB Outer Loops

Figure 3A:
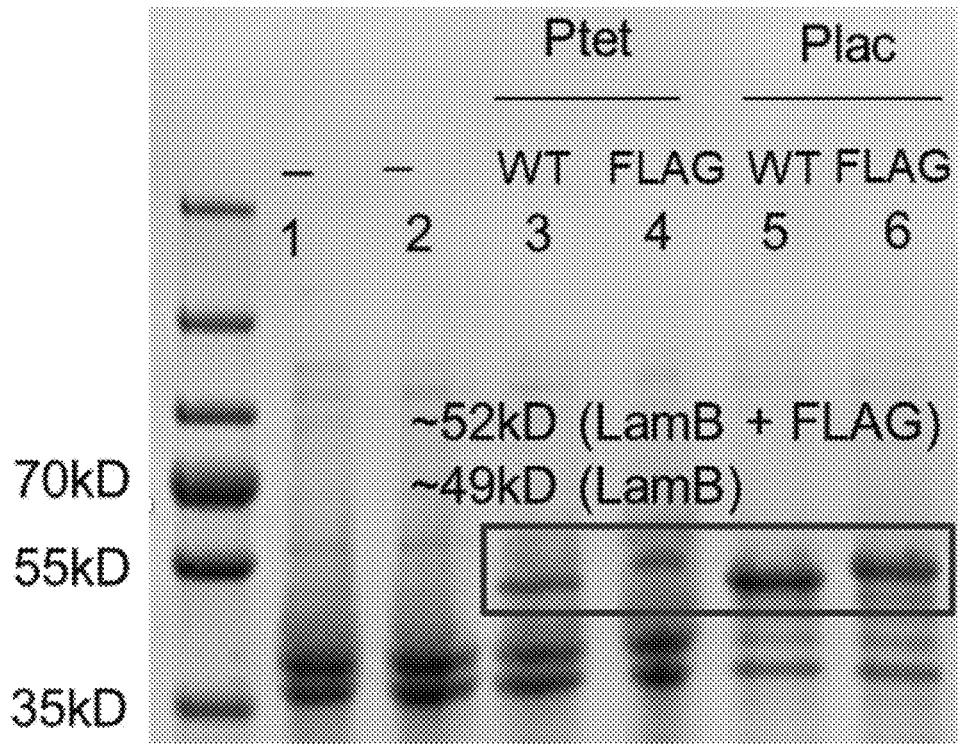
FIG. 3A-C show target-specific binding peptide insertions into the LamB outer membrane protein.
Figure 3B:
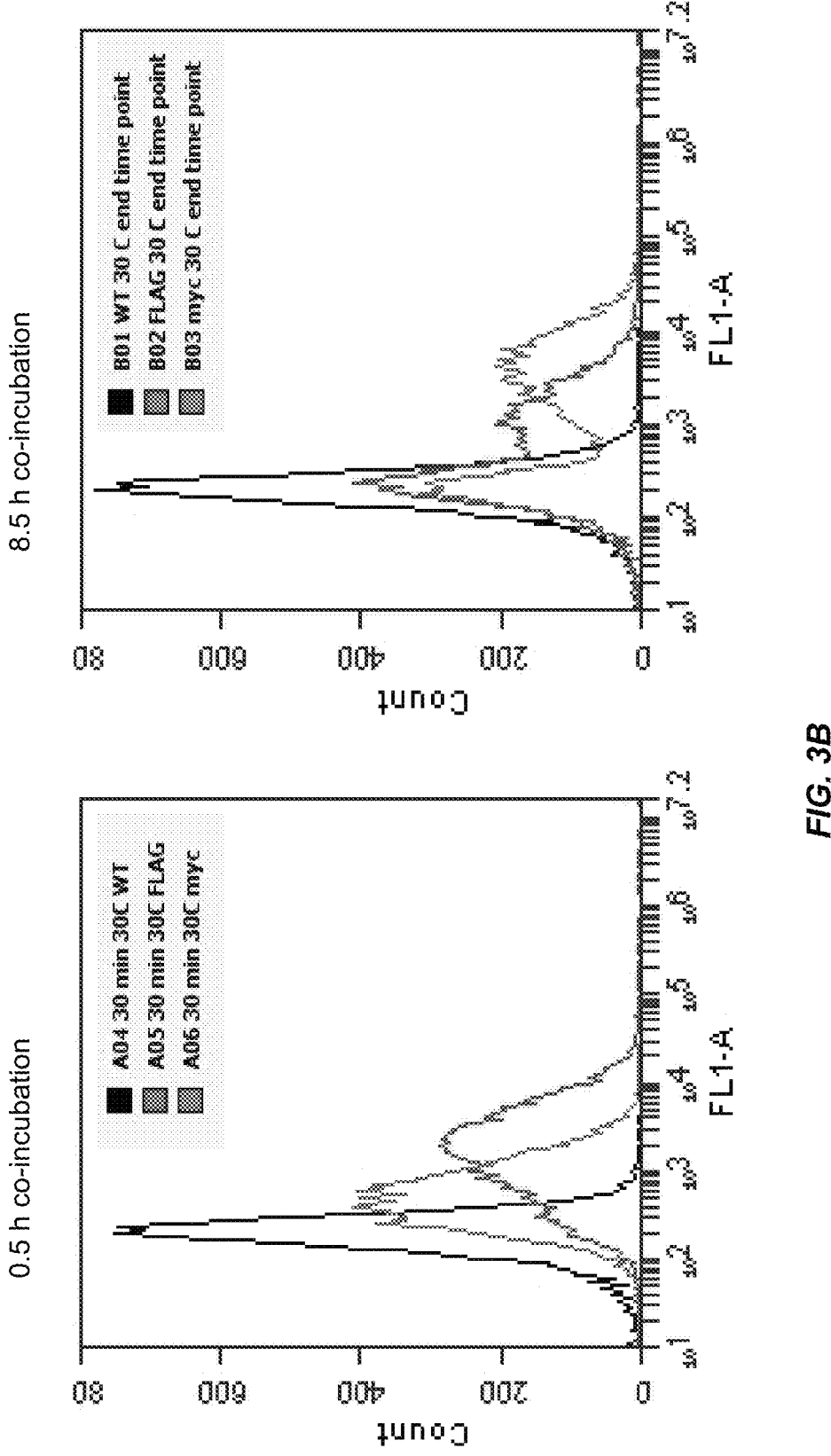
Figure 3C:
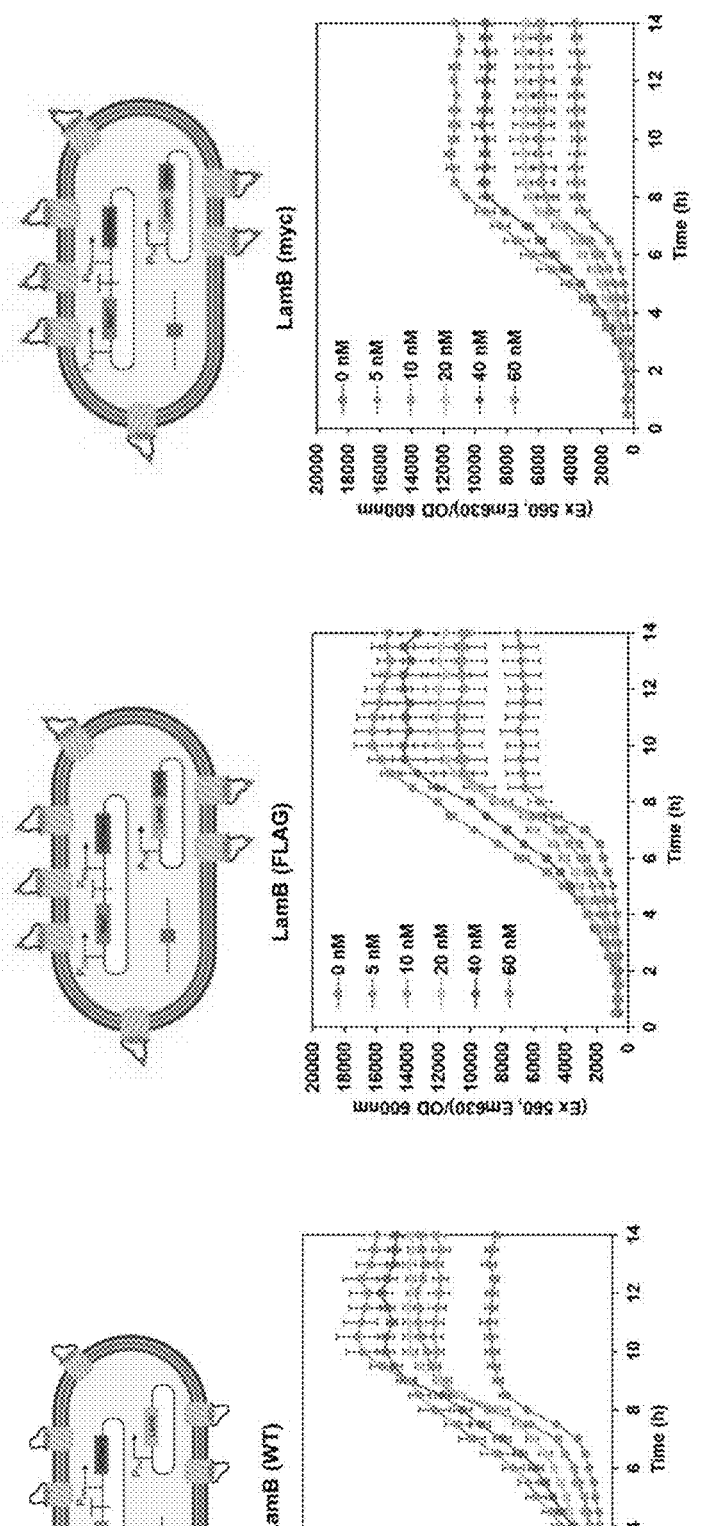

Small target-specific binding peptides were genetically inserted into the LamB coding gene at loop 4 and loop 9. To ensure that after peptide insertion the LamB protein could still properly fold and assemble on the outer membrane and be functional, we first examined the outer membrane fraction cell lysate by SDS-PAGE. The gel image in FIG. 3A showed that with FLAG tag peptide insertions, the LamB protein could still target to the outer membrane properly. Next, to test if the inserted peptides could be displayed towards the extracellular side and specifically bind to their receptor, conjugated FLAG-tag antibody or myc-tag antibody were added to the induced cell culture and incubated for 0.5 h or 8.5 h at 37° C. The flow cytometry results in FIG. 3B illustrated that after 30 min incubation, the displayed FLAG-tag or myc-tag epitope peptide could specifically bind to their corresponding antibodies, whereas the wild-type LamB could not bind to either FLAG-tag antibody or myc-tag antibody. The flow cytometry histogram in FIG. 3B (right) implied that the binding between displayed epitope peptides and antibodies in the *E. coli* culture was able to last for hours at 37° C. incubation with vigorous shaking, although some *E. coli* cells lost the bound antibodies, which might be due to the *E. coli* culture overgrowth or loss of antibody function after 8 h incubation. Finally, to ensure that the LamB was still functional as a maltodextrin transporter after peptide insertions, the maltose transport/induction system was validated in three different strains. As shown in FIG. 3C, wild-type LamB, LamB with FLAG tag peptide insertion, and LamB with myc tag peptide insertion were expressed from a transformed plasmid. The second plasmid responsible for the maltose induction system characterization was co-transformed. The output mCherry expression was monitored continuously with different maltodextrin inducer concentrations. The results illustrated that with FLAG tag or myc tag insertion on the LamB outer loops, the LamB maltodextrin transport function was retained, although myc insertion reduced the LamB transport rate to some extent, compared to the wild-type LamB.

Example 4

Experimental Method Development and Key Protein Expression Regulation

Figure 4B:
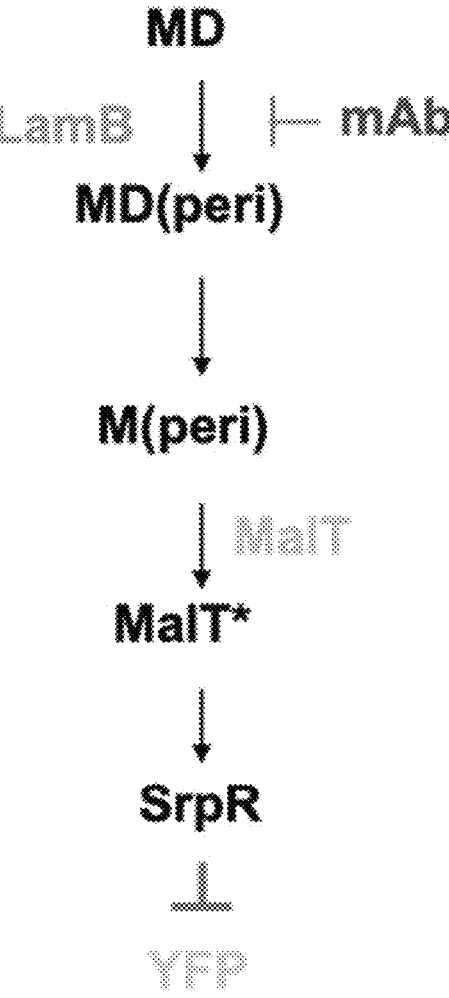

To develop the method for biosensor characterization, optimization of experimental procedures and conditions was first conducted. First, since LamB is an extremely hydrophobic protein, lower temperature is favored for LamB protein proper folding and assembling on the *E. coli* outer membrane. However, for other protein expression in cytoplasm, 37° C. is optimal for shorter response time to extracellular proteins. To resolve this conflict, a dual-stage incubation method with different temperatures was developed. As shown in FIG. 4A, in the first stage (Step 4), *E. coli* was incubated at a lower temperature (30° C.) for LamB expression, then the cells were washed to remove the inducer of LamB expression. In the second stage (Step 5-6), *E. coli* was incubated at a higher temperature (37° C.) for characterization.

Before characterization with extracellular target, the *E. coli* incubation for seed culture and the first-stage expression of LamB were performed in the presence of a high concentration of maltodextrin (40 mM), so the cell could produce high levels of SrpR to ensure tight repression of YFP. The cells were then washed prior to characterization, and a moderate concentration of maltodextrin (10-20 mM) was added for biosensor characterization. In addition, during binding of the extracellular proteins to the inserted peptides, maltodextrin molecules would already have been taken up through the LamB transporter before the channels were blocked by extracellular protein. To minimize this, signal proteins were added to the culture and incubated for 30 min prior to the addition of the maltodextrin inducer.

Figure 4C:
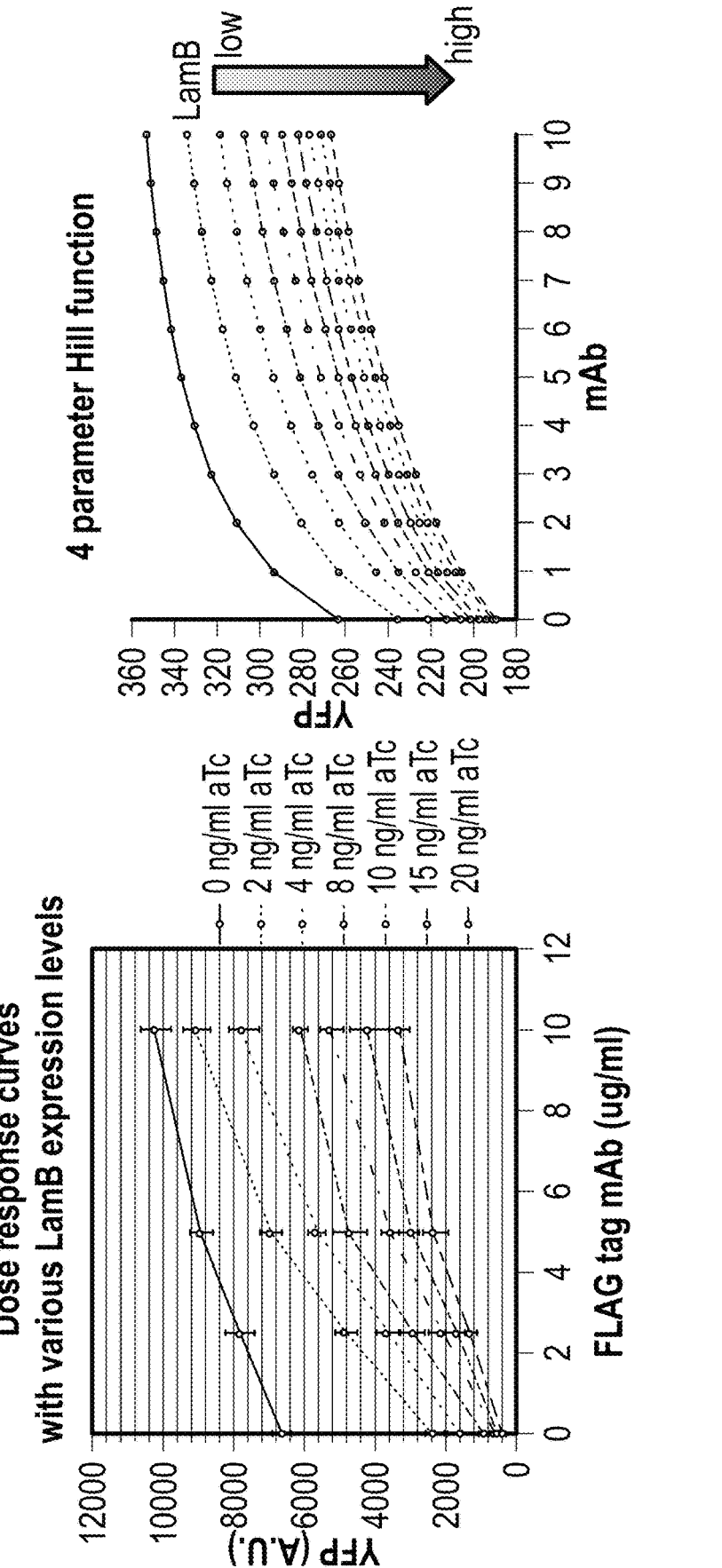
Figure 4D:
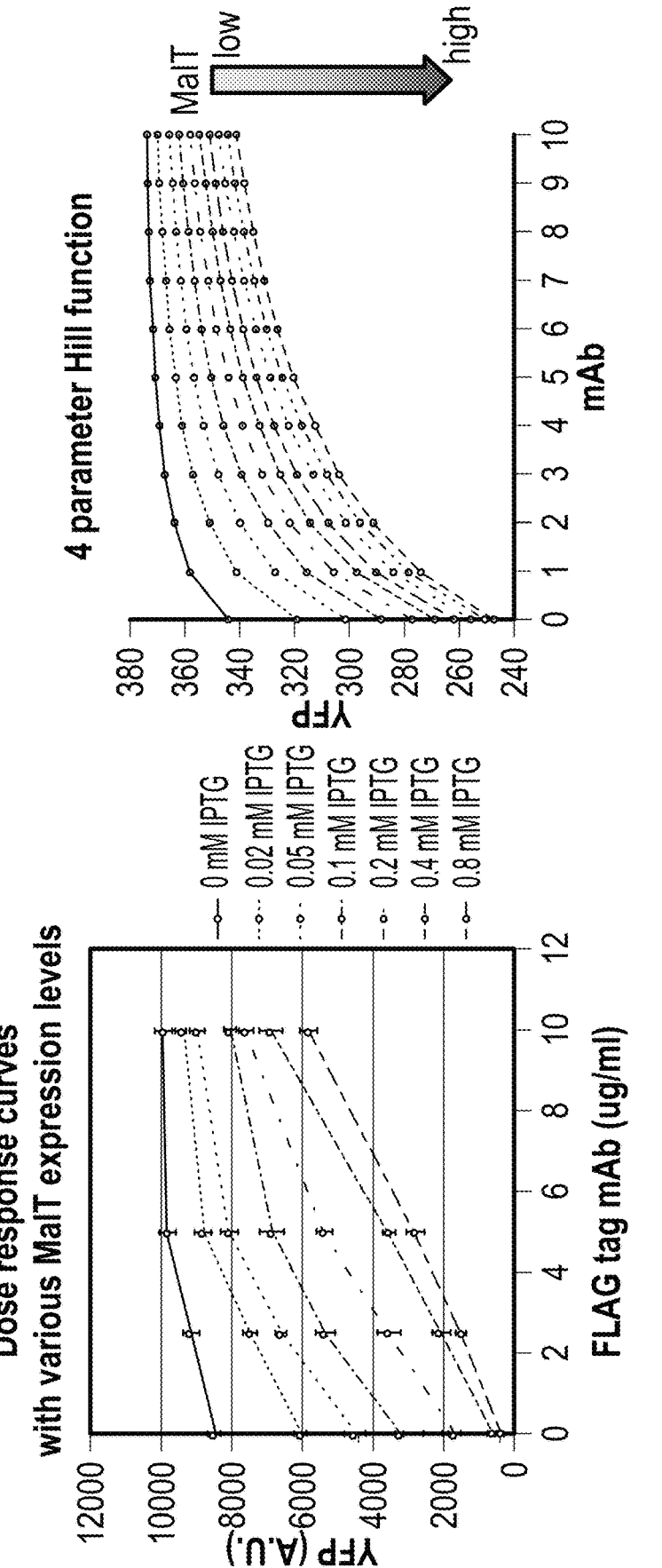

Next, to regulate the dynamic range of the biosensor and minimize the signal leakiness, different LamB and MalT expression levels were experimentally tested. Based on the signaling pathway described in FIG. 4B, to minimize the signal leakiness, a minimum LamB expression level was required to ensure sufficient maltodextrin transport flux into the cell to produce enough SrpR for repressing YFP expression in the absence of extracellular protein. Conversely, to expand the dynamic range, higher MalT expression level was required so that the SrpR expression rate would be only maltodextrin-dependent and the YFP expression level would reflect the maltodextrin concentration in the cytoplasm, which was determined by the LamB transport rate and extracellular protein concentrations. In the experiment, various aTc concentrations were added into the culture in Step 4 to regulate the LamB expression levels (FIG. 4C). As expected, higher LamB concentrations gave less YFP background when there was no extracellular input protein added, but also sacrificed sensitivity since higher LamB expression levels would need significantly more antibodies to block the channels and thus attenuate the downstream signaling pathway. Next, various IPTG concentrations were added into the cell culture in Step 4 to regulate the MalT expression levels (FIG. 4D). Similarly, higher MalT concentrations gave less YFP background, as more activated MalT would more tightly repress output YFP expression in the absence of antibody. However, in contrast to LamB, higher MalT levels could still retain a large dynamic range of YFP output. In addition, the dose-response curves from the experimental result were in agreement with mathematical simulations of the processes for both LamB and MalT regulation.

Example 5

Detection of Human Cytokines Using the *E. coli* Protein Biosensor

Figure 5A:
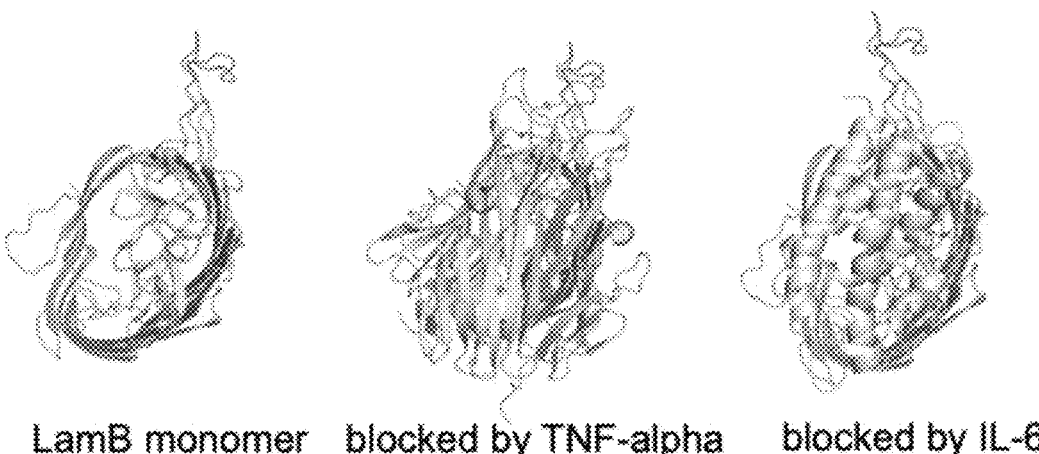
FIG. 5A-C show detection of human cytokine molecules by an engineered *E. coli* biosensor.
Figure 5B:
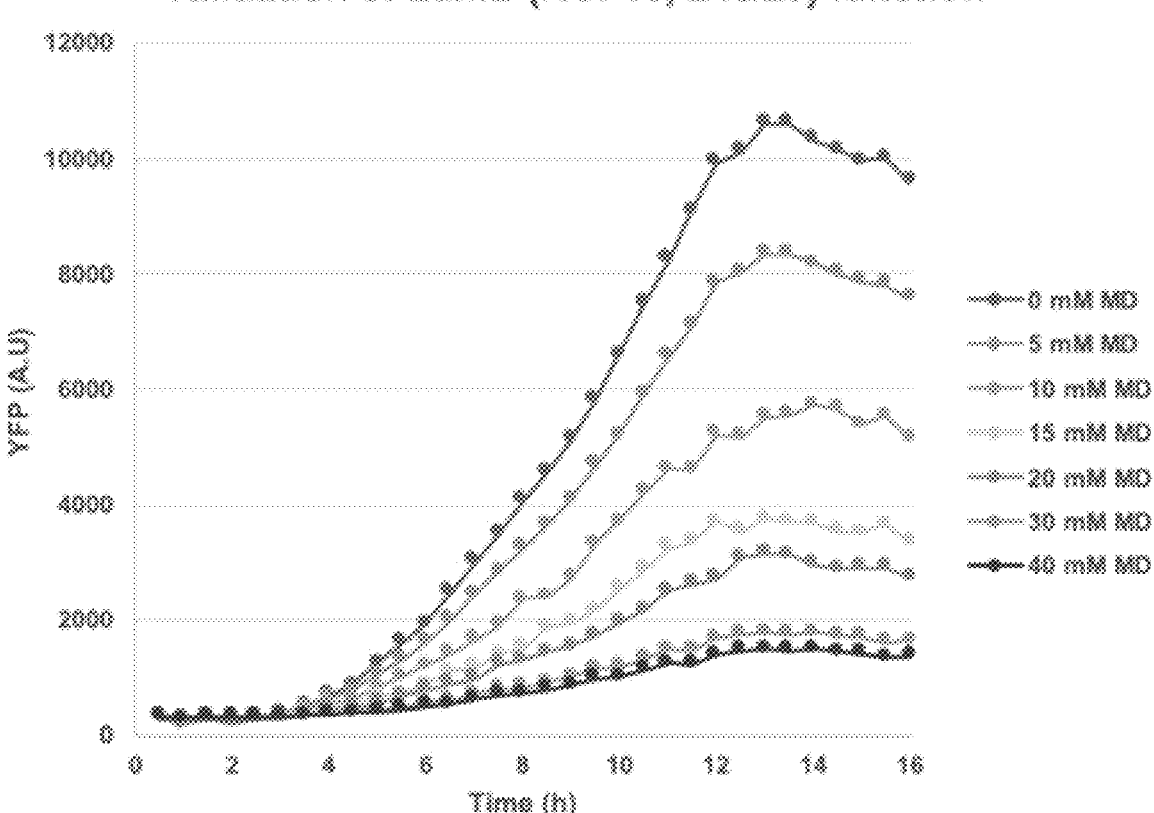
Figure 5C:
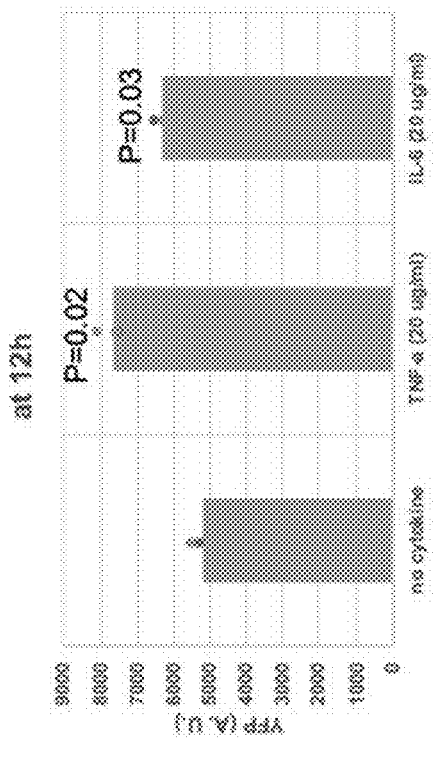
Figure 5C:
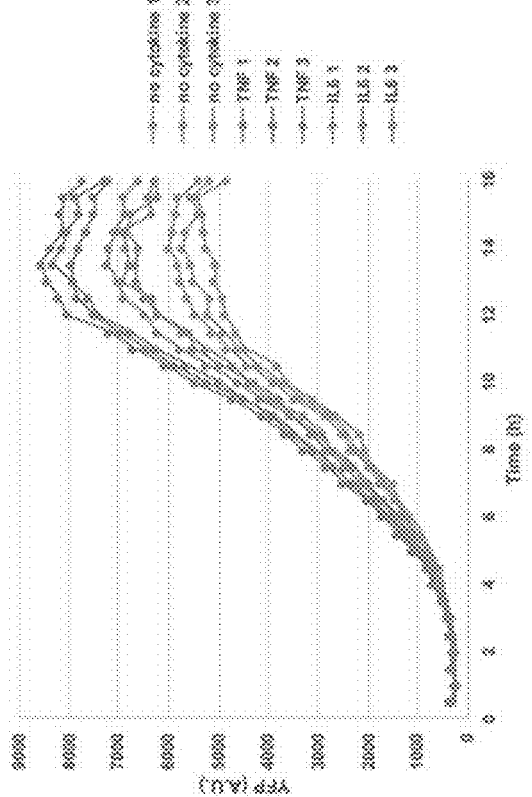

Based on the modularity of this biosensor design, detection of many different targets should be possible. By altering the inserted peptide ligands inserted on LamB, the LamB channel could be blocked by different receptors. For example, the bacteria could be easily repurposed for detecting different disease-relevant protein molecules in the human body. As proof of concept, an 18-amino-acid peptide KCF18 that can specifically bind to two human cytokines, TNF-α and IL-6, was inserted into the LamB transporter (FIG. 5A). Based on the YFP expression time curves with different maltodextrin concentrations in FIG. 5B, similar to the FLAG/myc tag insertion, the LamB maltodextrin transporter was still functional after KCF18 peptide insertion in its outer loops. Next, either TNF-α or IL-6 was added to the cell culture to block the engineered LamB channels by specific binding. As shown in FIG. 5C, *E. coli* cells could detect both extracellular TNF-α and IL-6 and then translate this extracellular binding into YFP expression in the cytoplasm.

Example 6

Optimization of the Biosensor Sensitivity

Figure 6A:
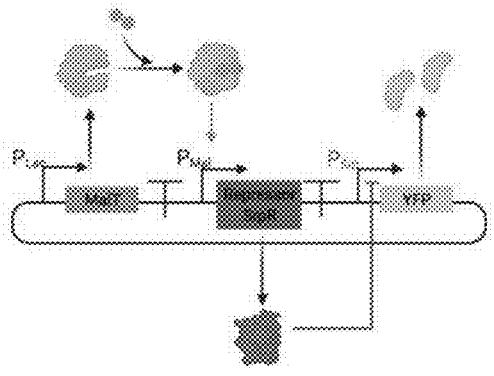
FIG. 6A-C show further optimizations of the biosensor sensitivity.
Figure 6A:
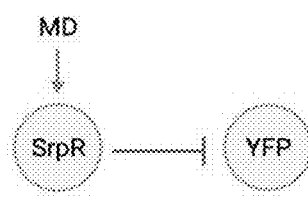
Figure 6A:
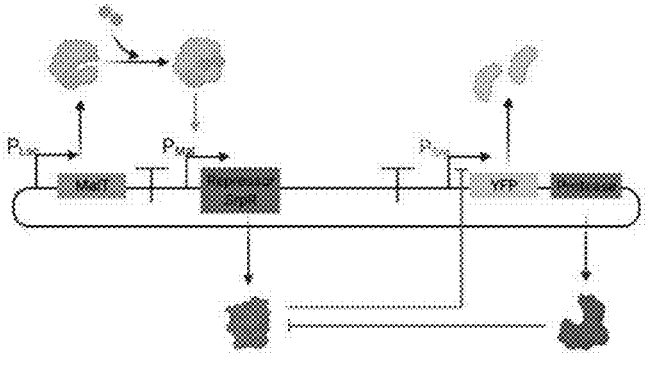
Figure 6A:
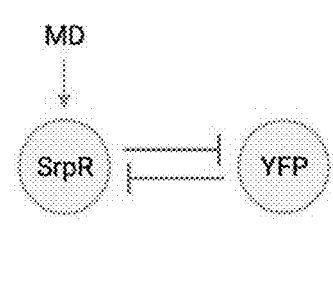
Figure 6A:
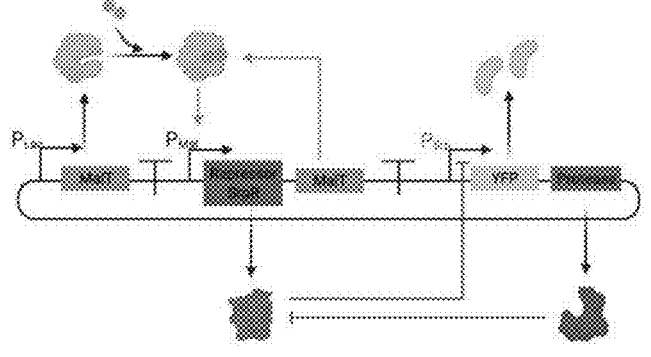
Figure 6A:
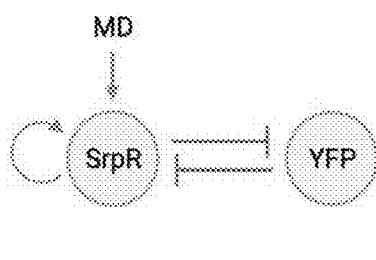
Figure 6B:
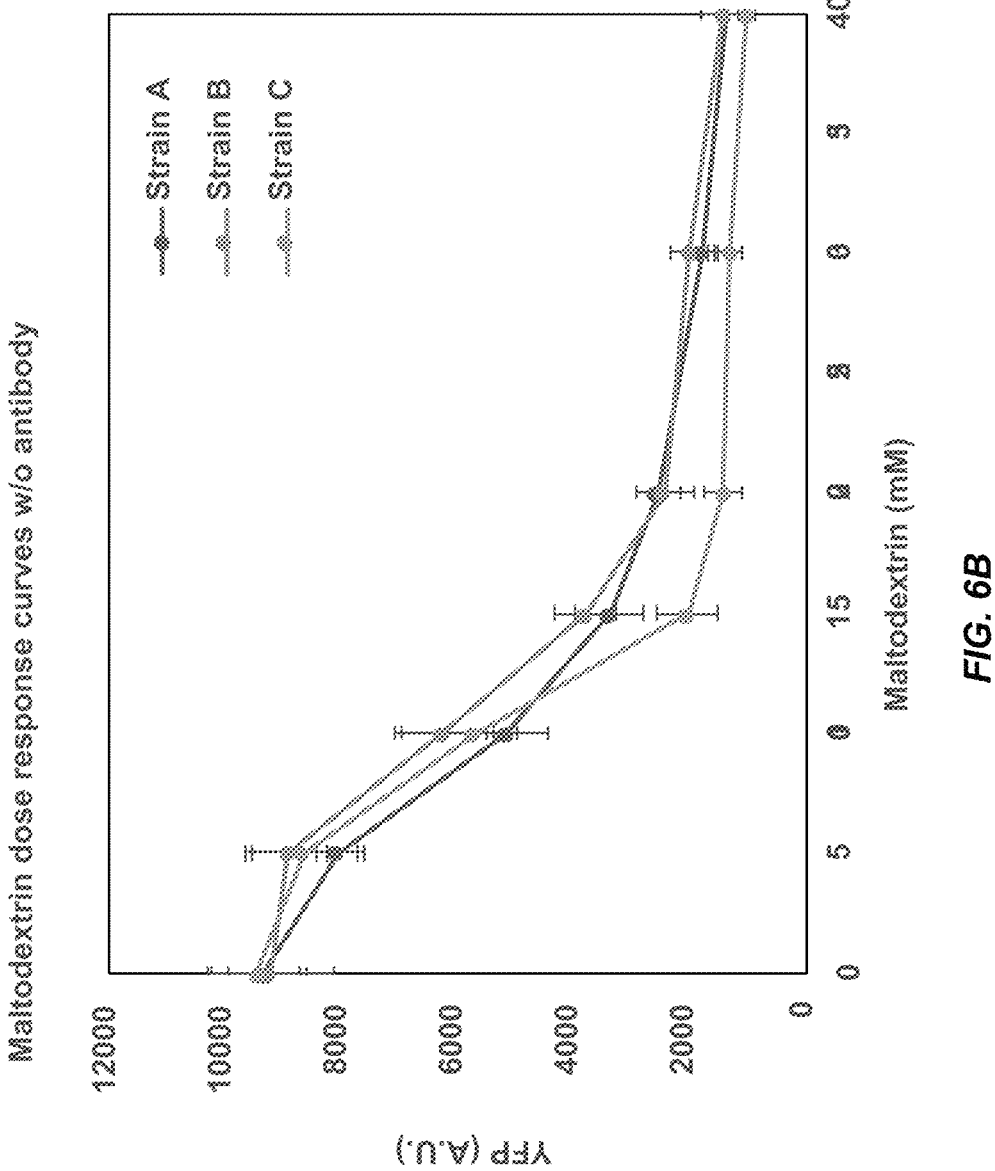
Figure 6C:
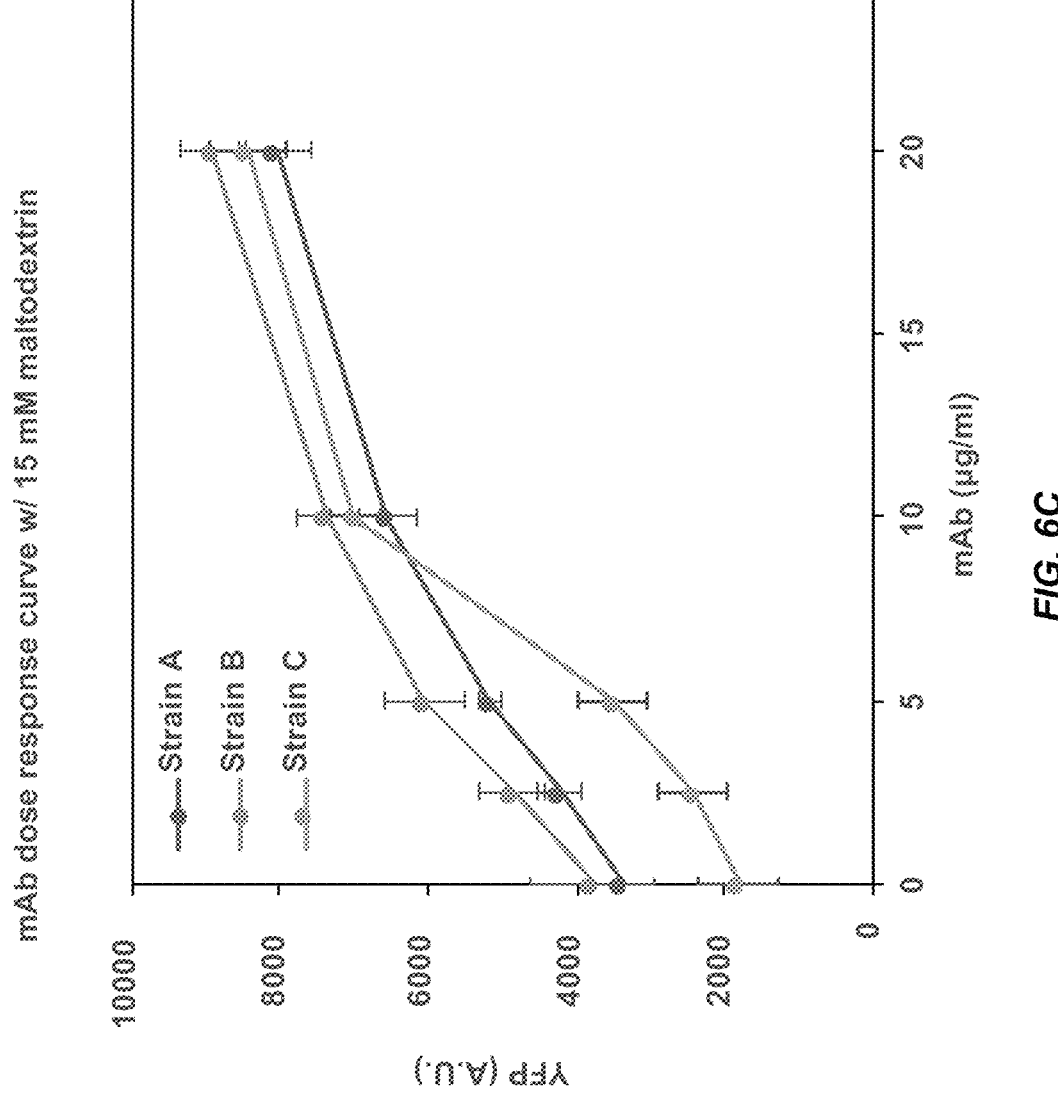

To further optimize the biosensor performance, particularly to improve its sensitivity, the downstream signaling pathway was genetically engineered to increase the switch-like response of the biosensor dose-response curves. For the output of YFP expression in the cytoplasm, the original signaling pathway used SrpR repression of YFP for signal inversion in the last step (strain A in FIG. 6A). To create an antagonistic interaction between SrpR and YFP and thus generate more ultrasensitive behavior, first, a negative feedback loop was introduced by putting an orthogonal mf-lon protease, which could specifically degrade tagged SrpR, after the YFP gene within the same transcript controlled by the $S_{Srp}$ promoter $P_{Srp}$ (strain B in FIG. 6A). Next, a positive feedback loop was introduced by putting a second copy of the MalT gene, which encodes for the maltose transcriptional activator, after the SrpR gene within the same transcript controlled by the maltose promotor $P_{Mal}$ (strain C in FIG. 6A). For strains A, B and C, maltodextrin dose-response curves were generated separately by adding different maltodextrin concentrations in the absence of any input extracellular proteins. In FIG. 6B, strain C exhibited the steepest slope among the strains within the range of 5-15 mM maltodextrin, indicating that within this range, the downstream signaling pathway in strain C more significantly amplified differences in maltodextrin uptake into larger output signal differences. As a result, strain C provided higher sensitivity when the maltodextrin concentration was within the range of 5-15 mM maltodextrin. As expected, based on the FLAG tag antibody dose-response curves with 15 mM maltodextrin added as the inducer (FIG. 6C), strain C showed the lowest basal YFP expression and the largest switch-like response. Higher biosensor sensitivity could be achieved by introducing feedback loops in the downstream signaling pathway while maintaining the high design modularity.

Materials and Methods for Examples 1-6

Strains and Reagents

All cloning was performed in *E. coli* strain XL1-blue (Agilent, 200130), and *E. coli* strain TOP10 pro (F'[lacI$^q$ Tn10(tet$^R$)] mcrA Δ(mrr-hsdRMS-mcrBC) φ80lacZΔM15 ΔlacX74 deoR nupG recA1 araD139 Δ(ara-leu)7697 galU galK rpsL(Str$^R$) endA1 λ⁻, a gift from James J. Collins) was used for all experimental characterizations. *E. coli* cells were grown in LB medium (Fisher Scientific, DF0446173); SOB medium (Teknova, S0210); and M9 medium containing M9 salt (Sigma-Aldrich, M6030), 0.4% glycerol (Sigma-Aldrich, G7757), 0.2% casamino acids (MP Biomedicals, 113060012), 2 mM MgSO$_4$ (Fisher Scientific, BP213), 0.1 mM CaCl$_2$ (Fisher Scientific, BP510) and 0.34 g/L thiamine hydrochloride (Sigma-Aldrich, T4625). Antibiotics carbenicillin (100 μg/ml; Teknova, C2105) and chloramphenicol (25 μg/ml; Sigma-Aldrich, C0378) were used to maintain plasmids in *E. coli*. Isopropyl β-D-thiogalactopyranoside (IPTG, Millipore Sigma, 420322), anhydrotetracycline hydrochloride (aTc, AdipoGen, CDX-A0197-M500), maltose (Sigma-Aldrich, 63418), and maltodextrins (n=4-7, Sigma-Aldrich, 419672) were used to induce gene expression.

Orthogonal SrpR repressor and promoter were derived from plasmid pRF-SrpR (Addgene #49372); orthogonal protease mf-lon was cloned from plasmid pECGMC3 (Addgene #75441); and the LamB gene was cloned from the TOP10 pro strain genomic DNA. Myc tag monoclonal antibody (Thermo Fisher Scientific, MA1-21316), c-Myc monoclonal Antibody (9E10), Alexa Fluor 488 (Thermo Fisher Scientific, MA1-980-A488), Alexa Fluor 647 anti-c-Myc Antibody (BioLegend, 626810), DYKDDDDK tag antibody (Thermo Fisher Scientific, MA1142), DYKDDDDK tag monoclonal antibody (L5), Alexa Fluor 488 (Thermo Fisher Scientific, MA1-142-A488), and ALEXA FLUOR® 647 anti-DYKDDDDK Tag Antibody (BioLegend, 637316) were used as extracellular signals for biosensor characterization (DYKDDDDK is SEQ ID NO: 16). Human TNF-α (Goldbio, 1130-01-100) and human IL6 (Goldbio, 1110-06-20) were used for biosensor cytokine detection test.

Strain Development

To knockout the LamB gene from the *E. coli* strain TOP10 pro genome, plasmid pKD46 was transformed to the host strain TOP10 pro, then a single colony was grown in LB medium at 30° C. and harvested as electrocompetent cells. Next, linear PCR product of kanamycin resistance gene flanked by LamB homologous sequences was transformed to the TOP10 pro strain and the cells were selected on a LB plate with kanamycin. After verifying deletion with colony PCR, a single colony was grown in LB medium at 37° C. and then prepared as electrocompetent cells. Next, plasmid pCP20 was transformed to remove the kanamycin resistance gene from the genome. Last, a single colony was grown at 43° C. to eliminate the pCP20 plasmid. The strain with LamB knockout was verified by colony PCR.

Plasmid Construction

Cloning was performed with NEBuilder HiFi DNA Assembly (New England Biolabs, E2621) or restriction enzymes (New England Biolabs). All polymerase chain reactions (PCRs) were performed using Phusion Hot Start Flex DNA Polymerase (New England Biolabs, M0535). Oligonucleotides were obtained from IDT (Integrated DNA Technologies). Ligation reactions were conducted using T4 ligase (New England Biolabs, M0202) and then transformed into chemically competent XL1-Blue cells (Agilent, 200130). The plasmid DNA was extracted using the QIA- GEN plasmid DNA miniprep kit following the manufacturer's instructions. Plasmid sequences were confirmed by Sanger sequencing performed by ACGT. The nucleotide sequences of components include SEQ ID NO: 19 (P(Mal) promoter), SEQ ID NO: 20 (P(SrpR) promoter, SEQ ID NO: 21 (high-efficiency terminator), and SEQ ID NO: 22 (protein degradation tag #3 (pdt #3; Cameron et al. *Nat. Biotechnol.* 32, 1276-1281 (2014)).

To clone LamB with small peptide insertions (e.g., target-specific binding peptides), we used an overlap-extension PCR cloning strategy. The PCR product was assembled with a TetR-controlled promoter, then digested and inserted into a plasmid backbone derived from plasmid pTU2-A-RFP (Addgene, #74090), which contains a low copy p15A origin of replication and chloramphenicol acetyltransferase.

SDS-PAGE and Western Blot Analysis

To verify peptide insertion in the LamB protein, 2 ml OD600=1.0 induced *E. coli* cell culture was centrifuged for 3 min at 13,000 rpm and then resuspended in 250 μl of PBS buffer containing DNAse (8 μl of 1 mg/ml solution) and RNAse (8 μl of 10 mg/ml solution). The resuspended bacteria cells were lysed by sonication, and non-broken cells were eliminated by low-speed centrifugation. The supernatants were recovered and centrifuged for 60 min in a microfuge at 20,000 rpm. The pellet was resuspended in 175 μl PBS containing 0.5% Sarcosyl (sodium lauroyl sarcosinate, Fluka) and incubated for 30 min at room temperature. The mixture was then centrifuged for 60 min at 20,000 rpm. The outer membrane fraction pellet was resuspended in NuPAGE™ LDS Sample Buffer (Thermo Fisher Scientific, NP0007), loaded onto an SDS-PAGE gel after 10 min, 70° C. heat denaturation, and then was stained by Coomassie blue for visualization after electrophoresis.

To verify the stability of antibodies added in the *E. coli* cell culture, at different time points cell cultures were centrifuged, and the supernatants were collected, heat-denatured and loaded onto an SDS-PAGE gel. To detect Myc tag monoclonal antibody (Thermo Fisher Scientific, MA1-21316) stability in *E. coli* cell culture, goat anti-mouse IgG1 Cross-Adsorbed Secondary Antibody, Alexa Fluor 488 (Thermo Fisher Scientific, A-21121) was used as the primary antibody for western blots.

Time-Lapse Fluorescent Intensity Analysis on a Plate Reader

TOP10 pro with LamB knockout cells containing the plasmids of interest were streaked on LB plates and grown for 24-36 h at 37° C. Single colonies were inoculated into 800 μl LB in V-bottom 96-well plate (Nunc, 249952) with antibiotics. The plates were sealed with gas-permeable adhesive plate seals (Fisher Scientific, AB-0718) and incubated at 800 rpm and 37° C. overnight. Then the overnight cultures were diluted into 800 μl M9 medium in a V-bottom 96-well plate and grown at 37° C. at 800 rpm for 4 h with start OD600=0.1. Next, inducers IPTG and aTc were added to induce MalT and LamB expression at 30° C. for 8 h. Then the cells were collected by centrifugation and resuspended in M9 medium with antibiotics to a final OD600=2.0. M9 cell culture (200 μl) was added into a round-bottom 96-well plate (Corning, 351177), and after a 30-min incubation with the antibody at 37° C., maltodextrin was added as the inducer and the plate was placed into the plate reader (Cytation, Biotek) to monitor the reporter fluorescent protein expression levels.

To set up the kinetic monitoring program on the plate reader, the incubation temperature was set to 37° C. and the continuous shaking rate was 807 rpm in double orbital mode. OD600, YFP fluorescence intensity (ex/em=500 nm/550 nm), and mCherry fluorescence intensity (ex/em=560 nm/630 nm) were monitored at 30 minute intervals for 16 h.

Flow Cytometry Analysis

The induced cell culture with extracellular antibody treatment at 37° C. for 8 h was washed 2 times with PBS and then diluted 1:10 by adding 20 μl of cell culture into 180 μl of PBS. Fluorescence was measured using the BD Accuri™ C6 flow cytometer (BD Biosciences). For each sample, at least 50,000 cells were used for analysis in the C6 Plus Analysis Software.

Example 7

Engineering Other Porin Transporters and Induction Systems

Due to the modularity of this biosensor design, other porin transporters and induction systems in bacteria can be similarly adapted to be utilized for the protein-sensing purposes. Specifically, this biosensor system requires three key components: 1) a porin that facilitates chemical transport into the cytoplasm; 2) target-specific peptide(s) inserted in the porin loops; and 3) a gene regulatory system in the cytoplasm that is controlled by the transported compounds. In gram-negative bacteria, examples of other porins that satisfy these requirements include sucrose-specific porin ScrY, cobalamin-specific porin BtuB, ferrochrome-specific porin FhuA, and nucleoside specific porin TsX.

For instance, the sucrose transporter ScrY and the sucrose-inducible promoter can be engineered in a conceptually analogous manner to the LamB-based biosensor. FIG. 7 shows how to implement this design approach in the sucrose-specific porin ScrY. First, the genomic ScrY sequence in the host strain will be knocked out to eliminate the background sucrose transport. Next, target-specific binding peptides such as the anti-FLAG or anti-myc epitope will be introduced into the external loops of an ScrY transgene, which will be cloned into and expressed by a plasmid introduced into the bacteria. Based on the alignment of the structures of LamB and ScrY, external loop 5 and loop 8 of ScrY will be likely candidates for target-specific binding peptide insertion. Last, for the internal gene regulatory system in cytoplasm, a sucrose-inducible promoter system for intracellular protein production has been shown in Bacillus megaterium. For signal output of the biosensor, the sucrose-inducible promoter will be cloned into a second plasmid to control expression of the repressor SrpR. A YFP reporter under control of the repressible promoter $P_{Srp}$ will be the same as in the LamB biosensor. To test this biosensor developed with the sucrose-specific porin ScrY and sucrose-inducible promoter $P_{sacB}$, sucrose will be added into the medium as the inducer and anti-FLAG-tag antibody will be the target protein. Anti-FLAG-tag antibody will specifically bind to the FLAG-tag epitopes inserted into the ScrY loops, thereby blocking sucrose transport via ScrY channels. As a result, the YFP reporter protein will be expressed in cytoplasm in the absence of sucrose-mediated induction of the repressor SrpR.

Example 8

Biosensor System for Regulated Inhibition of a Reporter Gene

A system that allows for regulated inhibition of expression used the E. coli cells and LamB protein comprising the protein ligand peptide insertions described in the previous Examples. In FIG. 8A, a biosensor developed in gram-negative E. coli cells comprising three components is shown. The components of the biosensor include: 1) maltose/maltodextrin transporter LamB on the outer membrane; 2) target-specific binding peptides displayed in the outer loops of LamB; and 3) maltose induction system in the cytoplasm. LamB, as an outer membrane porin, is responsible for the uptake of maltose and maltodextrins into the periplasm, which is the first step of the E. coli maltose/maltodextrin transport system. MalT, as a transcriptional activator, binds maltose to induce gene transcription controlled by a MalT-dependent promoter. Target-specific binding peptides were genetically inserted into the LamB DNA sequence and were expressed as LamB fusions in the extracellular loops. Certain protein molecules in the medium (e.g., FLAG mAb or myc mAb) can bind to the target-specific binding peptides inserted in LamB (e.g., FLAG epitopes and myc epitopes bound by the FLAG mAb or myc mAb, respectively), thus sterically blocking the channels for maltodextrin transport. As a result, the expression of a protein of interest (e.g., mCherry) induced by maltodextrin and the MalT-dependent promoter were repressed by extracellular molecules that bind the target-specific binding peptides displayed on the LamB transporter. In summary, the expression of mCherry is reduced due to the lower maltose concentration in the cytoplasm due to blocking of the LamB transporter via specific binding of the extracellular target protein to the introduced target specific binding peptides in LamB. In FIG. 8B, time curves of mCherry expression in E. coli with LamB fusions with FLAG epitopes expressed and with different concentrations of anti-FLAG tag antibody added in the medium are shown. In FIG. 8C, time curves of mCherry expression in E. coli with LamB fusions with myc epitopes expressed and with different concentrations of anti-myc tag antibody added in the medium are shown. In FIG. 8D, a dose-response curve of mCherry expression versus FLAG-tag antibody concentrations at 7 h is shown. In FIG. 8E, a dose-response curve of mCherry expression versus myc-tag antibody concentrations at 7 h is shown.

Example 9

Alternative Biosensor Systems for Increased Expression in Presence of Extracellular Target Molecules In order to invert the signal output in a system comprising the E. coli cells and LamB protein comprising the protein ligand peptide insertions so that the reporter protein can be expressed in the presence of extracellular target proteins, a NOT gate can be introduced in the downstream signaling pathway. Examples of such NOT gates are shown in FIGS. 9A, B, C, and D. In the last step of the signal transduction, the output can be inverted as shown in FIG. 9B through transcription repression (Stanton et al. 2014, doi:10.1038/nchembio.1411), as shown in FIG. 9C by translation deactivation by decoy RNA (Green et al. 2017, doi:10.1038/nature23271), or as shown in FIG. 9D by post-translational protein degradation (Fernandez-Rodriguez and Voigt, 2016, doi:10.1093/nar/gkw537). Alternatively, if the compound represses an inducible promoter, then blocking internalization of the compound via target binding to a porin containing a heterologous target-specific peptide would also promote increased reporter protein expression, as shown in FIG. 10.

| SEQUENCES[1] | |
|---|---|
| LamB<br>*E. coli*<br>(SEQ ID NO: 1) | *MMITLRKLPLAVAVAAGVMSAQAMA-*<br>VDFHGYARSGIGWTGSGGEQQCFQTTGAQSKYRLGNECETY<br>AELKLGQEVWKEGDKSFYFDTNVAYSVAQQNDWEATDPAF<br>REANVQGKNLIEWLPGSTIWAGKRFYQRHDVHMIDFYYWDI<br>SGPGAGLENIDVGFGKLSLAATRSSEAGGSSSFASNNIYDYTN<br>ETANDVFDVRLAQMEINPGGTLELGVDYGRANLRDNYRLVD<br>GASKDGWLFTAEHTQSVLKGFNKFVVQYATDSMTSQGKGLS<br>QGSGVAFDNEKFAYNINNNGHMLRILDHGAISMGDNWDMM<br>YVGMYQDINWDNDGTKWWTVGIRPMYKWTPIMSTVMEIG<br>YDNVESQRTGDKNNQYKITLAQQWQAGDSIWSRPAIRVFAT<br>YAKWDEKWGYDYTGNADNNANFGKAVPADFNGGSFGRGD<br>SDEWTFGAQMEIWW |
| LamB mutant<br>(R109A, Y118A)<br>*E. coli*<br>(SEQ ID NO: 2) | *MMITLRKLPLAVAVAAGVMSAQAMA-*<br>VDFHGYARSGIGWTGSGGEQQCFQTTGAQSKYRLGNECETY<br>AELKLGQEVWKEGDKSFYFDTNVAYSVAQQNDWEATDPAF<br>REANVQGKNLIEWLPGSTIWAGKRFYQAHDVHMIDFAYWDI<br>SGPGAGLENIDVGFGKLSLAATRSSEAGGSSSFASNNIYDYTN<br>ETANDVFDVRLAQMEINPGGTLELGVDYGRANLRDNYRLVD<br>GASKDGWLFTAEHTQSVLKGFNKFVVQYATDSMTSQGKGLS<br>QGSGVAFDNEKFAYNINNNGHMLRILDHGAISMGDNWDMM<br>YVGMYQDINWDNDGTKWWTVGIRPMYKWTPIMSTVMEIG<br>YDNVESQRTGDKNNQYKITLAQQWQAGDSIWSRPAIRVFAT<br>YAKWDEKWGYDYTGNADNNANFGKAVPADFNGGSFGRGD<br>SDEWTFGAQMEIWW |
| ScrY<br>*E. coli*<br>(SEQ ID NO: 3) | *MYKKTTLAVLIALLTGATTVHA-*<br>QTDISSIESRLAALEQRLKNAESRAQAAEARAKTAELQVQKL<br>AETQQQNQLTTQEVAQRTVQLEQKSAENSGFEFHGYARSGL<br>LMNDAGSSSKSGPYLTPAGETGGAVGRLGKEADTYVELNVE<br>HKQTLDNGATTRFKAMLADGQRDYNDWTGGSSNLNIRQAF<br>AELGALPSFTGAFQDSTVWAGKRFDRDNFDIHWLDSDVVFL<br>AGTGGGIYDVKWNDTFRSNFSLYGRNFGDLDDIDNNVQNYIL<br>TMNHYAGPFQLMVSGLGAKDNDDRKDGNGDLIQTDAANTG<br>VHALVGLHNDTFYGLREGTAKTALLYGHGLGAEVKGIGSDG<br>ALLSEANTWRFASYGTTPLGSGWYVAPAILAQSSKDRYVKG<br>DSYEWVTFNTRLIKEVTQNFALAFEGSYQYMDLKPKGYQNH<br>NAVNGSFYKLTFAPTLKANDINNFFSRPELRLFATWMDWSSK<br>LDDFASNDAFGSSGFNTGGEWNFGVQMETWF |
| ScrY<br>*Salmonella*<br>*typhimurium*<br>(SEQ ID NO: 4) | *MYRKSTLAMLIALLTSAASAHA-*<br>QTDISTIEARLNALEKRLQEAENRAQTAENRAGAAEKKVQQL<br>TAQQQKNQNSTQEVAQRTARLEKKADDKSGFEFHGYARSGV<br>IMNDSGASTKSGAYITPAGETGGAIGRLGNQADTYVEMNLEH<br>KQTLDNGATTRFKVMVADGQTSYNDWTASTSDLNVRQAFV<br>ELGNLPTFAGPFKGSTLWAGKRFDRDNFDIHWIDSDVVFLAG<br>TGGGIYDVKWNDGLRSNFSLYGRNFGDIDDSSNSVQNYILTM<br>NHFAGPLQMMVSGLRAKDNDERKDSNGNLAKGDAANTGVH<br>ALLGLHNDSFYGLRDGSSKTALLYGHGLGAEVKGIGSDGALR<br>PGADTWRIASYGTTPLSENWSVAPAMLAQRSKDRYADGDSY<br>QWATFNLRLIQAINQNFALAYEGSYQYMDLKPEGYNDRQAV<br>NGSFYKLTFAPTFKVGSIGDFFSRPEIRFYTSWMDWSKKLNN<br>YASDDALGSDGFNSGGEWSFGVQMETWF |
| BtuB<br>*E. coli*<br>(SEQ ID NO: 5) | *MIKKASLLTACSVTAFSAWA-*<br>QDTSPDTLVVTANRFEQPRSTVLAPTTVVTRQDIDRWQSTSV<br>NDVLRRLPGVDITQNGGSGQLSSIFIRGTNASHVLVLIDGVRL<br>NLAGVSGSADLSQFPIALVQRVEYIRGPRSAVYGSDAIGGVV<br>NIITTRDEPGTEISAGWGSNSYQNYDVSTQQQLGDKTRVTLL<br>GDYAHTHGYDVVAYGNTGTQAQTDNDGFLSKTLYGALEHN<br>FTDAWSGFVRGYGYDNRTNYDAYYSPGSPLLDTRKLYSQSW<br>DAGLRYNGELIKSQLITSYSHSKDYNYDPHYGRYDSSATLDE<br>MKQYTVQWANNVIVGHGSIGAGVDWQKQTTTPGTGYVEDG<br>YDQRNTGIYLTGLQQVGDFTFEGAARSDDNSQFGRHGTWQT<br>SAGWEFIEGYRFIASYGTSYKAPNLGQLYGFYGNPNLDPEKS<br>KQWEGAFEGLTAGVNWRISGYRNDVSDLIDYDDHTLKYYNE<br>GKARIKGVEATANFDTGPLTHTVSYDYVDARNAITDTPLLRR<br>AKQQVKYQLDWQLYDFDWGITYQYLGTRYDKDYSSYPYQT<br>VKMGGVSLWDLAVAYPVTSHLTVRGKIANLFDKDYETVYG<br>YQTAGREYTLSGSYTF |
| FhuA<br>*E. coli*<br>(SEQ ID NO: 6) | *MARSKTAQPKHSLRKIAVWATAVSGMSVYAQA-*<br>AVEPKEDTITVTAAPAPQESAWGPAATIAARQSATGTKTDTPI<br>QKVPQSISVVTAEEMALHQPKSVKEALSYTPGVSVGTRGASN<br>TYDHLIIRGFAAEGQSQNNYLNGLKLQGNFYNDAVIDPYMLE<br>RAEIMRGPVSVLYGKSSPGGLLNMVSKRPTTEPLKEVQFKAG<br>TDSLFQTGFDFSDSLDDDGVYSYRLTGLARSANAQQKGSEEQ<br>RYAIAPAFTWRPDDKTNFTFLSYFQNEPETGYYGWLPKEGTV<br>EPLPNGKRLPTDFNEGAKNNTYSRNEKMVGYSFDHEFNDTFT |

-continued

| SEQUENCES[1] |
| --- |

VRQNLRFAENKTSQNSVYGYGVCSDPANAYSKQCAALAPAD
KGHYLARKYVVDDEKLQNFSVDTQLQSKFATGDIDHTLLTG
VDFMRMRNDINAWFGYDDSVPLLNLYNPVNTDFDFNAKDPA
NSGPYRILNKQKQTGVYVQDQAQWDKVLVTLGGRYDWAD
QESLNRVAGTTDKRDDKQFTWRGGVNYLFDNGVTPYFSYSE
SFEPSSQVGKDGNIFAPSKGKQYEVGVKYVPEDRPIVVTGAV
YNLTKTNNLMADPEGSFFSVEGGEIRARGVEIEAKAALSASV
NVVGSYTYTDAEYTTDTTYKGNTPAQVPKHMASLWADYTFF
DGPLSGLTLGTGGRYTGSSYGDPANSFKVGSYTVVDALVRY
DLARVGMAGSNVALHVNNLFDREYVASCFNTYGCFWGAER
QVVATATFRF

FepA
*E. coli*
(SEQ ID NO: 7)

*MNKKIHSLALLVNLGIYGVAQA-*
QEPTDTPVSHDDTIVVTAAEQNLQAPGVSTITADEIRKNPVAR
DVSKIIRTMPGVNLTGNSTSGQRGNNRQIDIRGMGPENTLILID
GKPVSSRNSVRQGWRGERDTRGDTSWVPPEMIERIEVLRGPA
AARYGNGAAGGVVNIITKKGSGEWHGSWDAYFNAPEHKEE
GATKRTNFSLTGPLGDEFSFRLYGNLDKTQADAWDINQGHQS
ARAGTYATTLPAGREGVINKDINGVVRWDFAPLQSLELEAGY
SRQGNLYAGDTQNTNSDSYTRSKYGDETNRLYRQNYALTW
NGGWDNGVTTSNWVQYEHTRNSRIPEGLAGGTEGKFNEKAT
QDFVDIDLDDVMLHSEVNLPIDFLVNQTLTLGTEWNQQRMK
DLSSNTQALTGTNTGGAIDGVSTTDRSPYSKAEIFSLFAENNM
ELTDSTIVTPGLRFDHHSIVGNNWSPALNISQGLGDDFTLKMG
IARAYKAPSLYQTNPNYILYSKGQGCYASAGGCYLQGNDDL
KAETSINKEIGLEFKRDGWLAGVTWFRNDYRNKIEAGYVAV
GQNAVGTDLYQWDNVPKAVVEGLEGSLNVPVSETVMWTNN
ITYMLKSENKTTGDRLSIIPEYTLNSTLSWQAREDLSMQTTFT
WYGKQQPKKYNYKGQPAVGPETKEISPYSIVGLSATWDVTK
NVSLTGGVDNLFDKRLWRAGNAQTTGDLAGANYIAGAGAY
TYNEPGRTWYMSVNTHF

TsX
*E. coli*
(SEQ ID NO: 8)

*MKKTLLAAGAVLALSSSFTVNA-*
AENDKPQYLSDWWHQSVNVVGSYHTRFGPQIRNDTYLEYEA
FAKKDWFDFYGYADAPVFFGGNSDAKGIWNHGSPLFMEIEP
RFSIDKLTNTDLSFGPFKEWYFANNYIYDMGRNKDGRQSTW
YMGLGTDIDTGLPMSLSMNVYAKYQWQNYGAANENEWDG
YRFKIKYFVPITDLWGGQLSYIGFTNFDWGSDLGDDSGNAIN
GIKTRTNNSIASSHILALNYDHWHYSVVARYWHDGGQWNDD
AELNFGNGNFNVRSTGWGGYLVVGYNF

YddB
*E. coli*
(SEQ ID NO: 9)

*MKRVLIPGVILCGADVAQA-*
VDDKNMYMHFFEEMTVYAPVPVPVNGNTHYTSESIERLPTG
NGNISDLLRTNPAVRMDSTQSTSLNQGDIRPEKISIHGASPYQ
NAYLIDGISATNNLNPANESDASSATNISGMSQGYYLDVSLLD
NVTLYDSFVPVEFGRFNGGVIDAKIKRFNADDSKVKLGYRTT
RSDWLTSHIDENNKSAFNQGSSGSTYYSPDFKKNFYTLSFNQE
LADNFGVTAGLSRRQSDITRADYVSNDGIVAGRAQYKNVIDT
ALSKFTWFASDRFTHDLTLKYTGSSRDYNTSTFPQSDREMGN
KSYGLAWDMDTQLAWAKLRTTVGWDHISDYTRHDHDIWYT
ELSCTYGDITGRCTRGGLGHISQAVDNYTFKTRLDWQKFAVG
NVSHQPYFGAEYIYSDAWTERHNQSESYVINAAGKKTNHTIY
HKGKGRLGIDNYTLYMADRISWRNVSLMPGVRYDYDNYLS
NHNISPRFMTEWDIFANQTSMITAGYNRYYGGNILDMGLRDI
RNSWTESVSGNKTLTRYQDLKTPYNDELAMGLQQKIGKNVI
ARANYVYREAHDQISKSSRTDSATKTTITEYNNDGKTKTHSF
SLSFELAEPLHIRQVDINPQIVFSYIKSKGNLSLNNGYEESNTG
DNQVVYNGNLVSYDSVPVADFNNPLKISLNMDFTHQPSGLV
WANTLAWQEARKARIILGKTNAQYISEYSDYKQYVDEKLDS
SLTWDTRLSWTPQFLQQQNLTISADILNVLDSKTAVDTTNTG
VATYASGRTFWLDVSMKF

OmpA
*E. coli*
(SEQ ID NO: 10)

*MKKTAIAIAVALAGFATVAQA-*
APKDNTWYTGAKLGWSQYHDTGFINNNGPTHENQLGAGAF
GGYQVNPYVGFEMGYDWLGRMPYKGSVENGAYKAQGVQL
TAKLGYPITDDLDIYTRLGGMVWRADTKSNVYGKNHDTGVS
PVFAGGVEYAITPEIATRLEYQWTNNIGDAHTIGTRPDNGMLS
LGVSYRFGQGEAAPVVAPAPAPAPEVQTKHFTLKSDVLFNFN
KATLKPEGQAALDQLYSQLSNLDPKDGSVVVLGYTDRIGSDA
YNQGLSERRAQSVVDYLISKGIPADKISARGMGESNPVTGNT
CDNVKQRAALIDCLAPDRRVEIEVKGIKDVVTQPQA

OmpC
*E. coli*
(SEQ ID NO: 11)

*MKVKVLSLLVPALLVAGAANA-*
AEVYNKDGNKLDLYGKVDGLHYFSDNKDVDGDQTYMRLGF
KGETQVTDQLTGYGQWEYQIQGNSAENENNSWTRVAFAGL
KFQDVGSFDYGRNYGVVYDVTSWTDVLPEFGGDTYGSDNF
MQQRGNGFATYRNTDFFGLVDGLNFAVQYQGKNGNPSGEG

| SEQUENCES[1] |
|---|

FTSGVTNNGRDALRQNGDGVGGSITYDYEGFGIGGAISSSKRT
DAQNTAAYIGNGDRAETYTGGLKYDANNIYLAAQYTQTYNA
TRVGSLGWANKAQNFEAVAQYQFDFGLRPSLAYLQSKGKNL
GRGYDDEDILKYVDVGATYYFNKNMSTYVDYKINLLDDNQF
TRDAGINTDNIVALGLVYQF

OmpF
*E. coli*
(SEQ ID NO: 12)

*MMKRNILAVIVPALLVAGTANA-*
AEIYNKDGNKVDLYGKAVGLHYFSKGNGENSYGGNGDMTY
ARLGFKGETQINSDLTGYGQWEYNFQGNNSEGADAQTGNKT
RLAFAGLKYADVGSFDYGRNYGVVYDALGYTDMLPEFGGD
TAYSDDFFVGRVGGVATYRNSNFFGLVDGLNFAVQYLGKNE
RDTARRSNGDGVGGSISYEYEGFGIVGAYGAADRTNLQEAQP
LGNGKKAEQWATGLKYDANNIYLAANYGETRNATPITNKFT
NTSGFANKTQDVLLVAQYQFDFGLRPSIAYTKSKAKDVEGIG
DVDLVNYFEVGATYYFNKNMSTYVDYIINQIDSDNKLGVGS
DDTVAVGIVYQF

PhoE
*E. coli*
(SEQ ID NO: 13)

*MKKSTLALWMGIVASASVQA-*
AEIYNKDGNKLDVYGKVKAMHYMSDNASKDGDQSYIRFGF
KGETQINDQLTGYGRWEAEFAGNKAESDTAQQKTRLAFAGL
KYKDLGSFDYGRNLGALYDVEAWTDMFPEFGGDSSAQTDNF
MTKRASGLATYRNTDFFGVIDGLNLTLQYQGKNENRDVKKQ
NGDGFGTSLTYDFGGSDFAISGAYTNSDRTNEQNLQSRGTK
RAEAWATGLKYDANNIYLATFYSETRKMTPITGGFANKTQNF
EAVAQYQFDFGLRPSLGYVLSKGKDIEGIGDEDLVNYIDVGA
TYYFNKNMSAFVDYKINQLDSDNKLNINNDDIVAVGMTYQF

OmpX
*E. coli*
(SEQ ID NO: 14)

*MKKIACLSALAAVLAFTAGTSVA-*
ATSTVTGGYAQSDAQGQMNKMGGFNLKYRYEEDNSPLGVIG
SFTYTEKSRTASSGDYNKNQYYGITAGPAYRINDWASIYGVV
GVGYGKFQTTEYPTYKHDTSDYGFSYGAGLQFNPMENVALD
FSYEQSRIRSVDVGTWIAGVGYRF

DNA sequence
of sucrose-
inducible
promoter P*sacB*
and Met
initiation codon
in FIG. 7D (SEQ
ID NO: 15;
Biedendieck, R.
et al. A sucrose-
inducible
promoter system
for the intra- and
extracellular
protein
production in
*Bacillus
megaterium. J.
Biotechnol.* 132,
426-430 (2007).

5'-
CTGATTCCAGCCGTGAAGGAAAAGCAACTGGTTTAGACTC
TTAATATTCAAAAAATGCATTATACGCTCTCTCTTTTTACA
AAAGGGAGAGCGTATAATGCATTAAAAAAGATAAAAATG
AGTAGGTAAAAAGAAGGAATATTTTTTTCTGAAAACATAC
TTTAGACCTTTATTATTATCATCCTAATCTTTAGAAAGGAA
AAAGAATAGAACGTTTTCATGTCCGGCTAATAAAAAAAAG
GTACTGATTTTTCAAGAGATAAAAACAGAATGGTCGGAAA
GTATAAAAACGAATGGTCGGAAAGTATAAAAAACGGAAT
AGCGTTTTCAATGCTGGAAAGATAAAGTGTTTAATCATGTA
GAAAGTATCAAACGCAACGTCTGGAAATCGTGGTTTGAAA
TGTAAAAAAGCCATTTTTGTTGGAAAAACGGTTACATAAA
AAAGGCTCTTACACGTAAACTTTGGTCCTAGTTACAGCTCA
ATGAAAAAGATAAAAATGAGAAATAGCTACATTTGGCATG
TTTGACTTTCGTCATTTATCCAAGTAATCTTTTGGTTGAACG
GAACCGGTTCTGTTTTCGGATTTTTGATAGCTAATTGAATT
AATAAATTTATATTCTTTACTAACACAAAAGGAGAAAACA
TATG-3'

FLAG-tag
(SEQ ID NO: 16)

DYKDDDDK myc-tag
(SEQ ID NO: 17)

EQKLISEED

KCF18
(SEQ ID NO: 18)

KCRKEMFKQKLPYSTVYF

P(Mal)
(SEQ ID NO: 19)

5'-
AGTGGTTGAGATCACATTTCCTTGCTCATCCCCGCAACTCC
TCCCTGCCTAATCCCCCGCAGGATGAGGAAGGTCAACATC
GAGCCTGGCAAACTAGCGATAACGTTGTGTTGAAAATCTA
AGAAAAGTGGCGGCCGC-3'

P(SrpR)
(SEQ ID NO: 20)

5'-
TTTATACGACGTACGGTGGAAGATTCGTTACCAATTGACAG
CTAGCTCAGTCCTAGGTATATACATACATGCTTGTTTGTTT
GTAAACTACTAGAGAAAGAGGAGAAATACTAG-3'

| SEQUENCES[1] |

| | |
|---|---|
| High-Efficiency Terminator (SEQ ID NO: 21) | 5'-CAAATAAAACGAAAGGCTCAGTCGAAAGACTGGGCCTTTC GTTTTATCTGTTGTTTGTCGGTGAACGCTCTCCTGAGTAGG ACAAATGAGCGGAAGAGCGCCCAATACGCAAACCGCCTC TCCCCGCGCGTTGGCCGATTCATTAATGCAGCTGGCACGAC AGGTTTCCCGACTGGAAAGCGGGCAGTGAGCGCAAGGTCT CTGATCCTTAAGCCAGCCCCGACACCCGCCAACACCCGCT GACGCGCCTCGGTACCAAATTTTCGAAAAAAGACGCTGAA AAGCGTCTTTTTTCGTTTTGGTCC-3' |
| pdt#3 (SEQ ID NO: 22) | 5'-GCGGCGAACAAAAACGAAGAAAACACCAACGAAGTGCCG ACCTTTATGCTGAACGCGGGCCAGGCGAACAGAAGACGAG TT-3' |
| LamB(FLAG) (SEQ ID NO: 23) | MMITLRKLPLAVAVAAGVMSAQAMAVDFHGYARSGIGWTG SGGEQQCFQTTGAQSKYRLGNECETYAELKLGQEVWKEGDK SFYFDTNVAYSVAQQNDWEATDPAFREANVQGKNLIEWLPG STIWAGKRFYQRHDVHMIDFYYWDISGPGAGLENIDVGFGKL SLAATRSSEAGGSSDYKDDDDKSFASNNIYDYTNETANDVFD VRLAQMEINPGGTLELGVDYGRANLRDNYRLVDGASKDGW LFTAEHTQSVLKGFNKFVVQYATDSMTSQGKGLSQGSGVAF DNEKFAYNINNNGHMLRILDHGAISMGDNWDMMYVGMYQ DINWDNDNGTKWWTVGIRPMYKWTPIMSTVMEIGYDNVES QRTGDKNNQYKITLAQQWQAGDSIWSRPAIRVFATYAKWDE KWGYDYTGNADNDYKDDDDKNANFGKAVPADFNGGSFGR GDSDEWTFGAQMEIWW |
| LamB(Myc) (SEQ ID NO: 24) | MMITLRKLPLAVAVAAGVMSAQAMAVDFHGYARSGIGWTG SGGEQQCFQTTGAQSKYRLGNECETYAELKLGQEVWKEGDK SFYFDTNVAYSVAQQNDWEATDPAFREANVQGKNLIEWLPG STIWAGKRFYQRHDVHMIDFYYWDISGPGAGLENIDVGFGKL SLAATRSSEAGGSSEQKLISEEDLSFASNNIYDYTNETANDVF DVRLAQMEINPGGTLELGVDYGRANLRDNYRLVDGASKDG WLFTAEHTQSVLKGFNKFVVQYATDSMTSQGKGLSQGSGVA FDNEKFAYNINNNGHMLRILDHGAISMGDNWDMMYVGMYQ DINWDNDNGTKWWTVGIRPMYKWTPIMSTVMEIGYDNVES QRTGDKNNQYKITLAQQWQAGDSIWSRPAIRVFATYAKWDE KWGYDYTGNADNEQKLISEEDLNANFGKAVPADFNGGSFG RGDSDEWTFGAQMEIWW |
| LamB(KCF18) (SEQ ID NO: 25) | MMITLRKLPLAVAVAAGVMSAQAMAVDFHGYARSGIGWTG SGGEQQCFQTTGAQSKYRLGNECETYAELKLGQEVWKEGDK SFYFDTNVAYSVAQQNDWEATDPAFREANVQGKNLIEWLPG STIWAGKRFYQRHDVHMIDFYYWDISGPGAGLENIDVGFGKL SLAATRSSEAGGSSKCRKEMFKQKLPYSTVYFSFASNNIYD YTNETANDVFDVRLAQMEINPGGTLELGVDYGRANLRDNYR LVDGASKDGWLFTAEHTQSVLKGFNKFVVQYATDSMTSQG KGLSQGSGVAFDNEKFAYNINNNGHMLRILDHGAISMGDNW DMMYVGMYQDINWDNDNGTKWWTVGIRPMYKWTPIMSTV MEIGYDNVESQRTGDKNNQYKITLAQQWQAGDSIWSRPAIR VFATYAKWDEKWGYDYTGNADNKCRKEMFKQKLPYSTV YFNANFGKAVPADFNGGSFGRGDSDEWTFGAQMEIWW |

[1]Signal peptide sequences are at N-terminus and in italics; mature protein sequences follow and are not italicized.

SEQUENCE LISTING

Sequence total quantity: 25
SEQ ID NO: 1            moltype = AA   length = 446
FEATURE                 Location/Qualifiers
source                  1..446
                        mol_type = protein
                        organism = Escherichia coli
SIGNAL                  1..25
SEQUENCE: 1
MMITLRKLPL AVAVAAGVMS AQAMAVDFHG YARSGIGWTG SGGEQQCFQT TGAQSKYRLG    60
NECETYAELK LGQEVWKEGD KSFYFDTNVA YSVAQQNDWE ATDPAFREAN VQGKNLIEWL   120
PGSTIWAGKR FYQRHDVHMI DFYYWDISGP GAGLENIDVG FGKLSLAATR SSEAGGSSSF   180
ASNNIYDYTN ETANDVFDVR LAQMEINPGG TLELGVDYGR ANLRDNYRLV DGASKDGWLF   240
TAEHTQSVLK GFNKFVVQYA TDSMTSQGKG LSQGSGVAFD NEKFAYNINN NGHMLRILDH   300
GAISMGDNWD MMYVGMYQDI NWDNDNGTKW WTVGIRPMYK WTPIMSTVME IGYDNVESQR   360
TGDKNNQYKI TLAQQWQAGD SIWSRPAIRV FATYAKWDEK WGYDYTGNAD NNANFGKAVP   420

-continued

```
ADFNGGSFGR GDSDEWTFGA QMEIWW                                                446

SEQ ID NO: 2            moltype = AA   length = 446
FEATURE                 Location/Qualifiers
source                  1..446
                        mol_type = protein
                        organism = Escherichia coli
SIGNAL                  1..25
SEQUENCE: 2
MMITLRKLPL AVAVAAGVMS AQAMAVDFHG YARSGIGWTG SGGEQQCFQT TGAQSKYRLG      60
NECETYAELK LGQEVWKEGD KSFYFDTNVA YSVAQQNDWE ATDPAFREAN VQGKNLIEWL      120
PGSTIWAGKR FYQAHDVHMI DFAYWDISGP GAGLENIDVG FGKLSLAATR SSEAGGSSSF      180
ASNNIYDYTN ETANDVFDVR LAQMEINPGG TLELGVDYGR ANLRDNYRLV DGASKDGWLF      240
TAEHTQSVLK GFNKFVVQYA TDSMTSQGKG LSQGSGVAFD NEKFAYNINN NGHMLRILDH      300
GAISMGDNWD MMYVGMYQDI NWDNDNGTKW WTVGIRPMYK WTPIMSTVME IGYDNVESQR      360
TGDKNNQYKI TLAQQWQAGD SIWSRPAIRV FATYAKWDEK WGYDYTGNAD NNANFGKAVP      420
ADFNGGSFGR GDSDEWTFGA QMEIWW                                          446

SEQ ID NO: 3            moltype = AA   length = 505
FEATURE                 Location/Qualifiers
source                  1..505
                        mol_type = protein
                        organism = Escherichia coli
SIGNAL                  1..22
SEQUENCE: 3
MYKKTTLAVL IALLTGATTV HAQTDISSIE SRLAALEQRL KNAESRAQAA EARAKTAELQ      60
VQKLAETQQQ NQLTTQEVAQ RTVQLEQKSA ENSGFEFHGY ARSGLLMNDA GSSSKSGPYL      120
TPAGETGGAV GRLGKEADTY VELNVEHKQT LDNGATTRFK AMLADGQRDY NDWTGGSSNL      180
NIRQAFAELG ALPSFTGAFQ DSTVWAGKRF DRDNFDIHWL DSDVVFLAGT GGGIYDVKWN      240
DTFRSNFSLY GRNFGDLDDI DNNVQNYILT MNHYAGPFQL MVSGLGAKDN DDRKDGNGDL      300
IQTDAANTGV HALVGLHNDT FYGLREGTAK TALLYGHGLG AEVKGIGSDG ALLSEANTWR      360
FASYGTTPLG SGWYVAPAIL AQSSKDRYVK GDSYEWVTFN TRLIKEVTQN FALAFEGSYQ      420
YMDLKPKGYQ NHNAVNGSFY KLTFAPTLKA NDINNFFSRP ELRLFATWMD WSSKLDDFAS      480
NDAFGSSGFN TGGEWNFGVQ METWF                                           505

SEQ ID NO: 4            moltype = AA   length = 505
FEATURE                 Location/Qualifiers
source                  1..505
                        mol_type = protein
                        organism = Salmonella typhimurium
SIGNAL                  1..22
SEQUENCE: 4
MYRKSTLAML IALLTSAASA HAQTDISTIE ARLNALEKRL QEAENRAQTA ENRAGAAEKK      60
VQQLTAQQQK NQNSTQEVAQ RTARLEKKAD DKSGFEFHGY ARSGVIMNDS GASTKSGAYI      120
TPAGETGGAI GRLGNQADTY VEMNLEHKQT LDNGATTRFK VMVADGQTSY NDWTASTSDL      180
NVRQAFVELG NLPTFAGPFK GSTLWAGKRF DRDNFDIHWI DSDVVFLAGT GGGIYDVKWN      240
DGLRSNFSLY GRNFGDIDDS SNSVQNYILT MNHFAGPFQL MVSGLRAKDN DERKDSNGNL      300
AKGDAANTGV HALLGLHNDS FYGLRDGSSK TALLYGHGLG AEVKGIGSDG ALRPGADTWR      360
IASYGTTPLS ENWSVAPAML AQRSKDRYAD GDSYQWATFN LRLIQAINQN FALAYEGSYQ      420
YMDLKPEGYN DRQAVNGSFY KLTFAPTFKV GSIGDFFSRP EIRFYTSWMD WSKKLNNYAS      480
DDALGSDGFN SGGEWSFGVQ METWF                                           505

SEQ ID NO: 5            moltype = AA   length = 614
FEATURE                 Location/Qualifiers
source                  1..614
                        mol_type = protein
                        organism = Escherichia coli
SIGNAL                  1..20
SEQUENCE: 5
MIKKASLLTA CSVTAFSAWA QDTSPDTLVV TANRFEQPRS TVLAPTTVVT RQDIDRWQST      60
SVNDVLRRLP GVDITQNGGS GQLSSIFIRG TNASHVLVLI DGVRLNLAGV SGSADLSQFP      120
IALVQRVEYI RGPRSAVYGS DAIGGVVNII TTRDEPGTEI SAGWGSNSYQ NYDVSTQQQL      180
GDKTRVTLLG DYAHTHGYDV VAYGNTGTQA QTDNDGFLSK TLYGALEHNF TDAWSGFVRG      240
YGYDNRTNYD AYYSPGSPLL DTRKLYSQSW DAGLRYNGEL IKSQLITSYS HSKDYNYDPH      300
YGRYDSSATL DEMKQYTVQW ANNVIVGHGS IGAGVDWQKQ TTTPGTGYVE DGYDQRNTGI      360
YLTGLQQVGD FTFEGAARSD DNSQFGRHGT WQTSAGWEFI EGYRFIASYG TSYKAPNLGQ      420
LYGFYGNPNL DPEKSKQWEG AFEGLTAGVN WRISGYRNDV SDLIDYDDHT LKYYNEGKAR      480
IKGVEATANF DTGPLTHTVS YDYVDARNAI TDTPLLRRAK QQVKYQLDWQ LYDFDWGITY      540
QYLGTRYDKD YSSYPYQTVK MGGVSLWDLA VAYPVTSHLT VRGKIANLFD KDYETVYGYQ      600
TAGREYTLSG SYTF                                                       614

SEQ ID NO: 6            moltype = AA   length = 747
FEATURE                 Location/Qualifiers
source                  1..747
                        mol_type = protein
                        organism = Escherichia coli
SIGNAL                  1..33
SEQUENCE: 6
MARSKTAQPK HSLRKIAVVV ATAVSGMSVY AQAAVEPKED TITVTAAPAP QESAWGPAAT      60
```

```
IAARQSATGT KTDTPIQKVP QSISVVTAEE MALHQPKSVK EALSYTPGVS VGTRGASNTY   120
DHLIIRGFAA EGQSQNNYLN GLKLQGNFYN DAVIDPYMLE RAEIMRGPVS VLYGKSSPGG   180
LLNMVSKRPT TEPLKEVQFK AGTDSLFQTG FDFSDSLDDD GVYSYRLTGL ARSANAQQKG   240
SEEQRYAIAP AFTWRPDDKT NFTFLSYFQN EPETGYYGWL PKEGTVEPLP NGKRLPTDFN   300
EGAKNNTYSR NEKMVGYSFD HEFNDTFTVR QNLRFAENKT SQNSVYGYGV CSDPANAYSK   360
QCAALAPADK GHYLARKYVV DDEKLQNFSV DTQLQSKFAT GDIDHTLLTG VDFMRMRNDI   420
NAWFGYDDSV PLLNLYNPVN TDFDFNAKDP ANSGPYRILN KQKQTGVYVQ DQAQWDKVLV   480
TLGGRYDWAD QESLNRVAGT TDKRDDKQFT WRGGVNYLFD NGVTPYFSYS ESFEPSSQVG   540
KDGNIFAPSK GKQYEVGVKY VPEDRPIVVT GAVYNLTKTN NLMADPEGSF FSVEGGEIRA   600
RGVEIEAKAA LSASVNVVGS YTYTDAEYTT DTTYKGNTPA QVPKHMASLW ADYTFFDGPL   660
SGLTLGTGGR YTGSSYGDPA NSFKVGSYTV VDALVRYDLA RVGMAGSNVA LHVNNLFDRE   720
YVASCFNTYG CFWGAERQVV ATATFRF                                      747

SEQ ID NO: 7              moltype = AA  length = 746
FEATURE                   Location/Qualifiers
source                    1..746
                          mol_type = protein
                          organism = Escherichia coli
SIGNAL                    1..22
SEQUENCE: 7
MNKKIHSLAL LVNLGIYGVA QAQEPTDTPV SHDDTIVVTA AEQNLQAPGV STITADEIRK   60
NPVARDVSKI IRTMPGVNLT GNSTSGQRGN NRQIDIRGMG PENTLILIDG KPVSSRNSVR   120
QGWRGERDTR GDTSWVPPEM IERIEVLRGP AAARYGNGAA GGVVNIITKK GSGEWHGSWD   180
AYFNAPEHKE EGATKRTNFS LTGPLGDEFS FRLYGNLDKT QADAWDINQG HQSARAGTYA   240
TTLPAGREGV INKDINGVVR WDFAPLQSLE LEAGYSRQGN LYAGDTQNTN SDSYTRSKYG   300
DETNRLYRQN YALTWNGGWD NGVTTSNWVQ YEHTRNSRIP EGLAGGTEGK FNEKATQDFV   360
DIDLDDVMLH SEVNLPIDFL VNQTLTLGTE WNQQRMKDLS SNTQALTGTN TGGAIDGVST   420
TDRSPYSKAE IFSLFAENNM ELTDSTIVTP GLRFDHHSIV GNNWSPALNI SQGLGDDFTL   480
KMGIARAYKA PSLYQTNPNY ILYSKGQGCY ASAGGCYLQG NDDLKAETSI NKEIGLEFKR   540
DGWLAGVTWF RNDYRNKIEA GYVAVGQNAV GTDLYQWDNV PKAVVEGLEG SLNVPVSETV   600
MWTNNITYML KSENKTTGDR LSIIPEYTLN STLSWQARED LSMQTTFTWY GKQQPKKYNY   660
KGQPAVGPET KEISPYSIVG LSATWDVTKN VSLTGGVDNL FDKRLWRAGN AQTTGDLAGA   720
NYIAGAGAYT YNEPGRTWYM SVNTHF                                       746

SEQ ID NO: 8              moltype = AA  length = 294
FEATURE                   Location/Qualifiers
source                    1..294
                          mol_type = protein
                          organism = Escherichia coli
SIGNAL                    1..22
SEQUENCE: 8
MKKTLLAAGA VLALSSSFTV NAAENDKPQY LSDWWHQSVN VVGSYHTRFG PQIRNDTYLE   60
YEAFAKKDWF DFYGYADAPV FFGGNSDAKG IWNHGSPLFM EIEPRFSIDK LTNTDLSFGP   120
FKEWYFANNY IYDMGRNKDG RQSTWYMGLG TDIDTGLPMS LSMNVYAKYQ WQNYGAANEN   180
EWDGYRFKIK YFVPITDLWG GQLSYIGFTN FDWGSDLGDD SGNAINGIKT RTNNSIASSH   240
ILALNYDHWH YSVVARYWHD GGQWNDDAEL NFGNGNFNVR STGWGGYLVV GYNF         294

SEQ ID NO: 9              moltype = AA  length = 790
FEATURE                   Location/Qualifiers
source                    1..790
                          mol_type = protein
                          organism = Escherichia coli
SIGNAL                    1..19
SEQUENCE: 9
MKRVLIPGVI LCGADVAQAV DDKNMYMHFF EEMTVYAPVP VPVNGNTHYT SESIERLPTG   60
NGNISDLLRT NPAVRMDSTQ STSLNQGDIR PEKISIHGAS PYQNAYLIDG ISATNNLNPA   120
NESDASSATN ISGMSQGYYL DVSLLDNVTL YDSFVPVEFG RFNGGVIDAK IKRFNADDSK   180
VKLGYRTTRS DWLTSHIDEN NKSAFNQGSS GSTYYSPDFK KNFYTLSFNQ ELADNFGVTA   240
GLSRRQSDIT RADYVSNDGI VAGRAQYKNV IDTALSKFTW FASDRFTHDL TLKYTGSSRD   300
YNTSTFPQSD REMGNKSYGL AWDMDTQLAW AKLRTTVGWD HISDYTRHDH DIWYTELSCT   360
YGDITGRCTR GGLGHISQAV DNYTFKTRLD WQKFAVGNVS HQPYFGAEYI YSDAWTERHN   420
QSESYVINAA GKKTNHTIYH KGKGRLGIDN YTLYMADRIS WRNVSLMPGV RYDYDNYLSN   480
HNISPRFMTE WDIFANQTSM ITAGYNRYYG GNILDMGLRD IRNSWTESVS GNKTLTRYQD   540
LKTPYNDELA MGLQQKIGKN VIARANYVYR EAHDQISKSS RTDSATKTTI TEYNNDGKTK   600
THSFSLSFEL AEPLHIRQVD INPQIVFSYI KSKGNLSLNN GYEESNTGDN QVVYNGNLVS   660
YDSVPVADFN NPLKISLNMD FTHQPSGLVW ANTLAWQEAR KARIILGKTN AQYISEYSDY   720
KQYVDEKLDS SLTWDTRLSW TPQFLQQQNL TISADILNVL DSKTAVDTTN TGVATYASGR   780
TFWLDVSMKF                                                         790

SEQ ID NO: 10             moltype = AA  length = 346
FEATURE                   Location/Qualifiers
source                    1..346
                          mol_type = protein
                          organism = Escherichia coli
SIGNAL                    1..21
SEQUENCE: 10
MKKTAIAIAV ALAGFATVAQ AAPKDNTWYT GAKLGWSQYH DTGFINNNGP THENQLGAGA   60
FGGYQVNPYV GFEMGYDWLG RMPYKGSVEN GAYKAQGVQL TAKLGYPITD DLDIYTRLGG   120
MVWRADTKSN VYGKNHDTGV SPVFAGGVEY AITPEIATRL EYQWTNNIGD AHTIGTRPDN   180
```

```
GMLSLGVSYR FGQGEAAPVV APAPAPAPEV QTKHFTLKSD VLFNFNKATL KPEGQAALDQ   240
LYSQLSNLDP KDGSVVVLGY TDRIGSDAYN QGLSERRAQS VVDYLISKGI PADKISARGM   300
GESNPVTGNT CDNVKQRAAL IDCLAPDRRV EIEVKGIKDV VTQPQA                  346

SEQ ID NO: 11             moltype = AA   length = 367
FEATURE                   Location/Qualifiers
source                    1..367
                          mol_type = protein
                          organism = Escherichia coli
SIGNAL                    1..21
SEQUENCE: 11
MKVKVLSLLV PALLVAGAAN AAEVYNKDGN KLDLYGKVDG LHYFSDNKDV DGDQTYMRLG   60
FKGETQVTDQ LTGYGQWEYQ IQGNSAENEN NSWTRVAFAG LKFQDVGSFD YGRNYGVVYD   120
VTSWTDVLPE FGGDTYGSDN FMQQRGNGFA TYRNTDFFGL VDGLNFAVQY QGKNGNPSGE   180
GFTSGVTNNG RDALRQNGDG VGGSITYDYE GFGIGGAISS SKRTDAQNTA AYIGNGDRAE   240
TYTGGLKYDA NNIYLAAQYT QTYNATRVGS LGWANKAQNF EAVAQYQFDF GLRPSLAYLQ   300
SKGKNLGRGY DDEDILKYVD VGATYYFNKN MSTYVDYKIN LLDDNQFTRD AGINTDNIVA   360
LGLVYQF                                                             367

SEQ ID NO: 12             moltype = AA   length = 362
FEATURE                   Location/Qualifiers
source                    1..362
                          mol_type = protein
                          organism = Escherichia coli
SIGNAL                    1..22
SEQUENCE: 12
MMKRNILAVI VPALLVAGTA NAAEIYNKDG NKVDLYGKAV GLHYFSKGNG ENSYGGNGDM   60
TYARLGFKGE TQINSDLTGY GQWEYNFQGN NSEGADAQTG NKTRLAFAGL KYADVGSFDY   120
GRNYGVVYDA LGYTDMLPEF GGDTAYSDDF FVGRVGGVAT YRNSNFFGLV DGLNFAVQYL   180
GKNERDTARR SNGDGVGGSI SYEYEGFGIV GAYGAADRTN LQEAQPLGNG KKAEQWATGL   240
KYDANNIYLA ANYGETRNAT PITNKFTNTS GFANKTQDVL LVAQYQFDFG LRPSIAYTKS   300
KAKDVEGIGD VDLVNYFEVG ATYYFNKNMS TYVDYIINQI DSDNKLGVGS DDTVAVGIVY   360
QF                                                                 362

SEQ ID NO: 13             moltype = AA   length = 351
FEATURE                   Location/Qualifiers
source                    1..351
                          mol_type = protein
                          organism = Escherichia coli
SIGNAL                    1..21
SEQUENCE: 13
MKKSTLALVV MGIVASASVQ AAEIYNKDGN KLDVYGKVKA MHYMSDNASK DGDQSYIRFG   60
FKGETQINDQ LTGYGRWEAE FAGNKAESDT AQQKTRLAFA GLKYKDLGSF DYGRNLGALY   120
DVEAWTDMFP EFGGDSSAQT DNFMTKRASG LATYRNTDFF GVIDGLNLTL QYQGKNENRD   180
VKKQNGDGFG TSLTYDFGGS DFAISGAYTN SDRTNEQNLQ SRGTGKRAEA WATGLKYDAN   240
NIYLATFYSE TRKMTPITGG FANKTQNFEA VAQYQFDFGL RPSLGYVLSK GKDIEGIGDE   300
DLVNYIDVGA TYYFNKNMSA FVDYKINQLD SDNKLNINND DIVAVGMTYQ F           351

SEQ ID NO: 14             moltype = AA   length = 171
FEATURE                   Location/Qualifiers
source                    1..171
                          mol_type = protein
                          organism = Escherichia coli
SIGNAL                    1..23
SEQUENCE: 14
MKKIACLSAL AAVLAFTAGT SVAATSTVTG GYAQSDAQGQ MNKMGGFNLK YRYEEDNSPL   60
GVIGSFTYTE KSRTASSGDY NKNQYYGITA GPAYRINDWA SIYGVVGVGY GKFQTTEYPT   120
YKHDTSDYGF SYGAGLQFNP MENVALDFSY EQSRIRSVDV GTWIAGVGYR F           171

SEQ ID NO: 15             moltype = DNA   length = 649
FEATURE                   Location/Qualifiers
source                    1..649
                          mol_type = genomic DNA
                          organism = Bacillus megaterium
SEQUENCE: 15
ctgattccag ccgtgaagga aaagcaactg gtttagactc ttaatattca aaaaatgcat   60
tatacgctct ctcttttac aaaagggaga gcgtataatg cattaaaaaa gataaaaatg   120
agtaggtaaa aagaaggaat attttttct gaaaacatac tttagacctt tattattatc   180
atcctaatct ttagaaagga aaagaatag aacgttttca tgtccggcta ataaaaaaa   240
ggtactgatt tttcaagaga taaaaacaga atggtcggaa agtataaaaa cgaatggtcg   300
gaaagtataa aaaacggaat agcgttttca atgctggaaa gataaagtgt ttaatcatgt   360
agaaagtatc aaacgcaacg tctgaaatc gtggtttgaa atgtaaaaaa gccatttttg   420
ttggaaaaac ggtacataa aaaaggctct tacacgtaaa ctttggtcct agttacagct   480
caatgaaaaa gataaaaatg agaaatagct acatttgact gtttgactt tcgtcattta   540
tccaagtaat ctttttggttg aacgaaccg gttctgtttt cggatttttg atagctaatt   600
gaattaataa atttatattc tttactaaca caaaaggaga aaacatatg              649

SEQ ID NO: 16             moltype = AA   length = 8
FEATURE                   Location/Qualifiers
```

```
source                  1..8
                        mol_type = protein
                        organism = synthetic construct
SEQUENCE: 16
DYKDDDDK                                                                   8

SEQ ID NO: 17           moltype = AA   length = 9
FEATURE                 Location/Qualifiers
source                  1..9
                        mol_type = protein
                        organism = synthetic construct
SEQUENCE: 17
EQKLISEED                                                                  9

SEQ ID NO: 18           moltype = AA   length = 18
FEATURE                 Location/Qualifiers
source                  1..18
                        mol_type = protein
                        organism = synthetic construct
SEQUENCE: 18
KCRKEMFKQK LPYSTVYF                                                        18

SEQ ID NO: 19           moltype = DNA   length = 138
FEATURE                 Location/Qualifiers
source                  1..138
                        mol_type = other DNA
                        organism = synthetic construct
SEQUENCE: 19
agtggttgag atcacatttc cttgctcatc cccgcaactc ctccctgcct aatcccccgc   60
aggatgagga aggtcaacat cgagcctggc aaactagcga taacgttgtg ttgaaaatct   120
aagaaaagtg gcggccgc                                                   138

SEQ ID NO: 20           moltype = DNA   length = 114
FEATURE                 Location/Qualifiers
source                  1..114
                        mol_type = other DNA
                        organism = synthetic construct
SEQUENCE: 20
tttatacgac gtacggtgga agattcgtta ccaattgaca gctagctcag tcctaggtat   60
atacatacat gcttgtttgt ttgtaaacta ctagagaaag aggagaaata ctag         114

SEQ ID NO: 21           moltype = DNA   length = 306
FEATURE                 Location/Qualifiers
source                  1..306
                        mol_type = other DNA
                        organism = synthetic construct
SEQUENCE: 21
caaataaaac gaaaggctca gtcgaaagac tgggcctttc gttttatctg ttgtttgtcg   60
gtgaacgctc tcctgagtag gacaaatgaa gcggaagagc gcccaatacg caaaccgcct   120
ctccccgcgc gttggccgat tcattaatgc agctggcacg acaggtttcc cgactggaaa   180
gcgggcagtg agcgcaaggt ctctgatcct taagccagcc ccgacacccg ccaacacccg   240
ctgacgcgcc tcggtaccaa attttcgaaa aaagacgctg aaaagcgtct tttttcgttt   300
tggtcc                                                               306

SEQ ID NO: 22           moltype = DNA   length = 81
FEATURE                 Location/Qualifiers
source                  1..81
                        mol_type = other DNA
                        organism = synthetic construct
SEQUENCE: 22
gcggcgaaca aaaacgaaga aaacaccaac gaagtgccga cctttatgct gaacgcgggc   60
caggcgaaca gaagacgagt t                                               81

SEQ ID NO: 23           moltype = AA   length = 462
FEATURE                 Location/Qualifiers
source                  1..462
                        mol_type = protein
                        organism = synthetic construct
SEQUENCE: 23
MMITLRKLPL AVAVAAGVMS AQAMAVDFHG YARSGIGWTG SGGEQQCFQT TGAQSKYRLG   60
NECETYAELK LGQEVWKEGD KSFYFDTNVA YSVAQQNDWE ATDPAFREAN VQGKNLIEWL   120
PGSTIWAGKR FYQRHDVHMI DFYYWDISGP GAGLENIDVG FGKLSLAATR SSEAGGSSDY   180
KDDDDKSFAS NNIYDYTNET ANDVFDVRLA QMEINPGGTL ELGVDYGRAN LRDNYRLVDG   240
ASKDGWLFTA EHTQSVLKGF NKFVVQYATD SMTSQGKGLS QGSGVAFDNE KFAYNINNNG   300
HMLRILDHGA ISMGDNWDMM YVGMYQDINW DNDNGTKWWT VGIRPMYKWT PIMSTVMEIG   360
YDNVESQRTG DKNNQYKITL AQQWQAGDSI WSRPAIRVFA TYAKWDEKWG YDYTGNADND   420
YKDDDDKNAN FGKAVPADFN GGSFGRGDSD EWTFGAQMEI WW                        462

SEQ ID NO: 24           moltype = AA   length = 466
```

-continued

```
FEATURE             Location/Qualifiers
source              1..466
                    mol_type = protein
                    organism = synthetic construct
SEQUENCE: 24
MMITLRKLPL AVAVAAGVMS AQAMAVDFHG YARSGIGWTG SGGEQQCFQT TGAQSKYRLG  60
NECETYAELK LGQEVWKEGD KSFYFDTNVA YSVAQQNDWE ATDPAFREAN VQGKNLIEWL  120
PGSTIWAGKR FYQRHDVHMI DFYYWDISGP GAGLENIDVG FGKLSLAATR SSEAGGSSEQ  180
KLISEEDLSF ASNNIYDYTN ETANDVFDVR LAQMEINPGG TLELGVDYGR ANLRDNYRLV  240
DGASKDGWLF TAEHTQSVLK GFNKFVVQYA TDSMTSQGKG LSQGSGVAFD NEKFAYNINN  300
NGHMLRILDH GAISMGDNWD MMYVGMYQDI NWDNDNGTKW WTVGIRPMYK WTPIMSTVME  360
IGYDNVESQR TGDKNNQYKI TLAQQWQAGD SIWSRPAIRV FATYAKWDEK WGYDYTGNAD  420
NEQKLISEED LNANFGKAVP ADFNGGSFGR GDSDEWTFGA QMEIWW              466

SEQ ID NO: 25        moltype = AA   length = 482
FEATURE              Location/Qualifiers
source               1..482
                     mol_type = protein
                     organism = synthetic construct
SEQUENCE: 25
MMITLRKLPL AVAVAAGVMS AQAMAVDFHG YARSGIGWTG SGGEQQCFQT TGAQSKYRLG  60
NECETYAELK LGQEVWKEGD KSFYFDTNVA YSVAQQNDWE ATDPAFREAN VQGKNLIEWL  120
PGSTIWAGKR FYQRHDVHMI DFYYWDISGP GAGLENIDVG FGKLSLAATR SSEAGGSSKC  180
RKEMFKQKLP YSTVYFSFAS NNIYDYTNET ANDVFDVRLA QMEINPGGTL ELGVDYGRAN  240
LRDNYRLVDG ASKDGWLFTA EHTQSVLKGF NKFVVQYATD SMTSQGKGLS QGSGVAFDNE  300
KFAYNINNNG HMLRILDHGA ISMGDNWDMM YVGMYQDINW DNDNGTKWWT VGIRPMYKWT  360
PIMSTVMEIG YDNVESQRTG DKNNQYKITL AQQWQAGDSI WSRPAIRVFA TYAKWDEKWG  420
YDYTGNADNK CRKEMFKQKL PYSTVYFNAN FGKAVPADFN GGSFGRGDSD EWTFGAQMEI  480
WW                                                               482
```

What is claimed is:

1. A bacterial cell comprising:
(i) a first outer membrane transport protein comprising a heterologous target-specific binding peptide inserted in an extracellular portion of the membrane transport protein;
(ii) an inducible promoter which is operably linked to a polynucleotide encoding a repressor protein, wherein said promoter is induced by a compound, and wherein the compound is internalized within the cell by the first outer membrane transport protein; and
(iii) a first repressible promoter which is operably linked to a polynucleotide encoding at least a protein and/or a bioactive RNA molecule of interest, wherein said first repressible promoter can be repressed by the repressor protein.

2. The bacterial cell of claim 1, wherein the bacterial cell lacks a second outer membrane transport protein which can internalize the compound within the cell.

3. The bacterial cell of claim 1, wherein the compound is maltose or maltodextrin.

4. The bacterial cell of claim 1, wherein the outer membrane transport protein is a LamB porin.

5. The bacterial cell of claim 1, wherein: (i) the first repressible promoter is operably linked to the protein and/or a bioactive RNA molecule of interest and to a polynucleotide encoding a protein which can inactivate the repressor protein; or (ii) the bacterial cell further comprises a second repressible promoter under control of the repressor protein, wherein the second repressible promoter is operably linked to a polynucleotide encoding a protein which can inactivate the repressor protein.

6. The bacterial cell of claim 1, wherein the bacterial cell is in an extracellular media comprising a target which binds to the heterologous target-specific binding peptide and the compound and wherein internalization of the compound is inhibited by the presence of the target.

7. The bacterial cell of claim 1, wherein extracellular presence of the compound and a target which binds to the heterologous target-specific binding peptide results in an increase in expression of the protein of interest or the bioactive RNA molecule in comparison to expression of the protein of interest or the bioactive RNA molecule in the extracellular presence of the compound when the target is present at lower concentrations or absent.

8. A system for detection of target in a sample comprising the bacterial cell of claim 1 in an extracellular media comprising the target and the compound.

9. A method of detecting a target of interest in a sample, the method comprising:
(i) contacting the bacterial cell of claim 1 with the sample and the compound, wherein the protein of interest comprises a reporter protein; and
(ii) detecting the reporter protein to determine the presence of the target in the sample, wherein expression of the reporter protein is increased in samples containing the target in comparison to expression of the reporter protein in a control bacterial cell contacted with the compound and a control sample lacking or deficient in the target.

10. A bacterial cell comprising:
(i) a first outer membrane transport protein comprising a heterologous target-specific binding peptide inserted in an extracellular portion of the membrane transport protein;
(ii) a first promoter which is inducible and operably linked to a polynucleotide encoding a regulator protein and/or a regulator RNA molecule, wherein said promoter is induced by a compound, and wherein the compound is internalized within the cell by the outer membrane transport protein; and
(iii) a second promoter which is operably linked to a protein and/or a bioactive RNA molecule of interest, wherein the second promoter is repressed by the regulator protein or wherein expression of the protein of interest is inhibited by the regulator protein and/or wherein the expression of the protein of interest is inhibited by the regulator RNA molecule.

11. The bacterial cell of claim 10, wherein the bacterial cell is in an extracellular media comprising a target which binds to the heterologous target-specific binding peptide and the compound and wherein internalization of the compound is inhibited by the presence of the target which binds to the heterologous target-specific binding peptide.

12. A system for increasing expression of a protein of interest and/or a bioactive RNA molecule comprising the bacterial cell of claim 10, the target, and the compound, wherein the bacterial cell, the target, and the compound are in an extracellular media or are in a subject.

13. A method of detecting a target of interest in a sample, the method comprising:

(i) contacting the bacterial cell of claim 10 with the sample and the compound, wherein the protein of interest comprises a reporter protein; and (ii) detecting the reporter protein to determine the presence of the target in the sample, wherein expression of the reporter protein is increased in samples containing the target in comparison to expression of the reporter protein in a control bacterial cell contacted with the compound and a control sample lacking or deficient in the target.

* * * * *